: US008953837B2

(12) United States Patent
Gilad-Gilor

(10) Patent No.: US 8,953,837 B2
(45) Date of Patent: Feb. 10, 2015

(54) SYSTEM AND METHOD FOR PERFORMING AN AUTOMATIC AND SELF-GUIDED MEDICAL EXAMINATION

(75) Inventor: David Gilad-Gilor, Even Yehuda (IL)

(73) Assignee: Tyto Care Ltd., Netanya (IL)

( * ) Notice: Subject to any disclaimer, the term of this patent is extended or adjusted under 35 U.S.C. 154(b) by 0 days.

(21) Appl. No.: 14/000,374

(22) PCT Filed: Feb. 16, 2012

(86) PCT No.: PCT/IL2012/050050
§ 371 (c)(1),
(2), (4) Date: Aug. 19, 2013

(87) PCT Pub. No.: WO2012/111012
PCT Pub. Date: Aug. 23, 2012

(65) Prior Publication Data
US 2013/0331664 A1   Dec. 12, 2013

Related U.S. Application Data

(60) Provisional application No. 61/443,767, filed on Feb. 17, 2011.

(51) Int. Cl.
*G06K 9/00* (2006.01)
*A61B 5/00* (2006.01)
(Continued)

(52) U.S. Cl.
CPC ............... *A61B 5/6898* (2013.01); *A61B 5/00* (2013.01); *A61B 5/0077* (2013.01); *A61B 5/067* (2013.01);
(Continued)

(58) Field of Classification Search
CPC ........................................ A61B 7/00

USPC ......... 600/300, 301, 407, 476, 586; 382/100, 382/128
See application file for complete search history.

(56) References Cited

U.S. PATENT DOCUMENTS

| 4,770,189 A | 9/1988 | Shyu |
| 5,010,889 A | 4/1991 | Bredesen et al. |

(Continued)

FOREIGN PATENT DOCUMENTS

| EP | 2050544 | 4/2009 |
| WO | WO 95/13112 | 5/1995 |

(Continued)

OTHER PUBLICATIONS

U.S. Appl. No. 14/000,375, filed Aug. 19, 2013, David Gilad-Gilor et al.
(Continued)

*Primary Examiner* — Samir Ahmed
(74) *Attorney, Agent, or Firm* — Workman Nydegger

(57) ABSTRACT

A method for performing one or more medical examinations of a patient using a diagnostics device, wherein for at least one medical examination of the medical examinations, the method comprising: providing reference data indicative of a desired spatial disposition of the device with respect to the patient's body for performing the medical examination; operating the device for acquiring navigation enabling data; determining a spatial disposition of the device with respect to the desired spatial disposition, utilizing the acquired navigation enabling data and the reference data; calculating a required movement correction from the determined spatial disposition to the desired spatial disposition, for acquiring medical data of the patient in accordance with the at least one medical examination; providing a user with maneuvering instructions to navigate the device to the desired spatial disposition in accordance with the calculated route; and acquiring the medical data upon arrival to the desired spatial disposition.

56 Claims, 22 Drawing Sheets

(51) Int. Cl.
*A61B 5/06* (2006.01)
*G06F 19/00* (2011.01)
*A61B 7/00* (2006.01)

(52) U.S. Cl.
CPC ........ *G06F 19/3406* (2013.01); *G06F 19/3418* (2013.01); *A61B 5/0013* (2013.01); *A61B 5/7246* (2013.01); *A61B 5/741* (2013.01); *A61B 5/742* (2013.01); *A61B 5/7455* (2013.01); *A61B 7/00* (2013.01); *A61B 5/6843* (2013.01); *A61B 5/0022* (2013.01); *A61B 2562/0257* (2013.01)
USPC ............................ 382/100; 382/128; 600/586

(56) References Cited

U.S. PATENT DOCUMENTS

| | | | |
|---|---|---|---|
| 5,527,261 | A | 6/1996 | Monroe et al. |
| 5,638,819 | A | 6/1997 | Manwaring et al. |
| 6,014,432 | A | 1/2000 | Modney |
| 6,544,198 | B2 | 4/2003 | Chong et al. |
| 6,711,293 | B1 | 3/2004 | Lowe |
| 6,778,846 | B1 | 8/2004 | Martinez et al. |
| 7,162,063 | B1 | 1/2007 | Craine et al. |
| 7,280,916 | B2 | 10/2007 | Bang et al. |
| 8,204,576 | B2 | 6/2012 | Ikuma et al. |
| 8,466,801 | B2 | 6/2013 | Hayes et al. |
| 2002/0188227 | A1 | 12/2002 | Chong et al. |
| 2003/0036683 | A1 | 2/2003 | Kehr et al. |
| 2003/0069752 | A1 | 4/2003 | LeDain et al. |
| 2003/0114980 | A1* | 6/2003 | Klausner et al. ............... 701/207 |
| 2005/0065813 | A1 | 3/2005 | Mishelevich et al. |
| 2005/0273359 | A1 | 12/2005 | Young |
| 2006/0100521 | A1 | 5/2006 | Takeuchi |
| 2006/0155589 | A1 | 7/2006 | Lane et al. |
| 2007/0088521 | A1 | 4/2007 | Shmueli et al. |
| 2007/0208263 | A1 | 9/2007 | John et al. |
| 2008/0052121 | A1 | 2/2008 | Iliff |
| 2008/0077434 | A1 | 3/2008 | Man et al. |
| 2008/0166033 | A1 | 7/2008 | Bueno et al. |
| 2008/0208912 | A1 | 8/2008 | Garibaldi |
| 2008/0242951 | A1 | 10/2008 | Jung et al. |
| 2009/0054736 | A1 | 2/2009 | Rantala et al. |
| 2009/0112769 | A1 | 4/2009 | Dicks et al. |
| 2009/0163774 | A1 | 6/2009 | Thatha et al. |
| 2009/0299155 | A1 | 12/2009 | Yang et al. |
| 2010/0016682 | A1 | 1/2010 | Schluess et al. |
| 2010/0052915 | A1 | 3/2010 | Allen et al. |
| 2010/0312484 | A1 | 12/2010 | DuHamel et al. |
| 2011/0015504 | A1 | 1/2011 | Yoo |
| 2011/0034786 | A1* | 2/2011 | Cadio et al. ................... 600/316 |
| 2011/0165688 | A1* | 7/2011 | Dupoteau et al. ............... 436/55 |
| 2012/0179035 | A1 | 7/2012 | Boudier |

FOREIGN PATENT DOCUMENTS

| | | |
|---|---|---|
| WO | WO 97/00708 | 1/1997 |
| WO | WO 02/09580 | 2/2002 |
| WO | WO 02/054945 | 7/2002 |
| WO | WO 2005/096205 | 10/2005 |
| WO | WO 2005/114524 | 12/2005 |
| WO | WO 2007/060558 | 5/2007 |
| WO | WO 2008/070322 | 6/2008 |
| WO | WO 2008/094435 | 8/2008 |
| WO | WO 2009/032392 | 3/2009 |
| WO | WO 2009/054783 | 4/2009 |
| WO | WO 2010/015968 | 2/2010 |
| WO | WO 2010/102069 | 9/2010 |

OTHER PUBLICATIONS

Lowe, David G. "Object recognition from local scale-invariant features." Computer vision, 1999. The proceedings of the seventh IEEE international conference on. vol. 2. Ieee, 1999.
Titterton, David. Strapdown inertial navigation technology. vol. 17. IET, 2004, pp. 40-47.
http://www.fiercemobilehealthcare.com/story/bluetooth-stethoscope-and-diagnostic-software-honored-life-saving-potential/2009-11-17 (Sep. 19, 2010).
http://www.neurosynaptic.com/index.html (Sep. 19, 2010).
Bratan, Tanja, and Malcolm Clarke. "Optimum design of remote patient monitoring systems." Engineering in Medicine and Biology Society, 2006. EMBS'06. 28th Annual International Conference of the IEEE. IEEE, 2006.
Yousef, Jasemian, and A. N. Lars. "Validation of a real-time wireless telemedicine system, using bluetooth protocol and a mobile phone, for remote monitoring patient in medical practice." Eur J Med Res 10.6 (2005): 254-62.
Khan, Jamil Y., Mehmet R. Yuce, and Farbood Karami. "Performance evaluation of a wireless body area sensor network for remote patient monitoring." Engineering in Medicine and Biology Society, 2008. EMBS 2008. 30th Annual International Conference of the IEEE. IEEE, 2008.
Lin, Chao-Hung, Shuenn-Tsong Young, and Te-Son Kuo. "A remote data access architecture for home-monitoring health-care applications." Medical engineering & physics 29.2 (2007): 199-204.
Zhang, Pu, et al. "A remote patient monitoring system using a Java-enabled 3G mobile phone." Engineering in Medicine and Biology Society, 2007. EMBS 2007. 29th Annual International Conference of the IEEE. IEEE, 2007.
Maglogiannis, Hies, et al. "Risk analysis of a patient monitoring system using Bayesian Network modeling." Journal of Biomedical Informatics 39.6 (2006): 637-647.
Al-Rousan, Mohammad, Abdul-Rahman Al-Ali, and Armin Eberlein. "Remote patient monitoring and information system." International Journal of Electronic Healthcare 2.3 (2006): 231-249.
http://www.mako.co.il/news-israel/health/Article-3f2ce7629aedb21004.htm&sCh=31750a2610f26110&pId=416320364 (Oct. 25, 2010).
http://en.wikipedia.org/wiki/Scale-invariant_feature_transform (Feb. 1, 2011) 14 pgs.
Parnian, Neda. Integration of Local Positioning System & Strapdown Inertial Navigation System for Hand-Held Tool Tracking. Diss. University of Waterloo, 2008.

* cited by examiner

Record the reference data comprised of, inter alia one or more synchronized channels of:
- External body imaging (video) – using a camera module
- Inertial Navigation System (INS) data
- Distance sensor data
- Pressure sensor data
- Organ imaging (video) – using camera module and specific organ peripheral
- Organ sound – using device's microphone & specific organ peripheral

SYSTEM AND METHOD FOR PERFORMING AN AUTOMATIC AND SELF-GUIDED MEDICAL EXAMINATION

FIELD OF THE PRESENTLY DISCLOSED SUBJECT MATTER

This invention relates to the field of medical examinations, and more specifically to the field of automatic and self-guided medical examinations.

BACKGROUND

Prior art references considered to be relevant as background to the presently disclosed subject matter are listed below. Listings of the references herein is not to be inferred as admitting that these are in any way relevant to the patentability of the presently disclosed subject matter disclosed herein. In addition, references cited in the application are not necessarily admitted as being prior art.

U.S. Pat. No. 6,544,198 (Chong et al.) issued Apr. 8, 2003 discloses a stethoscope system for self-examination whereby the condition of health of a particular individual can be diagnosed by comparing characteristic sound waves classified by diseases with sound waves generated from various parts of the individual's body. This system also provides for remote medical examination whereby sound waves generated from various parts of the individual's body are transmitted to a medical specialist using the Internet and receiving a virtual medical examination via the Internet.

U.S. Pat. No. 6,014,432 (Mondey) issued Jan. 11, 2000 discloses a home health care system comprising: patient station including a first videophone, an electronic imaging assembly and a stethoscope assembly, coupled to said first videophone, for respectively producing digital image and physiological sound signals of a patient, wherein said first videophone simultaneously transmits said digital signals over a public telecommunications network; and a health care provider's station including a second videophone, a video display and a sound reproducer, wherein the second videophone receives digital signals from the first videophone over the public telecommunications network, displays the images of the patient on the display, and reproduces the physiological sounds of the patient by the sound reproducer.

U.S. Pat. No. 5,527,261 (Monroe et al.) issued Jun. 18, 1996 discloses a hand-held, fully remote diagnostic instrument having video capability that is configured for any one of a number of clinical or industrial applications. The instrument has a casing that includes a hand-holdable body portion, a neck portion that extends from the body portion to a head portion that is formed of a back cover, a front cover, and a sealing gasket to form a fully soakable instrument. A circuit board assembly in the body portion contains video processing circuitry, and a flexible neck board which extends forward from the body portion through the neck portion of the casing to a head board located in the head portion of the casing. A solid state imager and a miniature lamp are disposed on the head board. The front cover contains an adjustable focus lens cell for focusing on the imager an image of a target in the lens cell's field of view. The instrument can be configured for various applications by installing front and back covers that are suited for a specific purpose. The instrument can thus be used, for example, as an otoscope, a dental camera, or an episcope. The instrument provides a monitor-ready standard format full color video signal to a remotely located monitor.

SUMMARY

The inventors have found that nowadays, people are often required to perform medical examinations. Such checks may be required as a routine check-up, according to a patients request, or in light of a need that arises (such as, for example, when a person does not feel well). Normally, such checks are performed during a face to face visit by medically trained personnel (e.g. a physician, a nurse, etc.) in light of the fact that there is a need of certain knowledge, as well as equipment, in order to perform such checks. It is estimated that there are billions of medical examinations performed each year. It is to be noted that the number of general checks is expected to grow in the future as the average life expectancy keeps rising, and elderly people tend to use more medical service. It is also to be noted that there is a constant decline in the number of medically trained personnel (e.g. physicians and nurses) that can serve the community, thus creating a reduced availability and growth of service load. Each such medical examination requires the patient to meet with trained personnel, at a certain location (e.g. clinic, hospital, patient's house, etc.).

There is thus a need in the art for a new system and method that will reduce the load and increase the availability of trained personnel by performing an automatic and self-guided medical examination.

In accordance with an aspect of the presently disclosed subject matter, there is provided a handheld diagnostics device for performing at least one medical examination, the diagnostics device comprising at least one diagnostics sensor and a processor, wherein for each of the at least one medical examinations the processor is configured to provide medical data acquisition guidance to a user based on pre-defined reference data; operate the at least one diagnostics sensor to acquire medical data of a patient.

In accordance with one example of the presently disclosed subject matter, there is further provided a handheld diagnostics device further comprising at least one navigation sensor operable to acquire position data, and wherein the processor is further configured to receive navigation data from the at least one navigation sensors and reference data; utilize the navigation data and the reference data, in order to calculate position of the diagnostic device with respect to the patient; calculate a route from the position of the diagnostics device to a desired position of the diagnostics device, in accordance with the reference data; provide navigational guidance to the user; acquire data relating to the at least one medical examination when the diagnostics device is in the desired position.

In accordance with one example of the presently disclosed subject matter, there is still further provided a handheld diagnostics device wherein the medical data acquisition guidance includes at least one of the following:
  (a) an indication of a check to be performed;
  (b) navigational instructions;
  (c) operational instructions;
  (d) positioning instructions;
  (e) examination process instructions.

In accordance with one example of the presently disclosed subject matter, there is still further provided a handheld diagnostics device wherein the processor is further configured to verify that the acquired data meets pre-defined standards.

In accordance with one example of the presently disclosed subject matter, there is still further provided a handheld diagnostics device wherein the pre-defined standards are at least one of:
  (a) the required length of reading;
  (b) recorded sound volume;
  (c) reading parameters thresholds;
  (d) the type of image reading;
  (e) the required image reading zoom;
  (f) the required image reading light;

(g) the required image reading matching to predefined reference.

In accordance with an aspect of the presently disclosed subject matter, there is still further provided a method for operating a handheld diagnostics device for performing at least one medical examination, for each of the at least one medical examinations the method comprising providing medical data acquisition guidance to a user based on pre-defined reference data, and operating the at least one diagnostics sensor to acquire medical data of a patient.

In accordance with one example of the presently disclosed subject matter, there is still further provided a method further comprising receiving navigation data and reference data, utilizing the navigation data and the reference data, in order to calculate position of the diagnostic device with respect to the patient, calculating a route from the position of the diagnostics device to a desired position of the diagnostics device, in accordance with the reference data, providing navigational guidance to the user, and acquiring data relating to the at least one medical examination when the diagnostics device is in the desired position.

In accordance with one example of the presently disclosed subject matter, there is still further provided a method wherein the medical data acquisition guidance includes at least one of the following:
(a) an indication of a check to be performed;
(b) navigational instructions;
(c) operational instructions;
(d) positioning instructions;
(e) examination process instructions.

In accordance with one example of the presently disclosed subject matter, there is yet further provided a method further comprising verifying that the acquired data meets pre-defined standards.

In accordance with one example of the presently disclosed subject matter, there is yet further provided a method wherein the pre-defined standards are at least one of:
(a) the required length of reading;
(b) recorded sound volume;
(c) reading parameters thresholds;
(d) the type of image reading;
(e) the required image reading zoom;
(f) the required image reading light;
(g) the required image reading matching to predefined reference.

In accordance with an aspect of the presently disclosed subject matter, there is still further provided a handheld diagnostics device for performing at least one medical examination, the diagnostics device comprising at least one diagnostics sensor operable to acquire medical data, and a processor, wherein for each of the at least one medical examinations the processor is configured to, in a state of the diagnostics device with respect to a patient in which a respective medical examination enabling condition is not met, provide to a user guidance for changing a state of the diagnostics device with respect to the patient; determine, during the changing of the state of the diagnostics device, fulfillment of the respective medical examination enabling condition based on comparison of acquired data with respective reference data; and operate the at least one diagnostics sensor to acquire respective medical data of the subject when the respective medical examination enabling condition is met.

In accordance with one example of the presently disclosed subject matter, there is still further provided a handheld diagnostics device, wherein the processor is configured to operate the at least one diagnostics sensor to acquire respective medical data of the patient when a first medical examination enabling condition is met and a second medical examination enabling condition is not met, and afterwards to operate the at least one diagnostics sensor to acquire medical data of the patient when the second medical examination enabling condition is met.

In accordance with an aspect of the presently disclosed subject matter, there is provided handheld diagnostics device configured to perform one or more medical examinations of a patient, the diagnostics device comprising:
at least one diagnostics sensor;
at least one navigation sensor; and
a processor;
wherein, for at least one medical examination of the medical examinations, the processor is configured to:
provide reference data indicative of a desired spatial disposition of the diagnostics device with respect to the patient's body for performing the medical examination;
acquire navigation enabling data utilizing the at least one navigation sensor;
determine a spatial disposition of the diagnostics device with respect to the desired spatial disposition, utilizing the acquired navigation enabling data and the reference data;
calculate a required movement correction from the determined spatial disposition to the desired spatial disposition, for acquiring medical data of the patient in accordance with the at least one medical examination;
provide a user with maneuvering instructions to navigate the diagnostics device to the desired spatial disposition in accordance with the calculated route; and
operate the at least one diagnostics sensor to acquire the medical data upon arrival to the desired spatial disposition.

In accordance with one example of the presently disclosed subject matter, there is further provided a handheld diagnostics device wherein the reference data and the navigation enabling data are body or body organ images.

In accordance with one example of the presently disclosed subject matter, there is still further provided a handheld diagnostics device wherein the reference data and the navigation enabling data is Inertial Navigation System (INS) data received from the at least one navigation sensor.

In accordance with one example of the presently disclosed subject matter, there is still further provided a handheld diagnostics device wherein the processor is configured to perform the following steps in order to determine the diagnostics device spatial disposition with respect to the desired spatial disposition:
compare the at least one image with the reference image; and
determine, based on the comparison, the diagnostics device spatial disposition with respect to the desired spatial disposition.

In accordance with one example of the presently disclosed subject matter, there is still further provided a handheld diagnostics device wherein the processor is configured to perform the following steps in order to determine the diagnostics device spatial disposition with respect to the desired spatial disposition:
receive INS data acquired in at least three pre-defined reference points on the patient's body;
determine, based on the received INS data, the diagnostics device spatial disposition with respect to the desired spatial disposition.

In accordance with one example of the presently disclosed subject matter, there is still further provided a handheld diagnostics device wherein the determine is based on triangulation techniques while utilizing the received INS data acquired in at least three pre-defined reference points on the patient's body.

In accordance with one example of the presently disclosed subject matter, there is still further provided a handheld diagnostics device wherein the processor is further configured to transmit the acquired medical data to a remote workstation.

In accordance with one example of the presently disclosed subject matter, there is still further provided a handheld diagnostics device wherein the processor is configured to perform the transmit via a central system.

In accordance with one example of the presently disclosed subject matter, there is still further provided a handheld diagnostics device wherein the central system routes the acquired medical data to available trained personnel.

In accordance with one example of the presently disclosed subject matter, there is still further provided a handheld diagnostics device wherein the processor is further configured to:
  provide the user with one or more questions relating to the patient;
  receive answers to the one or more questions; and
  transmit the answers to the remote workstation.

In accordance with one example of the presently disclosed subject matter, there is still further provided a handheld diagnostics device wherein the reference data is acquired during a calibration process performed by trained personnel.

In accordance with one example of the presently disclosed subject matter, there is still further provided a handheld diagnostics device wherein the processor is further configured to perform the following steps during the calibration process:
  receive an indication of a medical examination to be performed;
  provide the trained personnel with guidance for performing the calibration; and
  upon arrival to the desired diagnostics device spatial disposition, record the reference data indicative of the desired spatial disposition of the diagnostics device with respect to the patient's body.

In accordance with one example of the presently disclosed subject matter, there is still further provided a handheld diagnostics device wherein upon arrival to the desired diagnostics device spatial disposition, the processor is further configured to perform the following additional steps:
  acquire reference medical data; and
  record the acquired reference medical data.

In accordance with one example of the presently disclosed subject matter, there is still further provided a handheld diagnostics device wherein the one or more medical examinations of the patient are defined by a pre-defined check plan associated with the patient.

In accordance with one example of the presently disclosed subject matter, there is still further provided a handheld diagnostics device wherein the diagnostics sensor is an image based diagnostics sensor.

In accordance with one example of the presently disclosed subject matter, there is still further provided a handheld diagnostics device wherein the diagnostics sensor is a sound based diagnostics sensor.

In accordance with one example of the presently disclosed subject matter, there is still further provided a handheld diagnostics device wherein the navigation sensor is a camera.

In accordance with one example of the presently disclosed subject matter, there is still further provided a handheld diagnostics device wherein the navigation sensor is an INS.

In accordance with one example of the presently disclosed subject matter, there is still further provided a handheld diagnostics device wherein the maneuvering instructions are voice instructions provided via a speaker.

In accordance with one example of the presently disclosed subject matter, there is still further provided a handheld diagnostics device wherein the maneuvering instructions are visual instructions provided via a display.

In accordance with one example of the presently disclosed subject matter, there is still further provided a handheld diagnostics device wherein the maneuvering instructions are vibration instructions provided via vibration elements.

In accordance with one example of the presently disclosed subject matter, there is still further provided a handheld diagnostics device wherein the processor is further configured to verify that the acquired data meets pre-defined standards.

In accordance with one example of the presently disclosed subject matter, there is still further provided a handheld diagnostics device wherein the pre-defined standards are at least one of:
  (a) a required length of reading;
  (b) a minimal recorded sound volume;
  (c) a minimal recorded sound quality;
  (d) a minimal pressure against the patient's body;
  (e) a maximal pressure against the patient's body;
  (f) a maximal allowed movement of the diagnostics device during acquisition of readings;
  (g) a type of image reading;
  (h) a required image reading zoom;
  (i) a required image reading light;
  (j) a required image reading matching to predefined reference; and
  (k) a minimal image quality.

In accordance with one example of the presently disclosed subject matter, there is still further provided a handheld diagnostics device wherein the reference data is generic reference data.

In accordance with one example of the presently disclosed subject matter, there is still further provided a handheld diagnostics device wherein the processor is further configured to automatically identify the patient.

In accordance with an aspect of the presently disclosed subject matter, there is still further provided a method for performing one or more medical examinations of a patient using a diagnostics device, wherein for at least one medical examination of the medical examinations, the method comprising:
  providing reference data indicative of a desired spatial disposition of the diagnostics device with respect to the patient's body for performing the medical examination;
  operating the diagnostics device for acquiring navigation enabling data;
  determining a spatial disposition of the diagnostics device with respect to the desired spatial disposition, utilizing the acquired navigation enabling data and the reference data;
  calculating a required movement correction from the determined spatial disposition to the desired spatial disposition, for acquiring medical data of the patient in accordance with the at least one medical examination;
  providing a user with maneuvering instructions to navigate the diagnostics device to the desired spatial disposition in accordance with the calculated route; and
  acquiring the medical data upon arrival to the desired spatial disposition.

In accordance with one example of the presently disclosed subject matter, there is still further provided a method wherein the reference data and the navigation enabling data are body or body organ images.

In accordance with one example of the presently disclosed subject matter, there is still further provided a method wherein the reference data and the navigation enabling data is Inertial Navigation System (INS) data received from the at least one navigation sensor.

In accordance with one example of the presently disclosed subject matter, there is still further provided a method wherein the determining comprises:
  comparing the navigation enabling data with the reference data; and
  determining, based on the comparing, the diagnostics device spatial disposition with respect to the desired spatial disposition.

In accordance with one example of the presently disclosed subject matter, there is still further provided a method wherein the determining comprises:
  receiving INS data acquired in at least three pre-defined reference points on the patient's body;
  determining, based on the received INS data and the reference data, the diagnostics device spatial disposition with respect to the desired spatial disposition.

In accordance with one example of the presently disclosed subject matter, there is still further provided a method wherein the determining is based on triangulation techniques while utilizing the received INS data acquired in at least three pre-defined reference points on the patient's body.

In accordance with one example of the presently disclosed subject matter, there is still further provided a method further comprising transmitting the acquired medical data to a trained personnel workstation.

In accordance with one example of the presently disclosed subject matter, there is still further provided a method wherein the transmitting is performed via a central system.

In accordance with one example of the presently disclosed subject matter, there is still further provided a method wherein the central system routes the acquired medical data to available trained personnel.

In accordance with one example of the presently disclosed subject matter, there is still further provided a method further comprising:
  providing the user with one or more questions relating to the patient;
  receiving answers to the one or more questions; and
  transmitting the answers to the trained personnel.

In accordance with one example of the presently disclosed subject matter, there is still further provided a method wherein the reference data is acquired during a calibration process performed by trained personnel.

In accordance with one example of the presently disclosed subject matter, there is still further provided a method wherein the calibration process comprises:
  receiving an indication of a medical examination to be performed;
  providing the trained personnel with guidance for performing the calibration; and
  upon arrival to the desired diagnostics device spatial disposition, recording the reference data indicative of the desired spatial disposition of the diagnostics device with respect to the patient's body.

In accordance with one example of the presently disclosed subject matter, there is still further provided a method wherein upon arrival to the desired diagnostics device spatial disposition, the method further comprises:
  acquiring reference medical data; and
  recording the acquired reference medical data.

In accordance with one example of the presently disclosed subject matter, there is still further provided a method wherein the one or more medical examinations of the patient are defined by a pre-defined check plan associated with the patient.

In accordance with one example of the presently disclosed subject matter, there is still further provided a method wherein the maneuvering instructions are voice instructions provided via a speaker.

In accordance with one example of the presently disclosed subject matter, there is still further provided a method wherein the maneuvering instructions are visual instructions provided via a display.

In accordance with one example of the presently disclosed subject matter, there is still further provided a method wherein the maneuvering instructions are vibration instructions provided via vibration elements.

In accordance with one example of the presently disclosed subject matter, there is still further provided a method further comprising verifying that the acquired data meets pre-defined standards.

In accordance with one example of the presently disclosed subject matter, there is still further provided a method wherein the pre-defined standards are at least one of:
  (a) a required length of reading;
  (b) a minimal recorded sound volume;
  (c) a minimal recorded sound quality;
  (d) a minimal pressure against the patient's body;
  (e) a maximal pressure against the patient's body;
  (f) a maximal allowed movement of the diagnostics device during acquisition of readings;
  (g) a type of image reading;
  (h) a required image reading zoom;
  (i) a required image reading light;
  (j) a required image reading matching to predefined reference.

In accordance with one example of the presently disclosed subject matter, there is still further provided a method wherein the reference data is generic reference data.

In accordance with one example of the presently disclosed subject matter, there is still further provided a method further comprising automatically identifying the patient.

In accordance with an aspect of the presently disclosed subject matter, there is still further provided a handheld diagnostics device configured to perform one or more medical examinations of a patient, the diagnostics device comprising:
  at least one diagnostics sensor;
  at least one navigation sensor; and
  a processor;
  wherein, for at least one medical examination of the medical examinations, the processor is configured to:
  provide reference data indicative of a desired spatial disposition of a pointing object with respect to the patient's body for performing the medical examination;
  receive navigation enabling data from the at least one navigation sensor;
  determine a spatial disposition of the pointing object with respect to the desired spatial disposition, utilizing the data received from the at least one navigation sensor and the reference data;
  calculate a required movement correction from the determined spatial disposition to the desired spatial disposition, for acquiring medical data of the patient in accordance with the at least one medical examination;
  provide a user with maneuvering instructions to navigate the pointing object to the desired spatial disposition in accordance with the calculated required movement correction;

instruct the user to move the diagnostics device to the location indicated by the pointing object upon arrival of the pointing object to the desired spatial disposition; and operate the at least one diagnostics sensor to acquire the medical data.

In accordance with an aspect of the presently disclosed subject matter, there is still further provided a method for performing one or more medical examinations of a patient using a diagnostics device, wherein for at least one medical examination of the medical examinations, the method comprising:

providing reference data indicative of a desired spatial disposition of a pointing object with respect to the patient's body for performing the medical examination;

operating the diagnostics device for acquiring navigation enabling data;

determining a spatial disposition of the pointing object with respect to the desired spatial disposition, utilizing the acquired navigation enabling data and the reference data;

calculating a required movement correction from the determined spatial disposition to the desired spatial disposition, for acquiring medical data of the patient in accordance with the at least one medical examination;

providing a user with maneuvering instructions to navigate the pointing object to the desired spatial disposition in accordance with the calculated required movement correction;

instructing the user to move the diagnostics device to the location indicated by the pointing object upon arrival of the pointing object to the desired spatial disposition; and operating the at least one diagnostics sensor to acquire the medical data.

BRIEF DESCRIPTION OF THE DRAWINGS

In order to understand the presently disclosed subject matter and to see how it may be carried out in practice, the subject matter will now be described, by way of non-limiting examples only, with reference to the accompanying drawings, in which:

FIG. 8a is a flowchart illustrating an example of a sequence of operations carried out for recording reference data during personalized calibration of a diagnostic device, using imaging and orientation sensors, in accordance with the presently disclosed subject matter;

DETAILED DESCRIPTION

Figure 1:
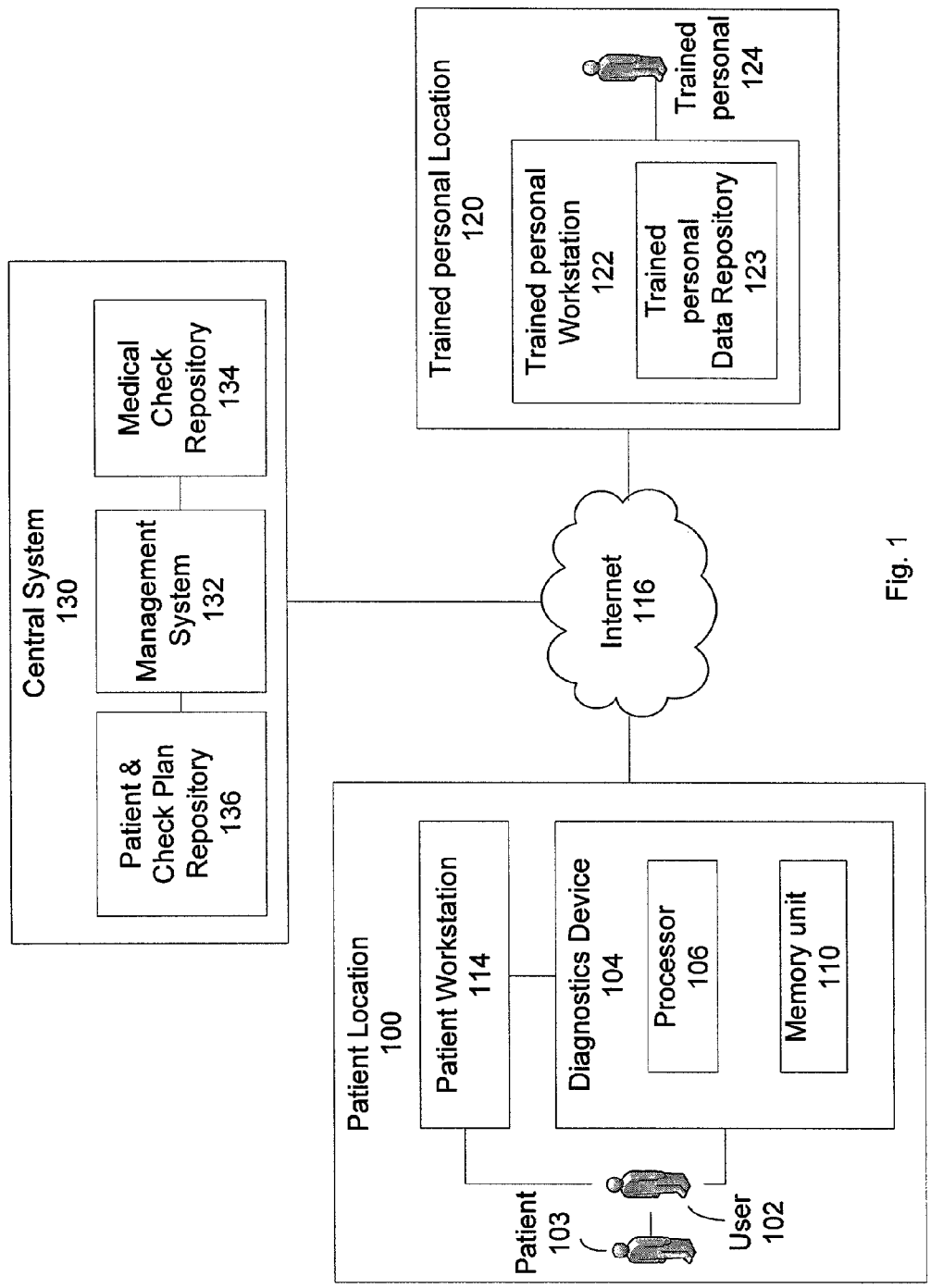
FIG. 1 is a block diagram schematically illustrating one example of a system for performing an automatic and self-guided medical examination, in accordance with the presently disclosed subject matter.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "receiving", "transmitting", "determining", "recording", "operating", "comparing", "identifying", "performing", "instructing", "utilizing", "calculating", "providing", "acquiring", "verifying" or the like, include action and/or processes of a computer that manipulate and/or transform data into other data, said data represented as physical quantities, e.g. such as electronic quantities, and/or said data representing the physical objects. The term "computer" should be expansively construed to cover any kind of electronic device with data processing capabilities, including, by way of non-limiting example, a personal computer, a server, a computing system, a communication device, a processor (e.g. digital signal processor (DSP), a microcontroller, a field programmable gate array (FPGA), an application specific integrated circuit (ASIC), etc.), any other electronic computing device, and or any combination thereof.

The operations in accordance with the teachings herein may be performed by a computer specially constructed for the desired purposes or by a general purpose computer specially configured for the desired purpose by a computer program stored in a computer readable storage medium.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the example(s) is included in at least one example of the presently disclosed subject matter. Thus the appearance of the phrase "one case", "some cases", "other cases" or variants thereof does not necessarily refer to the same example(s).

It is appreciated that certain features of the presently disclosed subject matter, which are, for clarity, described in the context of separate examples, may also be provided in combination in a single example. Conversely, various features of the presently disclosed subject matter, which are, for brevity, described in the context of a single example, may also be provided separately or in any suitable sub-combination.

According to examples of the presently disclosed subject matter one or more stages illustrated in the figures may be executed in a different order and/or one or more groups of stages may be executed simultaneously and vice versa. The figures illustrate a general schematic of the system architecture in accordance with some examples of the presently disclosed subject matter. Each module in the figures can be made up of any combination of software, hardware and/or firmware that performs the functions as defined and explained herein. The modules in the figures may be centralized in one location or dispersed over more than one location.

Bearing this in mind, attention is drawn to FIG. 1, a block diagram schematically illustrating one example of a system for performing an automatic and self-guided medical examination, in accordance with the presently disclosed subject matter. It can be appreciated that user 102 and patient 103 are located at patient location 100. User 102 can in some cases be patient 103 whose medical examination is required (in such cases, even though user 102 and patient 103 are shown as separate entities in the drawings, they are in fact the same entity). In other cases, user 102 can be a person that will be performing the medical examination of patient 103.

For the purpose of performing a medical examination, user 102 operates a diagnostic device 104, as further detailed below. In some cases, user 102 also operates a patient workstation 114, as further detailed below. Patient workstation 114 can be any computer, including a personal computer, a portable computer, a cellular handset or an apparatus with appropriate processing capabilities, including a computer and/or an apparatus which can be, for example, specifically configured for that purpose. It is to be noted that in some cases, patient workstation 114 can be incorporated within diagnostics device 104. Diagnostics device 104 comprises (or is otherwise associated with) at least one processor 106 (e.g. digital signal processor (DSP), a microcontroller, a field programmable gate array (FPGA), an application specific integrated circuit (ASIC), etc.) and a memory unit 110 (e.g. ROM, hard disk, etc.). Processor 106 is configured to receive instructions and control the components and operations of diagnostics device 104.

In some cases diagnostics device 104 can be configured to communicate with patient workstation 114. The communication between diagnostics device 104 and patient workstation 114 can be realized by any communication means, e.g. via wired or wireless communication. It can be noted that user 102, patient 103, diagnostics device 104 and patient workstation 114 are located at patient location 100.

Diagnostics device 104 can be configured to acquire various data as further detailed below. The acquired data can be transmitted (directly from diagnostics device 104 or through patient workstation 114) to trained personnel workstation 122 located at trained personnel location 120 and/or to central system 130. Central system 130 and trained personnel workstation 122 can be any computer, including a personal computer, a portable computer, a cellular handset or an apparatus with appropriate processing capabilities, including a computer and/or an apparatus which can be, for example, specifically configured for that purpose. The acquired data can be transmitted for example via Internet 116. It is to be noted that the data can be transmitted while utilizing other known communication alternatives, such as a cellular network, VPN, LAN, etc.

Central system 130 comprises patient & check plan repository 136 in which various data relating to the patient is maintained. Such data can include, for example, patient identification number, patient name, patient age, patient contact details, patient medical data (such as diseases, sensitivities to medicines, etc.), check plans data (as further detailed below), etc. Central system 130 can further comprise a medical examination repository 134 in which data acquired by diagnostics device 104 and patient workstation 114 is maintained. Such data can include, for example, results of medical examinations performed using diagnostics device (such as ear readings, lungs or heart recorded sound, blood pressure, body temperature, etc. as further detailed below). Central system 130 further comprises management system 132 configured to forward received data to a selected trained personnel workstation 122 (for example an available trained personnel workstation 122 or trained personnel workstation 122 with the shortest queue). It is to be noted that when providing a central system, there may be more than one trained personnel location 120 and trained personnel 124 as central system 130 allows for a distributed approach in which data can be received by the central system 130 from multiple patient locations and transferred by it to multiple trained personnel locations. Thus, in case the transmitted data is received at central system 130, the data is saved in medical examination repository 134 and management system 132 can transmit the received data to trained personnel location 120 (e.g. via Internet 116. It is to be noted that the data can be transmitted while utilizing other known alternatives, such as a cellular network, VPN, LAN, etc.). In some cases, management system 132 can also manage other processes such as, subscribing patients, planning scheduling of patients to available trained personnel, etc.

It is to be noted that central system 130 is optional to the solution and that central system 130 can be part of the trained personnel system 120, In addition the communication between the patient location 100 to the trained personnel location 120 can be implemented directly without the use of or need for a central system 130.

When the transmitted data is received at trained personnel workstation 122, the data can be saved in trained personnel data repository 123 that can be connected to trained personnel workstation 122. A trained personnel 124 (e.g. a doctor, a nurse, a medic, etc., including any other person with the know-how and skill to acquire and/or analyze medical data), located at trained personnel location 120, can retrieve and review the acquired data, for example using trained personnel workstation 122. It is to be noted that patient workstation 114, trained personnel workstation 122 and central system 130 can include a display (e.g. LCD screen), and a keyboard or any other suitable input/output devices. In some cases, trained personnel 124 can provide feedback to user 102, for example by transmitting data back to patient workstation 114. Such feedback can include, for example, analysis of the received data, request to receive more data, medical treatment instructions, invitation to further examination, etc. Alternatively or additionally, trained personnel 124 can transmit feedback data to central system 130, which, in turn, can transmit the feedback data to patient workstation 114 (e.g. via the Internet, cellular network, etc.).

Figure 2:
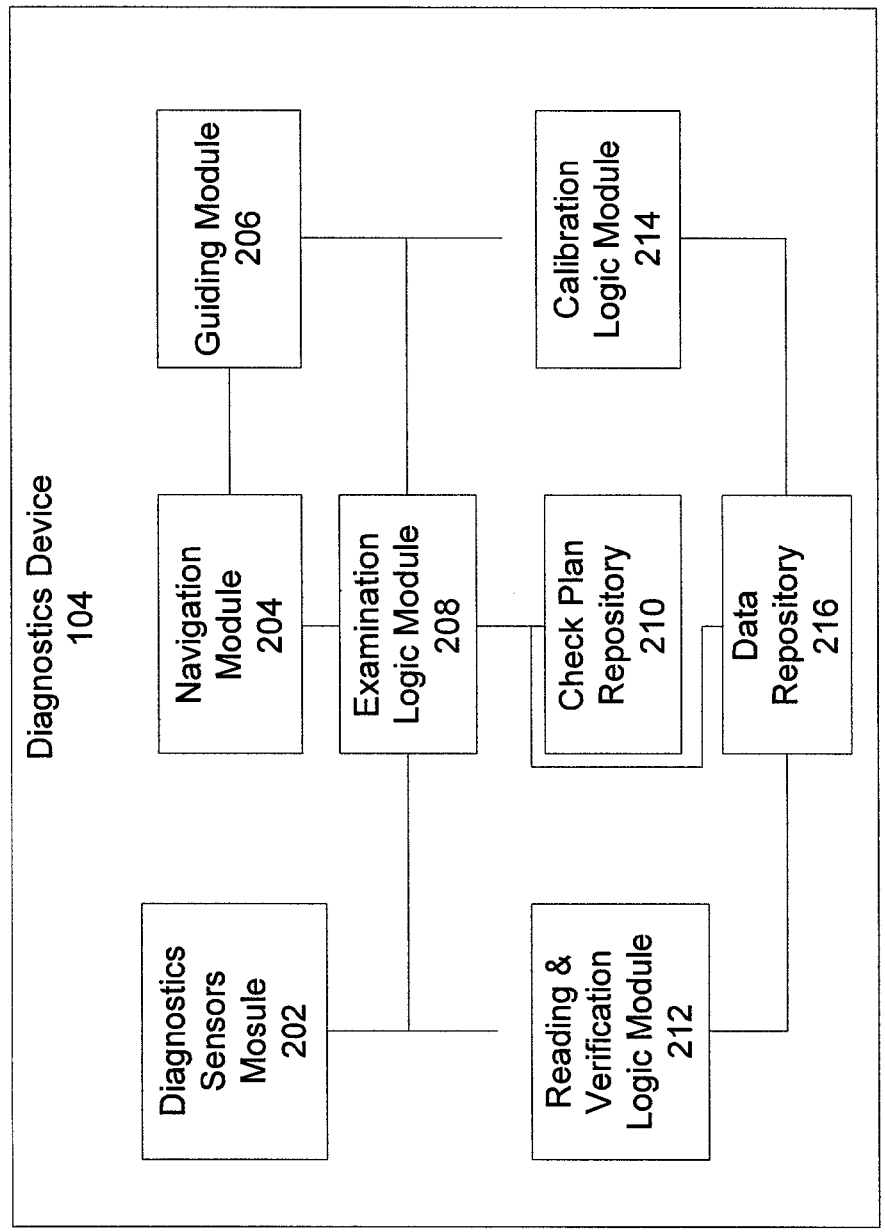
FIG. 2 is a block diagram schematically illustrating one example of a diagnostic device configured to perform an automatic and self-guided medical examination, in accordance with the presently disclosed subject matter.

FIG. 2 is a block diagram schematically illustrating one example of a diagnostic device configured to perform an automatic and self-guided medical examination, in accordance with the presently disclosed subject matter. Diagnostics device 104 can comprise inter alia, diagnostic sensors module 202, guiding module 206, examination logic module 208, check plan repository 210 and data repository 216. Diagnostics device can further comprise navigation module 204, reading and verification logic module 212 and calibration logic module 214.

Examination logic module 208 can be responsible for operating diagnostics device 104 for performing a medical examination of patient 103. Diagnostics device 104 can be activated for example by User 102. Upon activation, user 102 can optionally indicate the patient to be checked. Such indication can be in the form of inputting patient 103 identification details (e.g. patient id, patient name, etc.), for example in patient workstation 114. In other cases such indication can be in the form of selecting a specific patient 103, for example from a list of known patients. Such list of known patients can be displayed on patient workstation 114. In some cases, such list of known patients can be displayed on a display connected to diagnostics device 104. Details of known patients to be presented on such list of known patients can be retrieved, for example, from one or more of: data repository 216, check plan repository 210, trained personnel data repository 123, patient & check plan repository 136 or any other location operatively connected to diagnostics device 104 on which patient data is stored. In further cases diagnostic device 104 can automatically identify patient 103 by using methods of body identification such as face recognition, fingerprint reading or any other mean of biometric identification. Such automatic identification can utilize, for example, navigation camera 420 or any other peripheral, reader or sensor connected to diagnostic device 104 or to patient workstation 114 that enable acquiring data relevant to the automatic identification. It is to be noted that other methods of indicating or identifying a patient to be checked can be utilized as well.

In some cases, after receiving patient 103 details, examination logic module 208 can be configured to retrieve data relating to a check plan. Such check plan data can be stored on one or more of: check plan repository 210, patient & check plan repository 136, trained personnel data repository 123 or any other location operatively connected to diagnostics device 104 on which patient specific check plan data can be stored. A check plan can define a series of medical examinations and data to be acquired by diagnostics device 104. Such medical data acquisition can be performed by user 102 on patient 103. The medical data can include, for example, body temperature, blood pressure, pulse, respiratory rate, throat image, mole image, ear image, etc. The check plan can in some cases be a generic check plan (e.g. a series of medical examinations that can be standard pre-determined medical examinations). In other cases the check plan can be defined according to a certain medical condition of patient 103 (e.g. a check plan for patients with cancer can comprise a series of cancer specific required medical examinations, a check plan for patients with high blood pressure can comprise a series of high blood pressure specific required medical examinations, etc.). In further cases, the check plan can be specifically defined for patient 103, for example according to a trained personnel 124 decision (e.g. a physician interested in monitoring specific medical data of a specific patient can decide upon a patient specific check plan). The check plan can include information, inter alia about the examination process, steps and logic, and predefined reading parameters such as type of sensor to be used (still image vs. video), required length of reading (sound or video recording) in terms of time (e.g. seconds), and reading data thresholds (for example definition of acceptable minimal and/or maximal reading limits to be used as a quality parameter of a reading.

Upon retrieval of the check plan to be performed, examination logic module 208 can be configured to utilize navigation module 204 in order to enable determination of current diagnostics device spatial disposition with respect to patient's 103 body (or a specific part thereof).

It is to be noted that the term spatial disposition or the like can relate to spatial distances, spatial angles (including orientations), or any other spatial reference that is used for characterizing a spatial relationship between two objects, e.g. between diagnostics device 104 and patient's 103 body (or a specific part thereof).

Navigation module 204 can be responsible for the operation of various sensors utilized for that purpose, as further detailed below with reference to FIG. 4. Navigation module 204 can utilize pre-stored reference data for establishing data about diagnostics device 104 current and desired spatial dispositions with respect to patient's 103 body (or a specific part thereof). The pre-stored reference data can consist of image based reference data and/or diagnostics device 104 spatial disposition based reference data, or any other relevant reference data, including data that can be read by diagnostics device 104 navigation module 204 or diagnostic sensors 202, as further detailed below, inter alia with respect to FIGS. 6, 9 and 10-13. The reference data can be for example images of patient 103 (external patient images and/or internal patient images of internal body parts), general organ images, device coordinates, data of relativity between spatial dispositions with respect to patient's 103 body (or a specific part thereof), etc. Such pre-stored reference data can be stored on patient & check plan repository 136, trained personnel data repository 123 or any other location operatively connected to diagnostics device 104 on which image based reference data is stored. Upon establishment of diagnostics device 104 current spatial disposition with respect to patient's 103 body (or a specific part thereof), navigation module can calculate a route to a desired diagnostics device 104 spatial disposition with respect to patient's 103 body (or a specific part thereof), that can be defined, for example, by the patient specific check plan. The route calculation can be performed continuously or periodically (e.g. every pre-determined time interval), for example until arrival to the desired diagnostics device 104 spatial disposition with respect to patient's 103 body (or a specific part thereof), as further detailed below, inter alia with reference to FIGS. 6 and 11-13.

In some cases, examination logic module 208 can be configured to utilize guiding module 206 in order to provide various guidance data instructing user 102 how to maneuver diagnostics device 104 to the desired diagnostics device 104 spatial disposition with respect to patient's 103 body (or a specific part thereof). Such guidance data can include, inter alia, voice commands, image display, diagnostics device 104 vibrations, etc., as further detailed below, inter alia with reference to FIGS. 5, 6 and 11-13. Such guidance data can be presented to user 102 continuously or periodically (e.g. every pre-determined time interval), until diagnostics device 104 arrives at the desired spatial disposition with respect to patient's 103 body (or a specific part thereof) from which the medical examination can be performed. Such guidance data can be calculated according to the respective calculation of a route to the desired diagnostics device 104 spatial disposition with respect to patient's 103 body (or a specific part thereof), as calculated by navigation module 204.

Upon arrival to the desired diagnostics device 104 spatial disposition with respect to patient's 103 body (or a specific part thereof), for example as indicated by the patient specific check plan, examination logic module 208 can be configured to utilize reading and verification logic module 212 in order to acquire medical data of patient 103. Upon arrival to desired diagnostics device 104 spatial disposition with respect to patient's 103 body (or a specific part thereof), reading and verification module 212 can be configured to verify that diagnostics device 104 is located at the desired spatial disposition with respect to patient's 103 body (or a specific part thereof) when acquiring medical data of patient 103, as further detailed below, inter alia with reference to FIG. 14. Reading and verification module 212 can be further configured to instruct diagnostics sensor module 202 to prepare to acquire medical data of patient 103, and to perform acquisition of such medical data, as further detailed below, inter alia with reference to FIG. 14. After acquisition of medical data of patient, reading and verification module 212 can be configured to verify that the acquired data meets pre-defined standards (e.g. a required length of reading, reading data thresholds, etc.), as further detailed below, inter alia with reference to FIG. 14. In case the acquired data does not meet the pre-defined standards, diagnostics device 104 can in some cases be configured to instruct user 102 to perform the required repositioning and reorienting thereof in order to bring diagnostics device 104 to the desired spatial disposition with respect to patient's 103 body (or a specific part thereof). Following repositioning and reorienting of diagnostics device 104, reading and verification logic module 212 can be configured to retry acquiring the medical data of patient 103, as further detailed below, inter alia with reference to FIG. 14.

Diagnostics device 104 can be further configured to utilize diagnostics sensor module 202 that can be configured to acquire medical data of patient 103. Diagnostics sensor module 202 can be responsible for the operation of various sensors used for acquiring various medical data of patient 103. Such medical data of patient 103 can be used for example for diagnostics by trained personnel 124. Diagnostics sensor module 202 is further discussed below, inter alia with reference to FIG. 3.

In some cases, diagnostics device 104 can further comprise a calibration logic module 214. Calibration logic module 214 can be configured, inter alia, to acquire reference data relating to medical examinations of patient 103, as further detailed below, for example with reference to FIG. 7. In some cases, the reference data is acquired by diagnostics device 104 during an initial calibration performed by trained personnel 124. For example, a physician can perform a medical examination of patient 103 and diagnostics device 104 can, for example, record the medical examination performed by trained personnel 124, including the acquired medical data, as further detailed below, for example with reference to FIG. 7. The recorded data, including the acquired medical data, can be stored, for example, on one or more of: check plan repository 210, patient & check plan repository 136, trained personnel data repository 123 or any other location operatively connected to diagnostics device 104 on which data relating to patient 103 can be stored.

It is to be noted that diagnostics device 104 can further comprise data repository 216. Data repository 216 can be configured to store various data, including, inter alia, data relating to one or more patients and various medical data thereof (e.g. data acquired during a medical examination of the patients), as further detailed below.

In some cases, diagnostics device can further comprise check plan repository 210. Check plan repository 210 can be configured to store various data, including, inter alia, data relating to patient specific check plans, as further detailed below.

Figure 3:
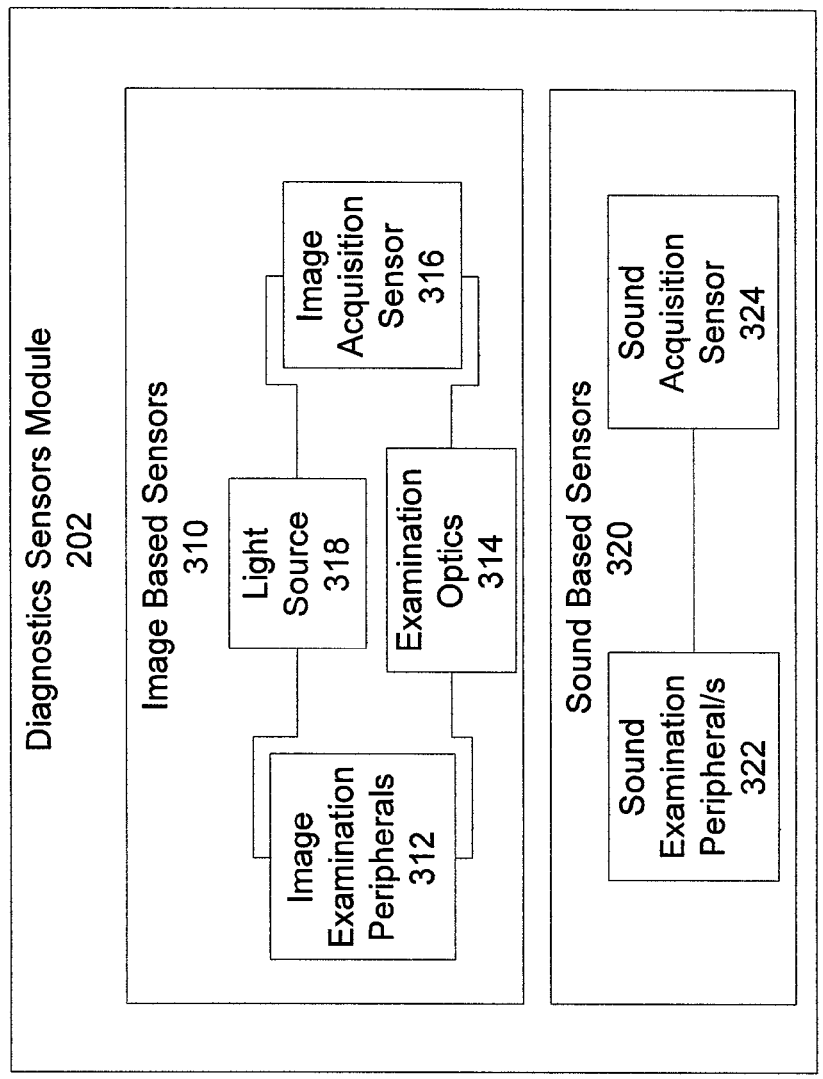
FIG. 3 is a block diagram schematically illustrating an example of diagnostic sensors configured to acquire medical data, in accordance with the presently disclosed subject matter.

FIG. 3 is a block diagram schematically illustrating an example of diagnostic sensors configured to acquire medical data, in accordance with the presently disclosed subject matter. Diagnostics sensors module 202 can include, inter alia, image based sensors 310, sound based sensors 320, as well as other sensors not shown in the drawing. Diagnostic sensors 202 can be designed for taking a specific organ reading (such as ear image reading (e.g. Otoscope)) and general organ readings (such as external skin reading, eye reading, etc.). Diagnostic sensors 202 can be modular e.g. some sensors can be attached/detached to diagnostic device 104, in accordance with the required medical examination.

Image based sensors 310 can include one or more light sources 318. Light sources 318 can be Light Emitting Diodes, or any other light source known in the art. Light sources 318 can be utilized for example to light the areas of which an image is to be acquired in order to provide for sufficient image quality (e.g. a quality that will enable image analysis by trained personnel 124).

Image based sensors 310 can further include image examination peripherals 312. Image examination peripherals 312 can include, inter alia, various components that enable safe access to various body parts, such as a human ear, throat, etc. Such components can be, for example, made of plastic and can be attached to diagnostics device 104. Such components can, for example, have a generic physical structure that fits various body parts regardless of the fact that different people, at different ages, have different body parts structure (e.g. a child has a smaller ear than a grown person and the image examination peripherals 312 can be designed to fit substantially any ear structure, etc.). Image examination peripherals 312 can aid user 102 in positioning the diagnostics device 104 in the desired spatial disposition with respect to patient's 103 body (or a specific part thereof) so that acquisition of image based medical data can be performed.

Image based sensors 310 can further include image acquisition sensor 316. Image acquisition sensor 316 can be, inter alia, a camera (e.g. a still camera, a video camera, etc.), or any other device capable of acquiring an image. Image acquisition sensor 316 can be based on standard sensors such as CMOS or CCD or any other applicable sensor known in the art. Image acquisition sensor 316 can be designed to fit image acquisition of multiple body parts or organs, regardless of size or distance (e.g. it can have the required resolution and/or size and/or light sensitivity to fit multiple body parts or organ readings). It is to be noted that image acquisition sensor 316 can be the same sensor as the navigation image acquisition sensor and vice versa.

Image based sensors 310 can further include examination optics 314. Examination optics 314 can be, for example, camera lenses. Examination optics 314 can be designed to fit various wavelengths, field depth, wide or narrow lens angle, etc. and therefore can fit various types of image readings as well as various types of organ sizes and structures. Examination optics 314 enable image acquisition sensor 316 to acquire image based medical data, having the required properties (e.g. examination optics 314 should enable acquisition of an image that covers the entire area that is required for analysis by trained personnel 124, etc.). In some cases, data acquired from examination optics 314 and image acquisition sensor 316 can be later analyzed and/or transformed and/or aligned to fit the specific required organ area reading (e.g. in order to fit a quality analysis by trained personnel 124, the specific required image area can be cut of the entire image or can be aligned using image analysis and or image transformation or manipulation techniques and/or algorithms known in the art).

Sound based sensors 320 can include one or more sound acquisition sensors 324. Sound acquisition sensors 324 can be, for example, a microphone, or any other device capable of acquiring sound data. Sound acquisition sensors 324 can fit multiple sound frequencies that can be adjusted to fit recording of specific organ sound (as, for example, heart sound frequencies are different than lung sound frequencies). Sound acquisition sensors 324, can also include various abilities to assist acquiring a quality sound such as noise cancellation filters, etc.

Sound based sensors 320 can further include sound examination peripherals 322. Sound examination peripherals 322 can include, inter alia, various components that enable easy fit, comfortable adjustment and safe access to various body parts, such as a human chest, stomach, lung, etc. Such components can be, for example, made of plastic, rubber, etc. and can be attached to diagnostics device 104. Such components can, for example, have a generic physical structure that fits various body parts regardless of the fact that different people, at different ages, have different body parts structure (e.g. a child has a smaller chest than a grown person and the sound examination peripherals 322 can be designed to fit substantially any chest structure, etc.). Sound examination peripherals 322 can aid user 102 in positioning diagnostics device 104 in the desired spatial disposition with respect to patient 103 body (or a specific part thereof) in a way that will enable acquisition of sound based medical data (e.g. allow minimizing any external noise that can interfere with the sound acquisition).

Figure 4:
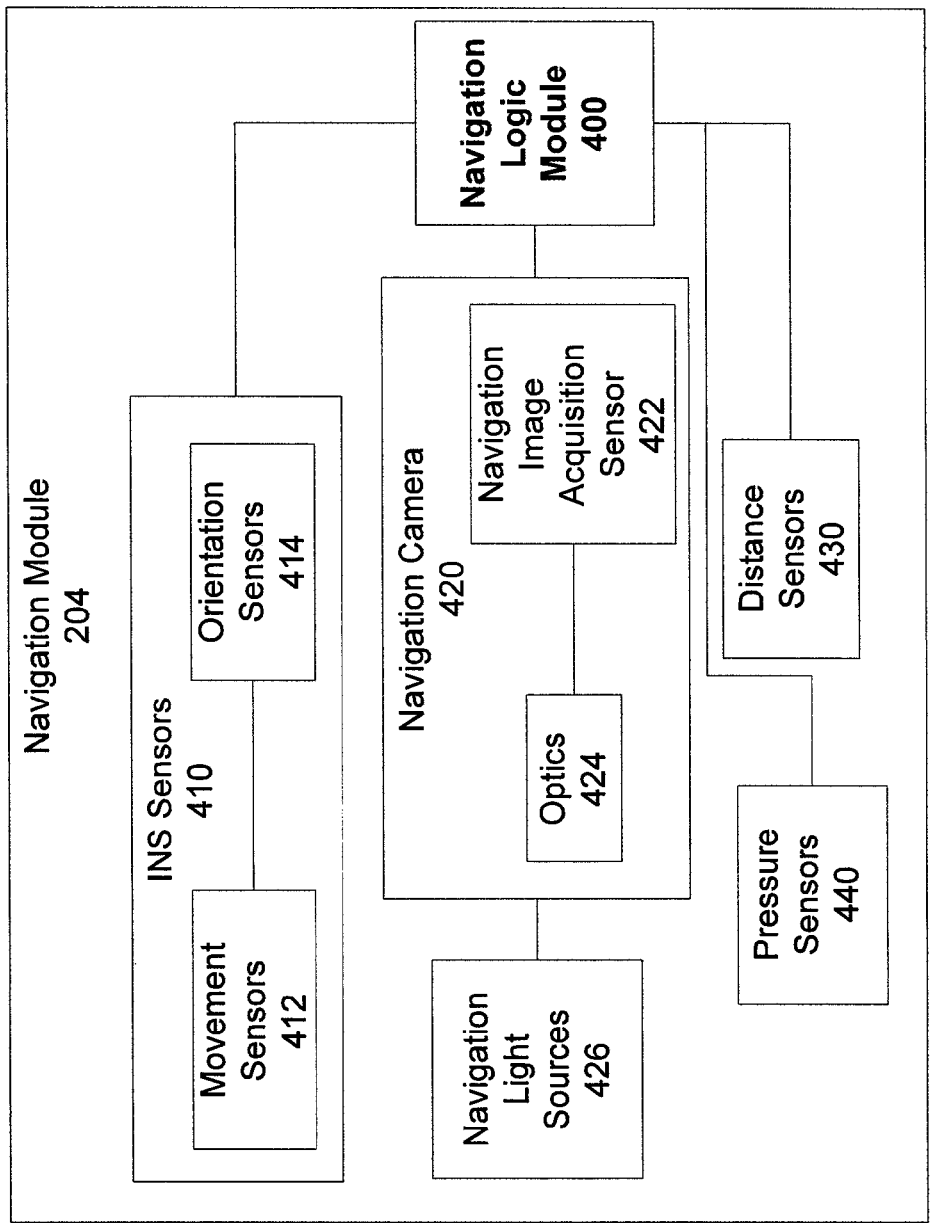
FIG. 4 is a block diagram schematically illustrating an example of a navigation module configured to calculate the spatial disposition of the diagnostic device with respect to patient's body (or a specific part thereof), in accordance with the presently disclosed subject matter.

FIG. 4 is a block diagram schematically illustrating an example of a navigation module configured to calculate the spatial disposition of the diagnostic device with respect to patient's body (or a specific part thereof), in accordance with the presently disclosed subject matter. Navigation module 204 can comprise navigation logic module 400. Navigation logic module 400 can be configured to determine current diagnostics device 104 spatial disposition with respect to patient's 103 body, and to calculate a route to a desired diagnostics device 104 spatial disposition with respect to patient's 103 body (or a specific part thereof), as further detailed below, inter alia with respect to FIGS. 6, 9 and 10-13. For that purpose, navigation logic module 400 can be configured to utilize navigation sensors such as Inertial Navigation System (INS) sensors 410 (for example IMUs—Inertial Measurement Units) and/or navigation camera 420, etc. INS sensors 410 can include movement sensors 412 (such as accelerometers sensors, etc.) capable of acquiring data relating to the movement of diagnostics device 104 and orientation sensors 414 (such as gyroscope sensors, etc.) capable of acquiring data relating to the orientation of diagnostics device 104. Navigation logic module 400 can use the raw INS sensors data to calculate the exact movement and orientation of the device with respect to patient's 103 body and also include the required logic to eliminate sensors calibration errors using techniques and algorithms known the art. Thus, in some cases, navigation can be based on INS data alone. It is to be noted that navigation based on INS data alone requires substantially no movement of patient 103 during the medical examination, as such movement may result in deviations that will prevent accurate acquisition of medical data.

Navigation module 204 can further comprise navigation camera 420. Navigation camera 420 can comprise a navigation image acquisition sensor 422 configured to acquire an image of patient 103 body and can further comprise optics 424. Optics 424 can be, for example, camera lenses. Optics 424 can have various wavelengths, field depth, wide or narrow lens angle, etc. Optics 424 enable navigation camera 420 to acquire image data, having the required properties for enabling navigation of diagnostics device 104. Navigation camera 420 can be used to acquire relevant body and/or organ images that navigation logic module 400 can utilize in order to identify current spatial disposition of diagnostics device 104 with respect to patient's 103 body (or a specific part thereof). This calculation can be done, for example, by comparing an image acquired (e.g. in real time or near real time) from the navigation camera 420 to a set of reference images that can be stored, for example, on check plan repository 210. When a specific image element is found in one of the reference images (as further described, inter alia with respect to FIG. 9), navigation logic module 400 can be configured to perform image matching (for example by utilizing known techniques) to analyze diagnostics device 104 relative position therefrom, and use that match to define the current diagnostics device 104 spatial disposition as a temporary "origin point" to be used as a synchronization point for calculating the required route to the desired diagnostic device 104 spatial disposition, as further detailed below, for example with reference to FIGS. 9 and 10. It is to be noted that in some cases navigation can be based on image data alone, as diagnostics device 104 can be configured to continuously or periodically (e.g. every pre-determined time interval) compare the image acquired by navigation camera 420 to reference images (e.g. reference images saved for example on check plan repository 210) and once a match is found diagnostics device 104 can be configured to calculate the current device spatial disposition with respect to the patient's 103 body (or a specific part thereof), by comparing the image acquired by navigation camera 420 with the saved reference image. This calculation can be done for example, by using image and image pattern comparison and transformation techniques as known in the art. Based on the calculation of the diagnostics device 104 spatial disposition with respect to the patient's 103 body (or a specific part thereof), diagnostics device 104 can be configured to calculate the required route to the desired diagnostic device 104 spatial disposition with respect to the patient's 103 body (or a specific part thereof), as further detailed below, for example with reference to FIGS. 9 and 10. Once diagnostics device 104 identifies that it has reached the desired spatial disposition with respect to the patient's 103 body (or a specific part thereof), it can alert the user not to move until the required image is acquired.

Navigation module 204 can further comprise one or more navigation light sources 426. Navigation light sources 426 can be Light Emitting Diodes, or any other light source known in the art.

Navigation module 204 can further comprise distance sensors 430. Distance sensors 430 can be for example a laser distance sensor, as known in the art, or any other sensor that can determine distance of diagnostics device 104 from an object (e.g. patient 103 body, or a specific part thereof). Navigation logic module 400 can utilize data received from distance sensors 430 in order to calculate the spatial disposition of diagnostics device with respect to patient's 103 body (or a specific part thereof).

Navigation module 204 can further comprise pressure sensors 440. Pressure sensors 430 can be a known in the art pressure sensor that can determine the amount of pressure exerted on diagnostics device 104 as it is pressed against an object (e.g. patient 103 body or a specific part thereof). Navigation logic module 400 can utilize data received from pressure sensors 440 in order to calculate the spatial disposition of diagnostics device with respect to patient's 103 body (or a specific part thereof).

Figure 5:
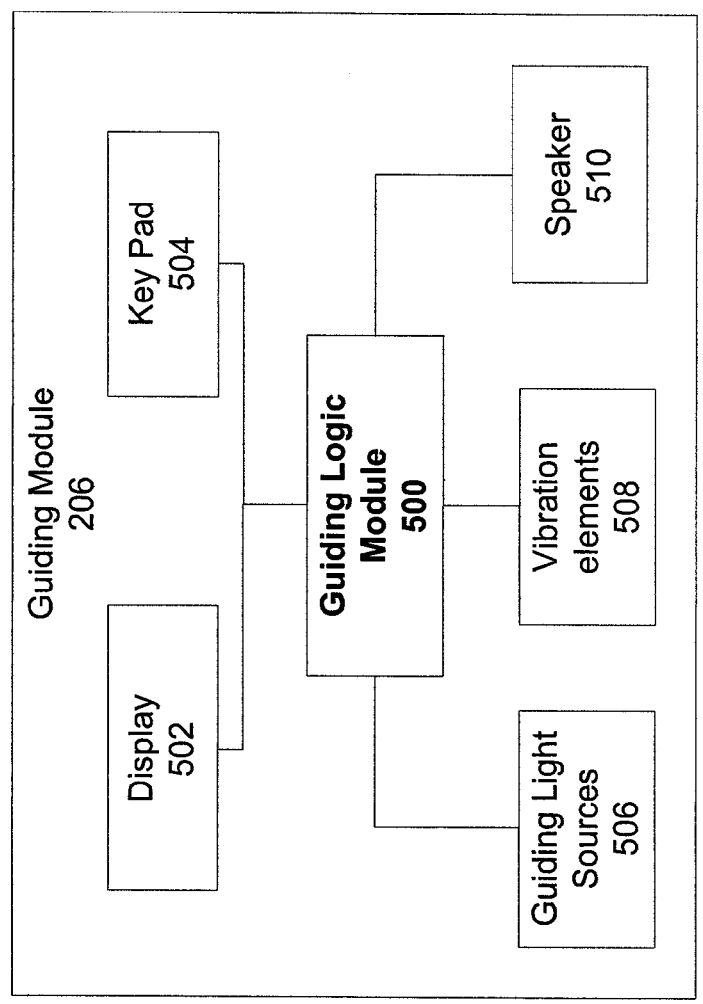
FIG. 5 is a block diagram schematically illustrating an example of a guiding module configured to guide the diagnostic device user, in accordance with the presently disclosed subject matter.

FIG. 5 is a block diagram schematically illustrating an example of a guiding module configured to guide the diagnostic device user, in accordance with the presently disclosed subject matter. Guiding module 206 can comprise guiding logic module 500. As indicated above, guiding logic module 500 can be configured to provide various guidance data instructing user 102 how to maneuver diagnostics devise 104 to the desired diagnostics device 104 spatial disposition with respect to patient's 103 body (or a specific part thereof). Such guidance data can include, inter alia, voice commands, image display, diagnostics device 104 vibrations, etc. Such guidance data can be presented to user 102 continuously or periodically, until diagnostics device 104 arrives at desired diagnostics device 104 spatial disposition with respect to patient's 103 body (or a specific part thereof). Such guidance data can be calculated according to the respective calculation of a route to the desired diagnostics device 104 spatial disposition with respect to patient's 103 body (or a specific part thereof), as calculated by navigation module 204.

For that purpose, guiding module 206 can comprise one or more output sources, such as, for example, display 502, speaker 510, vibration elements 508, guiding light sources 506, keypad 504, etc. Display 502 can be configured to present visual data providing user 102 with information on how to maneuver diagnostics devise 104 to the desired diagnostics device 104 spatial disposition with respect to patient's 103 body (or a specific part thereof). Such information can, in some cases, include a visual representation of diagnostics device 104 current spatial disposition with respect to patient's 103 body (or a specific part thereof) and on the desired diagnostics device 104 spatial disposition with respect to patient's 103 body (or a specific part thereof).

Figure 13:
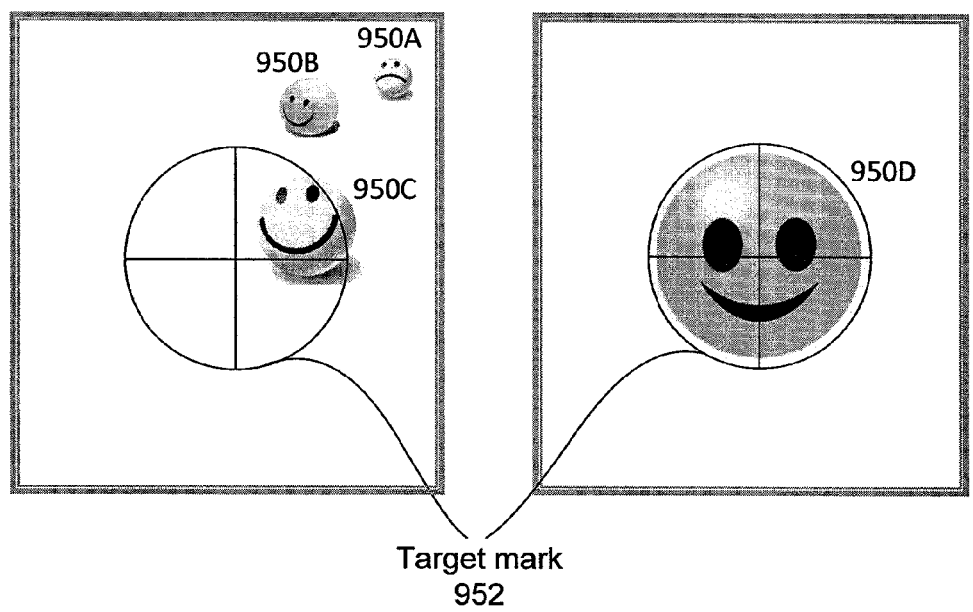
FIG. 13 is a schematic illustration of exemplary presentation of navigational instructions to a diagnostic device user, in accordance with the presently disclosed subject matter.

Reverting to FIG. 13, there is shown a schematic illustration of exemplary presentation of navigational instructions to a diagnostic device user, in accordance with the presently disclosed subject matter. It can be noted that object 950A, 950B, 950C representing diagnostics device 104 current spatial disposition with respect to patient's 103 body (or a specific part thereof) can be presented on display 502, along with a target mark 952 representing the desired diagnostics device 104 spatial disposition with respect to patient's 103 body (or a specific part thereof). A three dimensional smiley object 950A, 950B, 950C representation on display 502 continuously or periodically updates reflecting changes to diagnostics device 104 spatial disposition with respect to patient's 103 body (or a specific part thereof). It can be noted that initially object 950A is positioned relatively far from target mark 952 (it can be appreciated that it is located above and to the right of target mark 952). In addition, diagnostics device is not oriented as required (it can be appreciated that it is not facing directly forward). User 102 repositions and reorients diagnostics device 104 according to the feedback presented on display 502. Repositioning can be made by moving diagnostics device 104 forward/backward, up/down, left/right. Reorienting can be made by roll, pitch, yaw movements of diagnostics device 104. Such repositioning and reorientation of diagnostics device 104 is reflected on display 502, for example continuously or periodically. It can be appreciated that after repositioning and reorienting of object 950A, diagnostics device 104 is coming closer to the desired spatial disposition with respect to patient's 103 body (or a specific part thereof) at object 950B, which, as can be appreciated, is closer to target mark 952. After further repositioning and reorienting of object 950B, diagnostics device 104 is coming still closer to the desired spatial disposition with respect to patient's 103 body (or a specific part thereof) at object 950C, which, as can be appreciated, is even closer to target mark 952 than object 950B. Finally, after further repositioning and reorienting of object 950C, diagnostics device 104 is at target mark 952—the desired spatial disposition with respect to patient's 103 body (or a specific part thereof). It can be noted that object 950 can comprise of visual representation and hints about the navigation process, such representations can include for example color changes (such as red for wrong and green for good), and/or emoticons illustrating the proximity of diagnostics device 104 to desired spatial disposition with respect to patient's 103 body (or a specific part thereof) (for example, object 950 initially has a sad smiley and as it nears target mark 952 the sad smiley becomes a happy smiley).

Returning to FIG. 5, speaker 510 can provide voice instructions to user 102 indicating the required movements user 102 should perform in order to bring diagnostics device to desired spatial disposition with respect to patient's 103 body (or a specific part thereof). In addition speaker 510 can provide sound feedbacks about proximity of diagnostics device 104 to desired spatial disposition with respect to patient's 103 body (or a specific part thereof) (for example a sound feedback might be a series of short beeps and changes to their rate according to the proximity of diagnostics device 104 to desired spatial disposition).

Vibration elements 508 can provide vibrating feedback, for example in order to indicate user 102 that a movement that he is making is not correct (e.g. if diagnostics device 104 should be moved to the right and user 102 moves it to the left, a vibration can be initiated). Vibration can also be provided indicating that diagnostics device reached desired spatial disposition with respect to patient's 103 body (or a specific part thereof). In some cases such vibration will be a different vibration than a vibration indicating wrong movement.

Guiding light source 506 can provide light feedback to user 102 about required diagnostics device 104 movement and/or proximity of diagnostics device 104 to desired spatial disposition with respect to patient's 103 body (or a specific part thereof). For example a combination of LED elements (such as a matrix of LED elements located on diagnostic device 104) can provide user 102 with a light feedback about the required movement direction (e.g. right, left, up, down, etc.). In such case, guiding light source 506 can be configured to utilize movement sensors 612 and orientation sensors 614 in order to calculate and use the correct light source (e.g. specific LED, etc.) which is relevant to the current movement based on current diagnostic device 104 spatial disposition with respect to patient's 103 body (or a specific part thereof) (e.g. the same LED can sometimes point up and sometimes down according to the device orientation). In addition, the LED elements can also provide a proximity feedback using specific rate of lights going on and off.

Key pad 504—In some cases the guiding process, using guiding logic module 500 can also require a feedback from user 102, for example a confirmation about ending a specific medical examination, etc. For that purpose, guiding module 206 can comprise one or more input sources, such as, for example, keypad 504.

Figure 6:
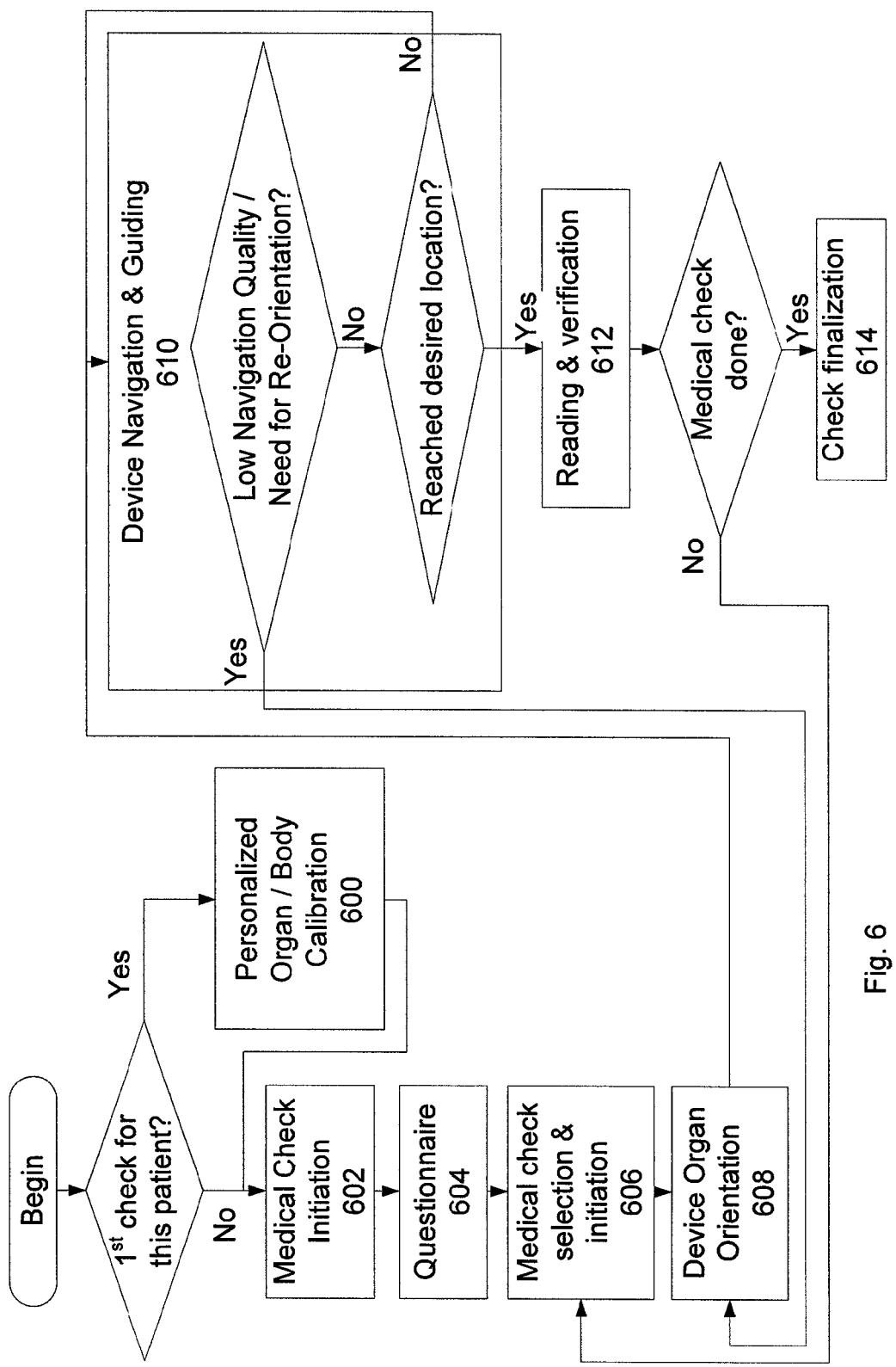
FIG. 6 is a flowchart illustrating one example of a sequence of operations carried out for performing an automatic and self-guided medical examination, in accordance with the presently disclosed subject matter.

FIG. 6 is a flowchart illustrating one example of a sequence of operations carried out for performing an automatic and self-guided medical examination, in accordance with the presently disclosed subject matter. Initially, a check is performed if the initiated check is the first check of patient 103 with a diagnostics device 104. In case the answer is yes, personalized organ/body calibration is performed (step 600), as further detailed with respect to FIG. 7. In case the answer is no, or following performance of personalized organ/body calibration 600, a medical examination is initiated (step 602). During initiation, diagnostics device 104 (for example by utilizing examination logic module 208) can receive an indication of patient 103 to be checked. Such indication can be received, for example, as input from user 102 or by utilizing an automatic patient identification method, as detailed with respect to FIG. 2. Diagnostics device 104 can be further configured to retrieve various data relating to patient 103. Such data can be retrieved from one or more of: data repository 216, check plan repository 210, trained personnel data repository 123, patient & check plan repository 136 or any other location operatively connected to diagnostics device 104 on which patient data is stored. Such data can include, inter alia, data relating to a patient specific check plan, reading references, communication parameters, etc.

Diagnostics device 104, for example by utilizing examination logic module 208, can be further configured to display a questionnaire (step 604) to be answered by user 102 and/or patient 103. Questionnaire can be displayed, for example, on patient workstation 114 or can be played as a voice based questionnaire. Questionnaire can comprise generic and/or patient 103 specific questions designed to provide trained personnel 124 with various data (e.g. data relating to patient 103 medical condition), including data required to enable analysis of the medical data acquired during the medical examinations (e.g. "does the patient have a fever and how long?", "how high is it?", "does the patient feel any pain?", "where is the pain located?", etc.). User 102 or patient 103 can answer the questionnaire using for example voice recording using the diagnostic device 104 or using the patient workstation 114, or for example by replying to a computerized questionnaire which can be displayed on patient workstation 114. It is to be noted that other methods can be utilized in order to provide answers to the questionnaire.

Diagnostics device 104, for example by utilizing examination logic module 208, can be further configured to perform a medical examination selection and initiation (step 606). For that purpose, diagnostics device 104 can enable user 102 to select a medical examination to be performed, either manually or from a list of checks to be performed as defined in patient 103 check plan. Alternatively, diagnostics device 104 can select and initiate a check according to a pre-defined order set by patient 103 specific check plan, without input from user 102. The medical examination initiation can consist of, for example, retrieving reference medical examination data from the check plan or a relevant repository (similar to medical examination initiation step 602).

Following selection of a check, diagnostics device 104, for example by utilizing navigation module 204, can be configured to perform device orientation (step 608). For example, diagnostics device 104 can instruct user 102 to move it to a position and orientation in proximity of a known reference point (e.g. patient 103 nose, ear, eye, etc.). During positioning of diagnostics device in proximity of such known reference point, diagnostics device 104 can instruct navigation camera to continuously or periodically acquire images of the patient's body. Diagnostics device 104 can continuously compare the acquired images to known reference images of patient 103 (e.g. reference images saved for example in one or more of: check plan repository 210, data repository 216, patient & check plan repository 136, trained personnel data repository 123 or any other location operatively connected to diagnostics device 104 on which patient data is stored), as further detailed, inter alia with respect to FIG. 4. Once a match is found, diagnostics device 104 can be configured to notify user 102 of the match and to determine its spatial disposition with respect to patient's 103 body (or a specific part thereof).

Following orientation of diagnostics device 104 with respect to patient's 103 body (or a specific part thereof), diagnostics device 104, for example by utilizing navigation module 204, can be configured to perform navigation and guiding (step 610) of diagnostics device 104 to the desired spatial disposition with respect to the patient's 103 body (or a specific part thereof) that will enable acquisition of medical data by diagnostics device 104. Diagnostics device 104 can be configured to calculate a route to a desired spatial disposition with respect to the patient's 103 body (or a specific part thereof). Such desired spatial disposition with respect to the patient's 103 body (or a specific part thereof) can be defined, for example, by the patient specific check plan (e.g. in accordance with the personalized organ/body calibration performed for patient 103). The route calculation is performed continuously or periodically, for example until arrival to the desired diagnostics device 104 spatial disposition with respect to the patient's 103 body (or a specific part thereof). It is to be noted that the navigation and route calculation processes are further explained below, inter alia with respect to FIGS. 11 and 12. In parallel, and until arrival of diagnostics device 104 to the desired spatial disposition with respect to the patient's 103 body (or a specific part thereof), diagnostics device 104, for example by utilizing guiding module 206, can provide various guidance data instructing user 102 how to maneuver diagnostics devise 104 to the desired diagnostics device 104 spatial disposition with respect to the patient's 103 body (or a specific part thereof), in accordance with the navigation calculations indicated above. As indicated above, such guidance data can be conveyed to user 102 using various output means, such as, image display, voice commands, diagnostics device 104 vibrations, etc. Throughout navigation and guiding of diagnostics device 104, diagnostics device 104 can be configured to check if the navigation quality is sufficient and if there is a need in re-orienting diagnostics device 104. Such checks can be performed for example by searching for additional reference images at pre-defined locations along the way, whereas in case the images acquired by navigation camera 420 do not match the expected reference images (for example as defined by patient 103 check plan), there is a need in re-orientation of navigation device 104. In addition, for example, navigation module logic 400 can also calculate the navigation quality by calculating the distance between diagnostic device 104 spatial disposition with respect to the patient's 103 body (or a specific part thereof) with the target desired spatial disposition with respect to the patient's 103 body (or a specific part thereof) and check whether there is a route convergence (i.e. the distance is getting smaller) or route divergence (distance is getting bigger).

It is to be noted that in some cases, diagnostics device 104 navigation can be performed without use of any patient specific reference data, but only using generic reference data. In such cases, diagnostics device 104 can be configured to continuously or periodically acquire patient medical data, and monitor to see if the acquired medical data meets certain criteria that indicate that the acquired data is the requested data. For example, diagnostic device 104 can use predefined generic images of a typical organ such as an ear drum (not specific to a patient) as a reference. In this case, for example, diagnostic device 104 can be configured to continually analyze the acquired patient's internal ear image, and try to match the reading to the generic image reference. Matching criteria can be, for example, a unique image characteristic of the organ such as the circular structure of the eardrum, and its image contrast compared to the surrounding image. Another example for a generic organ reading reference can be a generic sound wave of a human heart, and in this case, for example, the matching criteria can be the sound wave unique structure and special characteristics such as pace, amplitude, volume, etc.

In still further cases, diagnostics device 104 navigation can be performed with utilization of INS readings alone, using, for example, movement sensors 412 and orientation sensors 414. In such cases, diagnostics device 104 can be initiated for example by touching three identifiable body points, such as two patient 103 nipples and patient 103 belly button. Using known in the art triangulation calculation methods, diagnostics device 104 can than utilize movement sensors 412 and orientation sensors 414 alone to navigate to various body points.

Upon arrival to diagnostics device 104 desired spatial disposition with respect to the patient's 103 body (or a specific part thereof), diagnostics device 104, for example by utilizing reading and verification logic module 212, can be configured to perform a reading and verification of the reading (step 612). Diagnostics device 104 can be configured to verify that it is located at the desired spatial disposition with respect to the patient's 103 body (or a specific part thereof) when acquiring medical data of patient 103. Diagnostics device 104 can be further configured to prepare for acquiring medical data of patient 103, and to perform acquisition of such medical data. After acquisition of medical data of patient, diagnostics device 104 can be configured to verify that the acquired data meets pre-defined standards (e.g. a required length of reading, recorded sound volume, reading parameters thresholds, etc.), as further detailed below, inter alia with reference to FIG. 14. In case the acquired data does not meet the pre-defined standards, diagnostics device 104 can in some cases be configured to instruct user 102 to perform the required repositioning and reorienting thereof in order to bring diagnostics device 104 to the desired spatial disposition with respect to the patient's 103 body (or a specific part thereof). Following repositioning and reorienting of diagnostics device 104, reading and verification logic module 212 can be configured to retry acquiring the medical data of patient 103, as further detailed below, inter alia with reference to FIG. 14.

Following reading acquisition and verification of patient 103 medical data, diagnostics device 104 can be configured to check if the medical examination is done (e.g. all medical examinations defined by patient 103 check plan have been performed). If not, diagnostics device 104 can be configured to move to the next medical examination indicated by patient 103 check plan. If all required medical examinations are performed, diagnostics device 104 can be configured to finalize the check (step 614). During the check finalization 614, as well as in any other step of the described process, diagnostic device 104 can be configured to perform any required action to the acquired patient 103 medical data. Such actions can include, for example, updating repository status, embedding patient data or check data in the reading data, encrypting data, compressing data, transmitting the acquired data to different locations (e.g. trained personnel workstation 122 and/or central system 130), etc.

Figure 7:
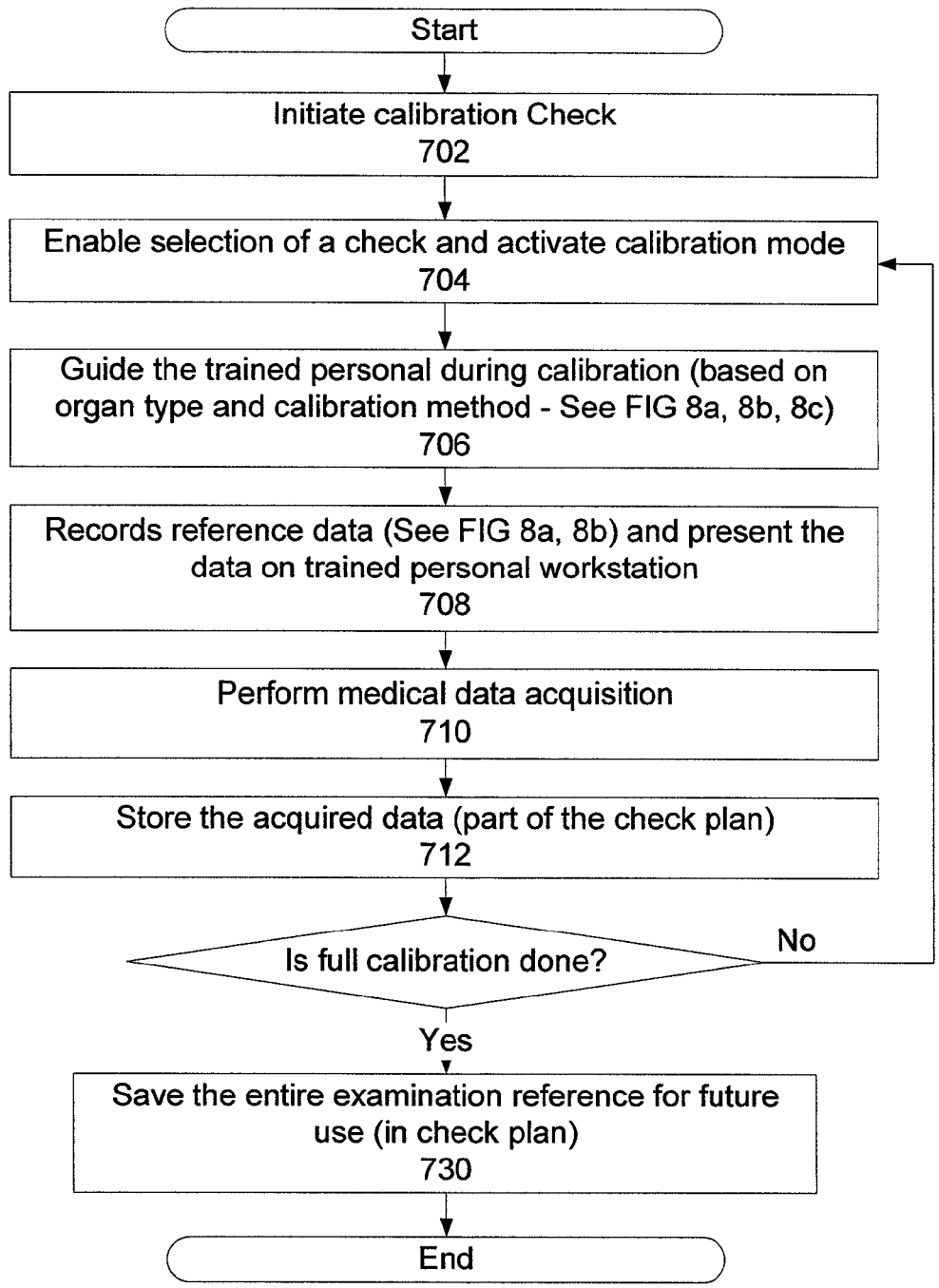
FIG. 7 is a flowchart illustrating one example of a sequence of operations carried out for performing personalized calibration of a diagnostic device, in accordance with the presently disclosed subject matter.

FIG. 7 is a flowchart illustrating one example of a sequence of operations carried out for performing personalized calibration of a diagnostic device, in accordance with the presently disclosed subject matter. Diagnostics device 104, for example by utilizing calibration logic module 214, can be configured to initiate a calibration check (step 702). The initial calibration can be performed by trained personnel 124. During calibration trained personnel 124 activates diagnostics device 104 instead of user 102. This can require patient 103 arrival to trained personnel location 120 or trained personnel 124 arrival to patient location 100 for diagnostics device calibration. It is to be noted that diagnostics device 104 can be configured to allow performing the calibration process by user 102 with a remote guiding and assistance of trained personnel 124.

After calibration initiation, trained personnel 124 can select a specific check (for example a check that is required for the specific patient 103 and activate diagnostics device 104 calibration mode (step 704). Optionally, the specific check is selected from a list of checks (that can be displayed, for example, on diagnostic device 104 or on trained personnel workstation 122). Following activation of calibration mode, diagnostics device 104 can be configured to guide trained personnel 124 during calibration (step 706). Such guidance of trained personnel 124 is performed in accordance with the selected check and the calibration method.

Diagnostics device 104 can be further configured to record reference data (in accordance with the calibration method, as detailed below) during performance of the medical examination by trained personnel 124 and optionally present the recorded data, for example on trained personnel workstation 122 (step 708). The recorded reference data can be stored, for example, in one or more of: check plan repository 210, data repository 216, patient & check plan repository 136, trained personnel data repository 123 or any other location operatively connected to diagnostics device 104 on which patient data is stored.

Reverting to FIG. 8a, there is shown a flowchart illustrating an example of a sequence of operations carried out for recording reference data during personalized calibration of a diagnostic device, using imaging and orientation sensors, in accordance with the presently disclosed subject matter. According to this calibration method, trained personnel 124 perform the medical examination while diagnostics device 104 records various data (step 740), including patient 103 body images using navigation camera 420 and diagnostics device 104 INS data using INS sensors 410 (6 axis movement—using accelerometers and gyroscopes). In some cases, diagnostics device 104 can be further configured to record data relating to the distance of diagnostics sensor from patient 103 body using distance sensors 430. In some cases, diagnostics device 104 can be further configured to record data relating to the pressure exerted on diagnostics device against patient 103 body using pressure sensors 440. Following positioning and orienting diagnostics device 104 in the desired spatial disposition with respect to the patient's 103 body (or a specific part thereof) (according to trained personnel 124 decision), trained personnel can perform medical data acquisition, whereas diagnostics device 104 can be configured to record the medical data acquired by image based sensors 310 and/or sound based sensors 320. All the recorded data can be saved on one or more of check plan repository 210, data repository 216, patient & check plan repository 136, medical examination repository 134, or any other location operatively connected to diagnostics device 104 on which patient data can be stored.

Figure 8B:
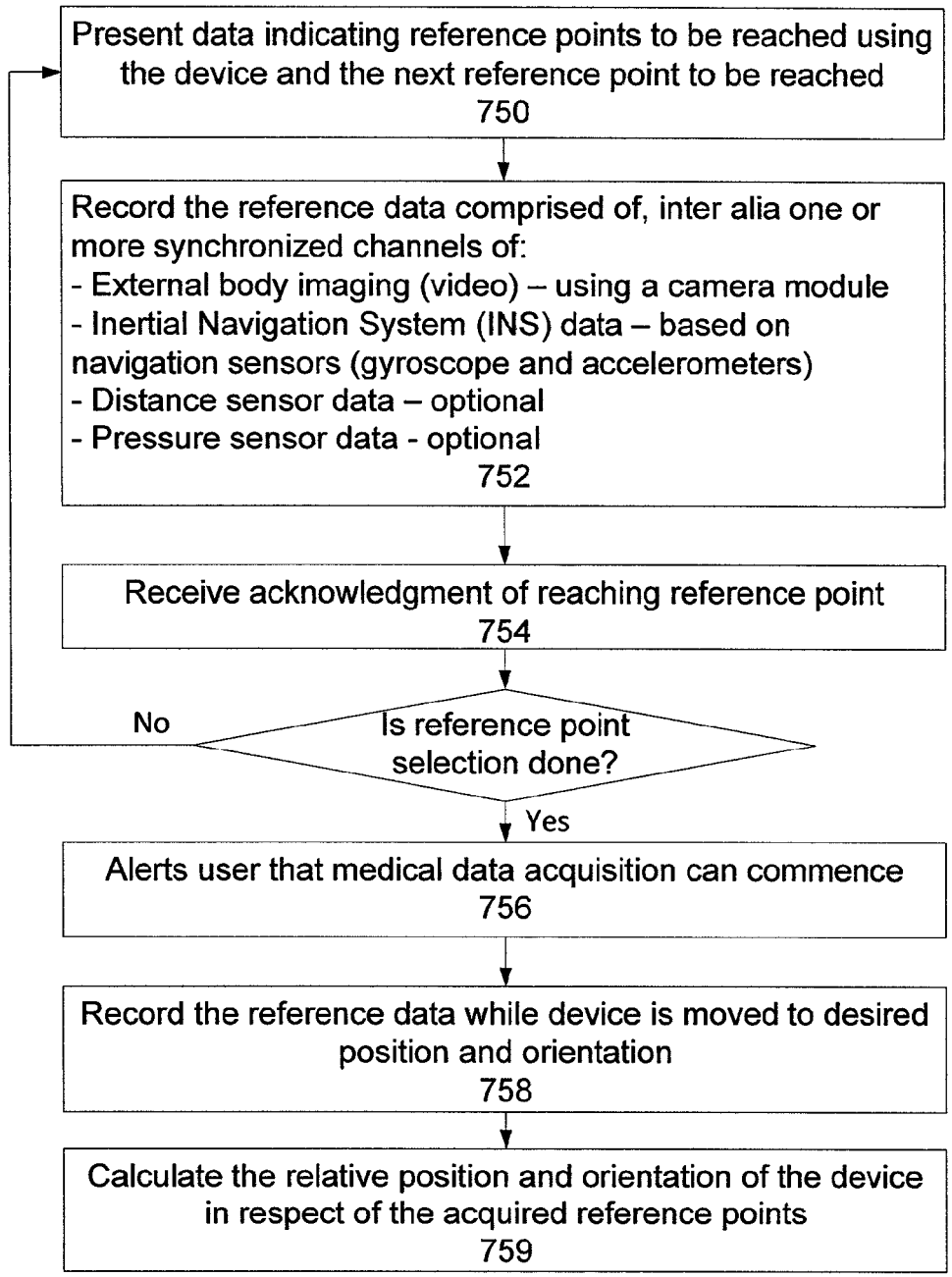
FIG. 8b is a flowchart illustrating an example of a sequence of operations carried out for recording reference data during personalized calibration of a diagnostic device, using INS sensors and body points, in accordance with the presently disclosed subject matter.

Reverting to FIG. 8b there is shown a flowchart illustrating an example of a sequence of operations carried out for recording reference data during personalized calibration of a diagnostic device, using INS sensors and body points, in accordance with the presently disclosed subject matter. Also according to this calibration method, trained personnel 124 performs the medical examination while diagnostics device 104 records various data, including patient 103 body images using navigation camera 420 and diagnostics device 104 INS data using INS sensors 410 (6 axis movement—using accelerometers and gyroscopes). Diagnostics device 104 can be configured to present trained personnel 124 (for example on trained personnel workstation 122) data indicating a reference point to be reached and the next reference point to be reached from the first reference point (step 750). Trained personnel 124 can be instructed to move diagnostics device 104 to the first reference point he should reach, touch the reference point with diagnostics device 104 and from there move to the next reference point he should reach and touch it as well. During the movement of diagnostics device 104 to and between the reference points, diagnostics device records data (step 752), including patient 103 body images using navigation camera 420 and diagnostics device 104 INS data using INS sensors 410 (6 axis movement—using accelerometers and gyroscopes). In some cases, diagnostics device 104 can be further configured to record data relating to the distance of diagnostics sensor from patient 103 body using distance sensors 430. In some cases, diagnostics device 104 can be further configured to record data relating to the pressure exerted on diagnostics device against patient 103 body using pressure sensors 440. Upon arrival of diagnostics device to a reference point, as indicated above, diagnostics device touches the point, thus indicating that its current location is the reference point location (step 754). In some cases the trained personnel 124 can also acknowledge reaching the desired reference point, by using the device keypad 504 or any other confirmation method. The process repeats until enough reference points are selected. It is to be noted that in some cases three reference points are enough as they form a basis for utilization of known triangulation techniques that can be used for navigating diagnostics device 104. Following acquisition of reference points data, diagnostics device 104 can be configured to alert trained personnel 124 that medical data acquisition can commence (step 756). Trained personnel 124 can then move diagnostics device 104 to the desired spatial disposition with respect to the patient's 103 body (or a specific part thereof) from which a medical data acquisition can be performed (step 758), while diagnostics device continues to record the reference data (including, inter alia, patient 103 body images and diagnostics device 104 INS data). Following acquisition of all reference data, including the reference points, diagnostics device 104 can be configured to calculate the relative spatial disposition of diagnostics device 104 in respect of the acquired reference points (step 759).

Figure 8C:
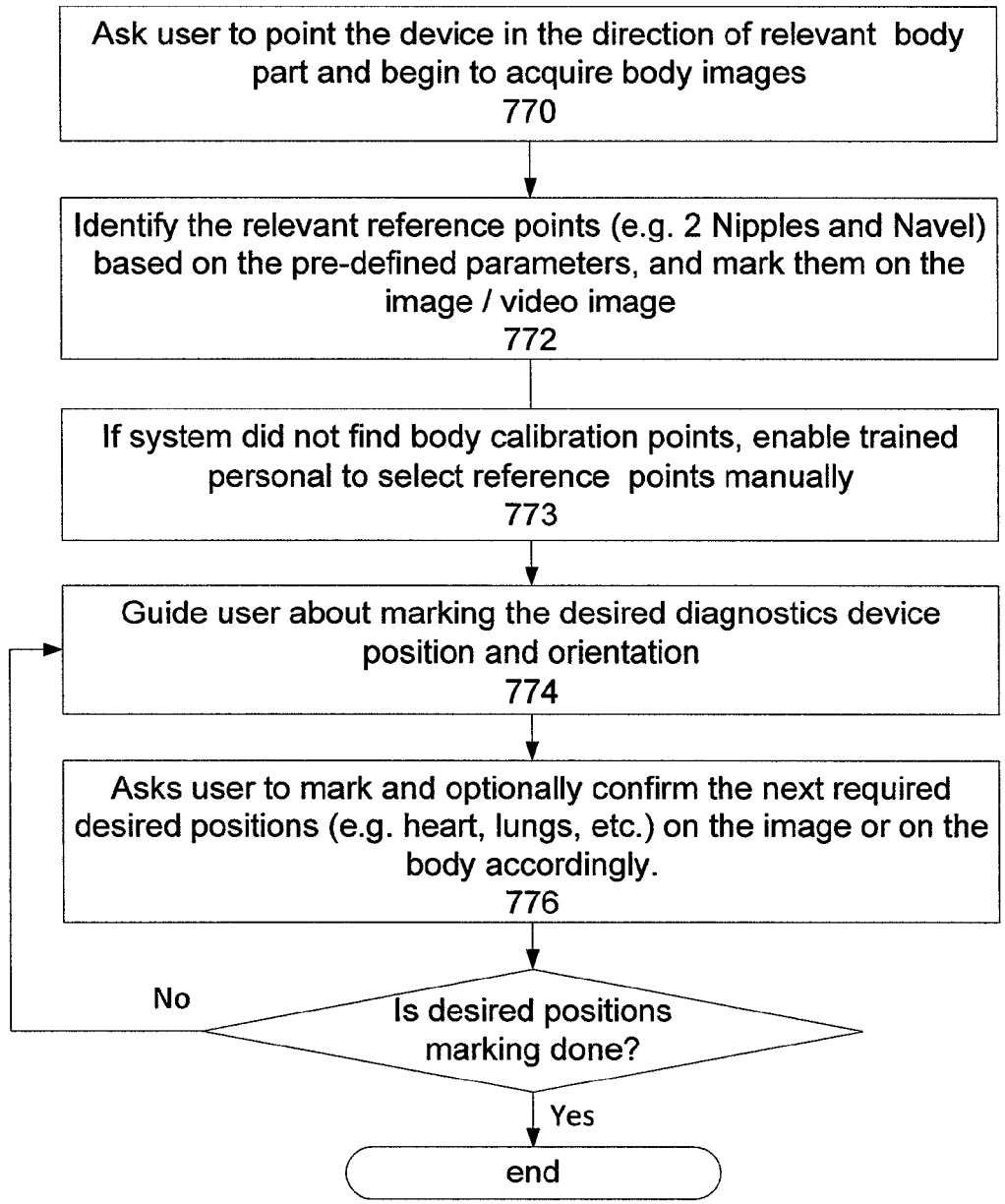
FIG. 8c is a flowchart illustrating one example of a sequence of operations carried out for recording reference data during personalized calibration of a diagnostic device, using reference points and pointing object, in accordance with the presently disclosed subject matter.

Reverting to FIG. 8c there is shown a flowchart illustrating one example of a sequence of operations carried out for recording reference data during personalized calibration of a diagnostic device, using reference points and pointing object, in accordance with the presently disclosed subject matter. According to this calibration method, trained personnel 124 performs the medical examination while diagnostics device 104 records various data, including patient's 103 body images using navigation camera 420. Diagnostics device 104 can be configured to instruct trained personnel 124 to point diagnostics device 104 in the direction of a relevant body part (e.g. chest, back, head, etc.) and acquire an image by utilizing, for example, navigation camera 420 (step 770).

Following acquisition of an image diagnostics device 104 can be configured to try to extract reference points from the acquired image. For this purpose, diagnostics device can be configured to utilize pre-stored data relating to expected points within the area of the acquired image (e.g. if the acquired image is of patient 103 head, expected reference points can be the eyes, the nose, the mouth, the eyebrows, etc., if the acquired image is of patient chest, expected reference points can be the nipples, the navel, etc.) in order to try and find a match thereto within the acquired image (step 772). For example, if an image of the chest was acquired, diagnostics device 104 can be configured to look for the nipples in the acquired image (for example diagnostics device 104 can utilize pre-stored data that indicates that a nipple appearance is round, its size can have a certain range and it is regularly darker than its surrounding area). Diagnostics device 104 can be configured to ask trained personnel 124 to acknowledge the calculated reference points.

In case diagnostics device 104 fails to find a match to the expected reference points within the acquired image, diagnostics device 104 can optionally be configured to notify trained personnel 124 of the failure. Diagnostics device 104 can optionally be further configured to enable trained personnel 124 to mark the reference points manually on the acquired image that, for that purpose, can be displayed on trained personnel workstation 122 (step 773). Such marking of the reference points can be performed for example by using an indicator presented on trained personnel workstation 122, where said indicator can be moved, for example, by a computer mouse or any other suitable input device (e.g. keypad, track pad, etc.). Alternatively or additionally, diagnostics device 104 can be configured to enable such marking by touch of trained personnel 124 on the reference points, for example using his finger. In such cases, diagnostics device 104 can be configured to identify trained personnel 124 finger within the image acquired by navigation camera 420.

Following marking of the reference points, diagnostics device 104 can be configured to instruct trained personnel 124 to mark the desired location of diagnostics device 104 for medical data acquisition on the acquired image (step 774). In some cases, diagnostics device 104 can be further configured to mark the next desired location of diagnostics device 104 for medical data acquisition on the acquired image (step 775), and the process repeats until all desired locations of diagnostics device 104 for medical data acquisition are marked on the acquired image.

It is to be noted that in some cases, each of the calibration methods detailed above can be performed virtually, as instead of an actual physical meeting between trained personnel 124 and patient 103, a virtual meeting can take place, in which trained personnel 124 can, for example, guide user 102 on how to perform the calibration. In such cases, user 102 can activate diagnostics device throughout the calibration according to trained personnel 124 instructions. Such virtual meeting can utilize known methods and techniques such as video conferencing, etc.

Returning to FIG. 7, after arrival to the desired diagnostics device 104 spatial disposition with respect to the patient's 103 body (or a specific part thereof), while recording reference data, diagnostics device 104 can be further configured to enable trained personnel 124 to perform medical data acquisition (step 710). Diagnostics device 104 can be further configured to store the acquired medical data as reference data (step 712) (as indicated above, the recorded reference data can be stored, for example, in one or more of: check plan repository 210, data repository 216, patient & check plan repository 136, trained personnel data repository 123 or any other location operatively connected to diagnostics device 104 on which patient data is stored).

Diagnostics device 104 can be further configured to repeat the process until calibration is done (for example as indicated by trained personnel 124).

Diagnostics device 104 can be further configured to store the entire examination process (e.g. the series of medical examinations performed by trained personnel 124), for example, in one or more of: check plan repository 210, data repository 216, patient & check plan repository 136, trained personnel data repository 123 or any other location operatively connected to diagnostics device 104 on which patient data is stored (step 730).

It is to be noted that in some cases, there is no need in performing any calibration of diagnostics device 104. In such cases, diagnostics device 104 can be configured to perform a generic check plan or a modified personal check plan using only generic reference data, without utilizing any personal reference data that requires calibration process to the diagnostic device 104. It is to be further noted that in such cases, when performing a certain check (e.g. throat check, ear check, etc.) diagnostics device 104 can instruct user 102 to move to a spatial disposition with respect to the patient's 103 body (or a specific part thereof) in proximity of a known reference point (e.g. patient 103 nose, ear, eye, etc.). During the positioning, diagnostics device 104 can instruct the relevant image based sensor 310 (e.g. relevant organ camera sensor such as ear reading sensor, etc.) to continuously or periodically acquire organ images. Diagnostics device 104 can continuously or periodically compare the acquired images to known generic reference images of the required organ to be read (e.g. reference images of "ear drums", throat tonsils, etc.). The reference images can be saved for example in check plan repository 210, data repository 216, patient & check plan repository 136, trained personnel data repository 123 or any other location operatively connected to diagnostics device 104 on which patient data is stored. User 102 can then move diagnostics device 104 towards a spatial disposition with respect to the patient's 103 body (or a specific part thereof) approximate to the desired spatial disposition with respect to the patient's 103 body (or a specific part thereof) until diagnostics device 104 identifies at least one matching reference point (as further detailed below, inter alia with respect to FIGS. 9 and 10, reference points can also be reference patterns). Once diagnostics device 104 reaches the desired spatial disposition with respect to the patient's 103 body (or a specific part thereof) it can generate an alert to user 102 and perform a data acquisition and verification as defined in the check plan and explained above.

Figure 9:
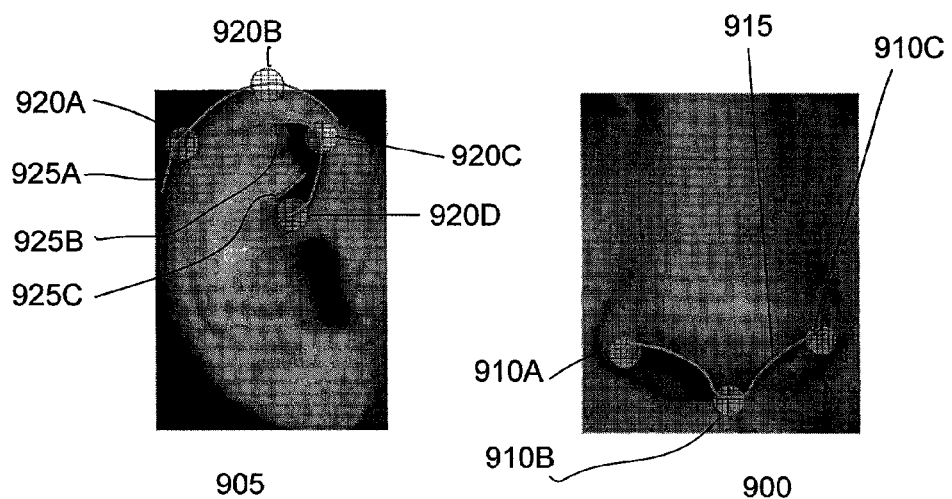
FIG. 9 is a schematic illustration of exemplary image based reference patterns, in accordance with the presently disclosed subject matter.

FIG. 9 is a schematic illustration of exemplary image based reference points and patterns, in accordance with the presently disclosed subject matter. It can be noted that each patient organ can be associated with one or more reference points. A reference point can in some cases also be a certain pattern such as the linear shape formed by the patient organ structure. For example, patient nose 900 can have multiple reference points associated therewith, including 910A-910C. Such reference points can be, for example, located at the edges of the nose (such as 910A and 910C), at the middle of the nose (such as 910B) or at any other location associated with patient nose (not shown). Patient ear 905 can have multiple reference points associated therewith, including 920A-920D. Such reference points can be, for example, located at the edges of the ear (such as 920A-920B), at curves formed by the ear structure (such as 920B and 920 D) or at any other location associated with patient ear (not shown). A reference point can also be a certain pattern such as the linear shapes formed by the patient's organ structure. Such types of reference points are illustrated in the figure by reference numerals 915, 925A, 925B and 925C. It can be appreciated that such reference points type reflect the relevant organ structure of a specific patient, and utilization thereof inter alia enables determination of the relative diagnostics device 104 spatial disposition with respect to the patient's 103 body (or a specific part thereof) and navigation of diagnostics device 104 to the desired spatial disposition with respect to the patient's 103 body (or a specific part thereof).

Figure 10:
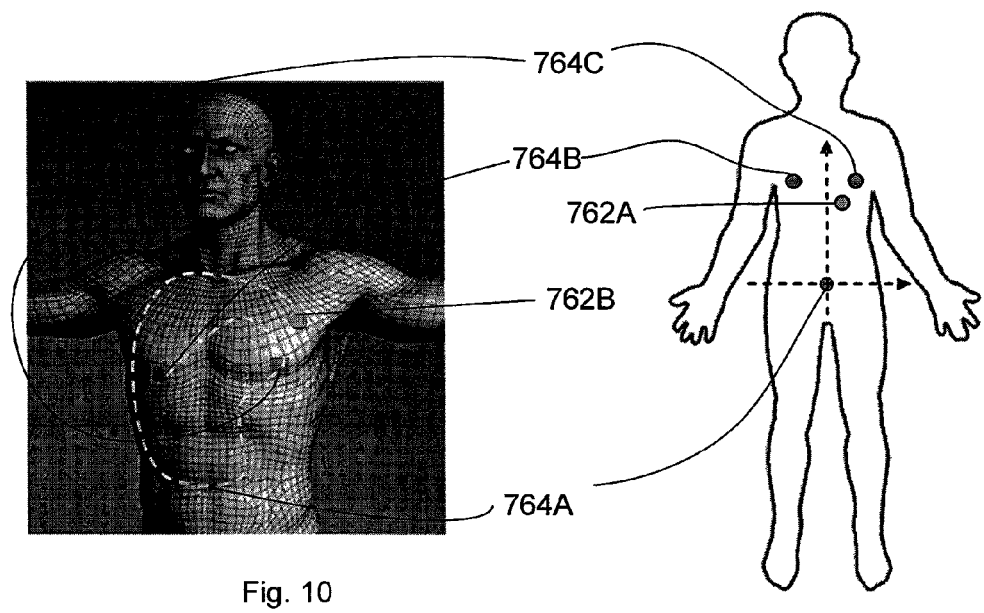
FIG. 10 is a schematic illustration of exemplary image based and INS based reference points, in accordance with the presently disclosed subject matter.

FIG. 10 is a schematic illustration of exemplary image based and INS based reference points, in accordance with the presently disclosed subject matter. It can be noted that reference points 764A-764C can be used in order to enable for example triangulation based navigation using INS sensors 410. As indicated above (inter alia with reference to FIG. 8b.), diagnostics device 104 can be configured to acquire reference data of three reference points (e.g. left nipple 764C, right nipple 764B and navel 764A). Diagnostics device 104 can be further configured to utilize the reference data and INS sensors 410 data in order to determine the location of desired spatial dispositions of diagnostics device 104 (for example positions and orientations 762A, 762B, etc.) with respect to patient's 103 body (or a specific part thereof). It is to be noted that diagnostic device 104 can also use the reference points 764A-764-C to enable image based calculations and user guidance to a desired spatial disposition (for example 762A, 762B) with respect to patient's 103 body (or a specific part thereof) (for example in order to acquire medical data).

Figure 11:
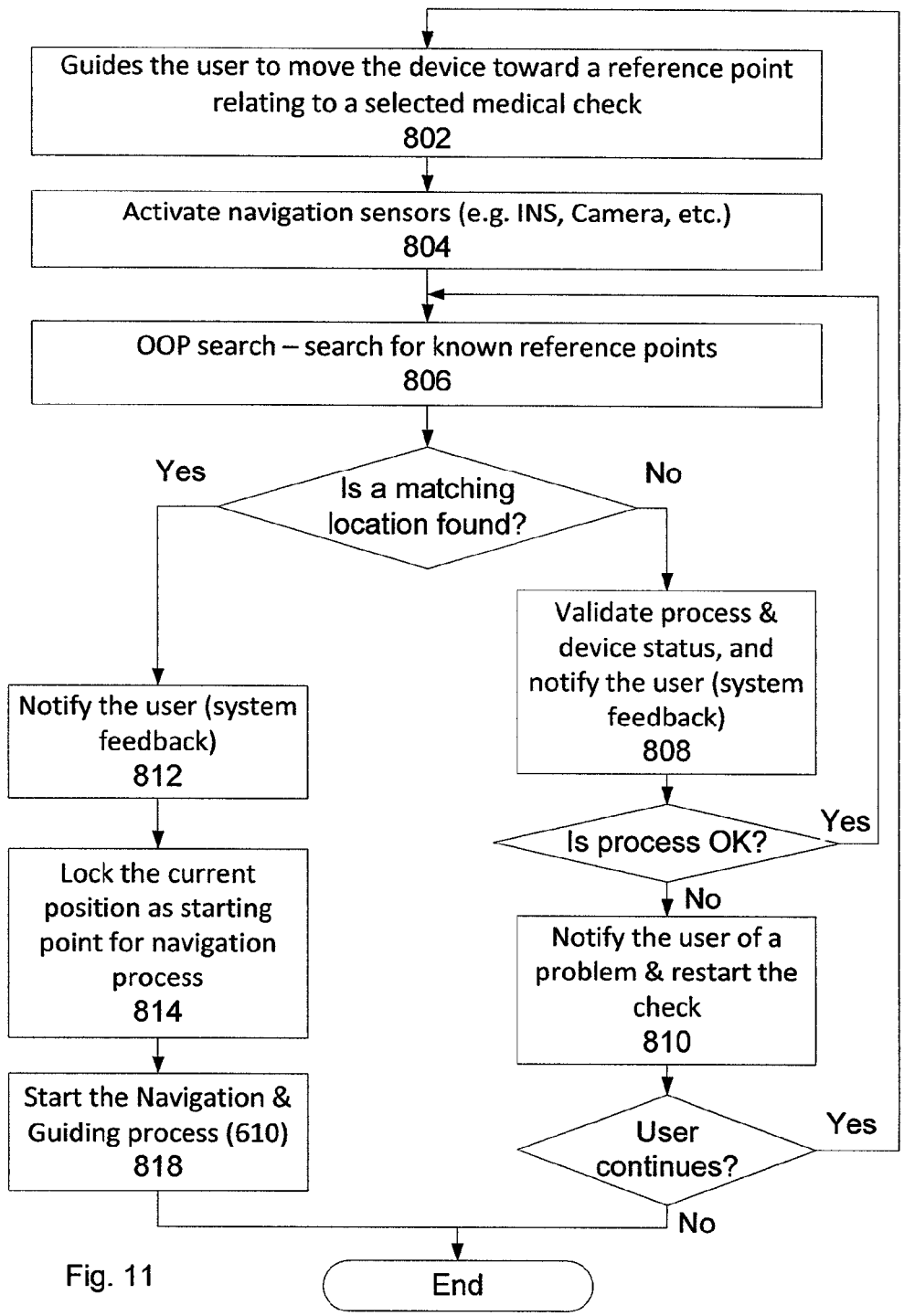
FIG. 11 is a flowchart illustrating one example of a sequence of operations carried out for calculating the spatial disposition of a diagnostic device with respect to patient's 103 body (or a specific part thereof), in accordance with the presently disclosed subject matter.

FIG. 11 is a flowchart illustrating one example of a sequence of operations carried out for calculating the spatial disposition of a diagnostic device with respect to patient's 103 body (or a specific part thereof), in accordance with the presently disclosed subject matter. Diagnostics device 104, for example by utilizing navigation module 204, can be configured to instruct user 102 to move diagnostics device 104 to be in proximity to a known reference point relating to the specific selected medical examination (step 802). For example, if the selected check is an ear check, diagnostics device 104 can be configured to instruct user 102 to move diagnostics device 104 to the proximity of patient 103 ear.

Following locating diagnostics device 104 in proximity of a known reference point relating to the specific selected medical examination, diagnostics device 104 can be configured to activate one or more navigation sensors such as INS sensors 410, navigation camera 420, navigation light sources 426, pressure sensors 440, distance sensors 430, etc. (step 804).

Diagnostics device 104 can be configured to utilize the data received from the one or more navigation sensors and start searching for known reference points according to which the current spatial disposition of diagnostics device 104 with respect to the desired position and orientation with respect to patient's 103 body (or a specific part thereof) can be calculated (step 806). The current spatial disposition of diagnostics device 104 with respect to patient's 103 body (or a specific part thereof) can be calculated by utilizing identification of one or more known reference points (stored on one or more of: check plan repository 210, data repository 216, patient & check plan repository 136, trained personnel data repository 123 or any other location operatively connected to diagnostics device 104 on which patient data is stored) within the data received from the one or more navigation sensors. For example, if a throat medical examination is requested, diagnostics device activates one or more navigation sensors such as navigation camera 420, etc., and compares the received data relating to patient's 103 throat with relevant reference data (such as patient's throat image, nose image, etc.) stored on one or more of: check plan repository 210, data repository 216, patient & check plan repository 136, trained personnel data repository 123 or any other location operatively connected to diagnostics device 104 on which patient data is stored. When a match is found, diagnostics device 104 can calculate its relative spatial disposition with respect to the desired spatial disposition. Such calculated spatial disposition can be used as an origin point for performing the navigation process to enable medical data acquisition (in the example, medical data relating to patient 103 throat) using known methods and techniques. One exemplary, non-limiting method is comparing images acquired by navigation sensors (e.g. navigation camera 420) with known reference images. When a match is found the approximate spatial disposition can be calculated. It can be appreciated that images can appear at different positions, orientations and scaling factors, however there are some algorithms that can be utilized for compensating such differences, such as, for example, using Scale-Invariant Feature Transform (or SIFT algorithm), which was published by Lowe, David G. (1999) in "Object recognition from local scale-invariant features", doi: 10.1109/ICCV.1999.790410 or in U.S. Pat. No. 6,711,293, "Method and apparatus for identifying scale invariant features in an image and use of same for locating an object in an image", David Lowe's patent for the SIFT algorithm.

Following calculation of diagnostics device 104 relative spatial disposition with respect to the desired spatial disposition, diagnostics device 104 can be configured to start the navigation and guiding process (step 818).

If a match is found and diagnostics device 104 successfully calculated its current spatial disposition with respect to the desired spatial disposition, diagnostics device 104 can be configured to notify user 102 (step 812) and lock the current spatial disposition as a starting point for the navigation process (step 814). If no match is found, for example after a pre-defined time period (e.g. 15 seconds), diagnostics device 104 can be configured to check for errors (e.g. validate that navigation sensors are operative, validate that reference data is available, etc.) and notify user 102 of the failure to find a match (step 808). If diagnostics device 104 fails to find any error related to it, diagnostics device 104 can be configured to return to step 806 and search again for known reference points. If diagnostics device 104 found an error related to it, diagnostics device 104 can be configured to notify user 102 of the error and, if the error has been handled, diagnostics device 104 can be configured to enable user 102 to return to step 806 and search again for known reference points (step 810).

Figure 12:
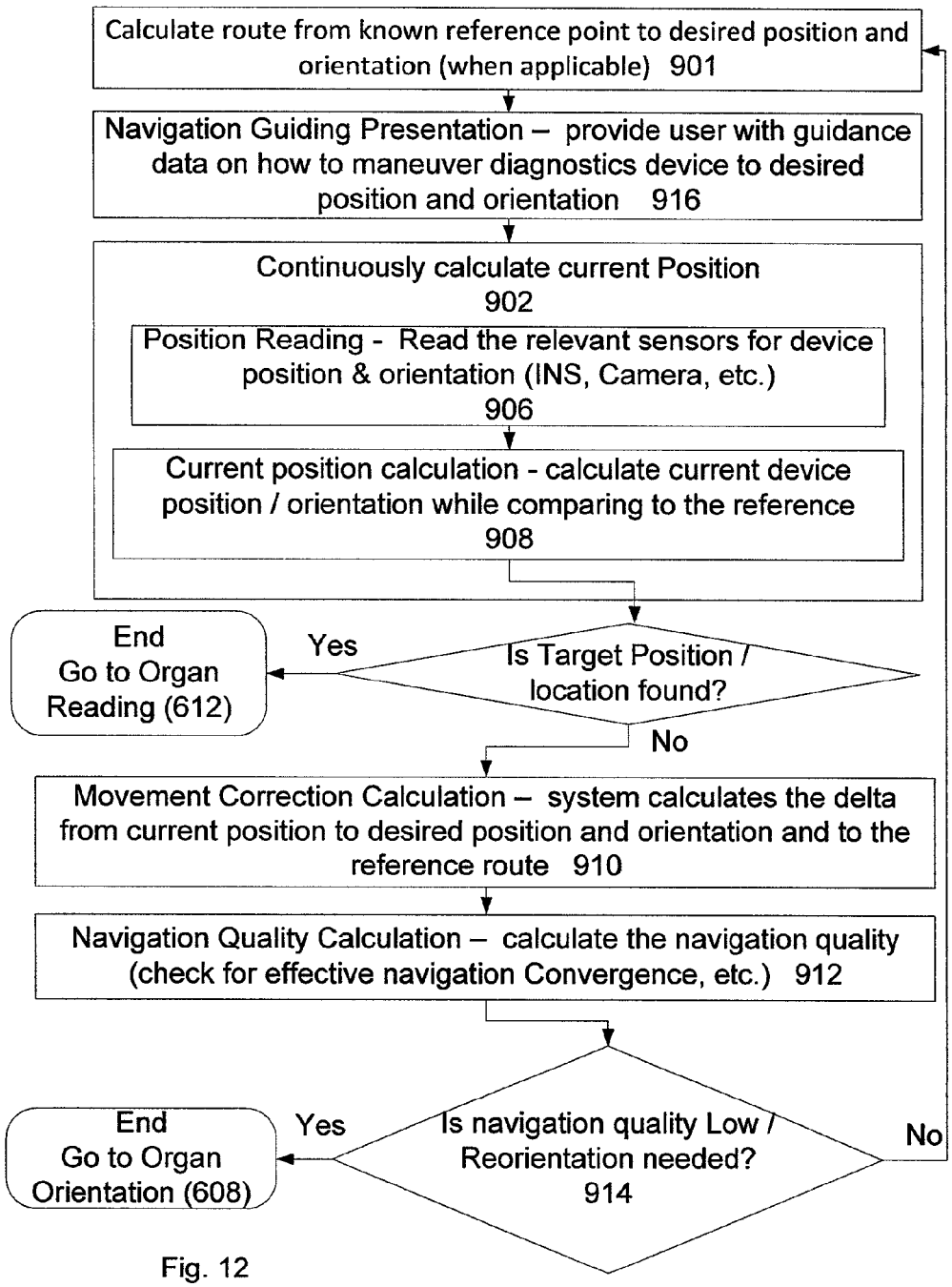
FIG. 12 is a flowchart illustrating one example of a sequence of operations carried out for navigating a diagnostic device and guiding a diagnostic device user accordingly, in accordance with the presently disclosed subject matter.

FIG. 12 is a flowchart illustrating one example of a sequence of operations carried out for navigating a diagnostic device and guiding a diagnostic device user accordingly, in accordance with the presently disclosed subject matter. Diagnostics device 104, for example by utilizing navigation module 204, can be configured to calculate a route from a known reference point that was found (see for example FIG. 11), to the desired diagnostics device 104 spatial disposition with respect to patient's 103 body (or a specific part thereof) (step 901). The route calculation can be performed, for example, by utilizing known methods and techniques. A route calculation can be performed, for example, by calculating the distance and required movement correction between the current diagnostic device 104 position (X1, Y1, Z1), as identified by utilizing the reference data (see FIG. 11) to the target diagnostic device 104 position as defined by the reference data (X2, Y2, Z2). The distance can be calculated using known techniques such as subtracting the values of each axis (such as Xd=X1−X2, etc.). The result value of each axis can be defined as the required correction of diagnostic device 104 position. In addition, the system can calculate the required rotation correction to diagnostic device 104 orientation using Yaw, Pitch and Roll rotation calculation techniques as known in the art. Following route calculation, diagnostics device 104, for example by utilizing guiding module 206, can be configured to provide user 102 with guidance data instructing user 102 how to maneuver diagnostics device 104 to the desired diagnostics device 104 spatial disposition with respect to patient's 103 body (or a specific part thereof) (step 916). For this purpose, diagnostics device can be configured to present user 102 with the current spatial disposition with respect to patient's 103 body (or a specific part thereof) of diagnostics device 104, for example as detailed with respect to FIG. 13 above. Diagnostics device can also be configured to provide user 102 with voice instructions instructing user 102 on how to maneuver diagnostics device 104. It is to be noted that, as indicated above, other instruction methods can be utilized as well (e.g. diagnostics device 104 vibrations, etc.).

Diagnostics device 104 can be further configured to continuously calculate its current spatial disposition with respect to the desired spatial disposition (step 902). During continuous or periodic position and orientation calculation, diagnostics device 104 can be configured to continuously receive data from one or more navigation sensors such as INS sensors 410, navigation camera 420, pressure sensors 440, distance sensors 430, etc. (step 906) and continuously calculate its current spatial disposition with respect to patient's 103 body (or a specific part thereof) by means of comparison of the data received from the one or more navigation sensors with the reference data (e.g. reference image, reference INS data, etc.), for example by using known methods and techniques (step 908). One exemplary, non-limiting method is utilizing INS sensors 410 data for computing diagnostics device 104 trajectory according to gyro and accelerometer information. The mathematics is based on a solution of 6 Degrees Of Freedom equations as described in various papers and books (for example "Strapdown Inertial Navigation Technology", D. Titterton and J. Weston, ISBN 1563476932). In order to overcome error accumulation that can occur with time and which can affect precision, the diagnostics device 104 spatial disposition with respect to patient's 103 body (or a specific part thereof) can be further calculated according to image comparison as detailed above. Thus, the diagnostics device 104 spatial disposition with respect to patient's 103 body (or a specific part thereof) can be constantly or periodically computed by utilizing the INS sensors 410 data (by determining diagnostics device velocity and position) while utilizing image comparison in order to eliminate errors (e.g. by matching reference points). The INS sensors 410 data and the image comparison data can be merged for example by using Kalman Filtering which is an exemplary algorithm for information fusion.

Figure 14:
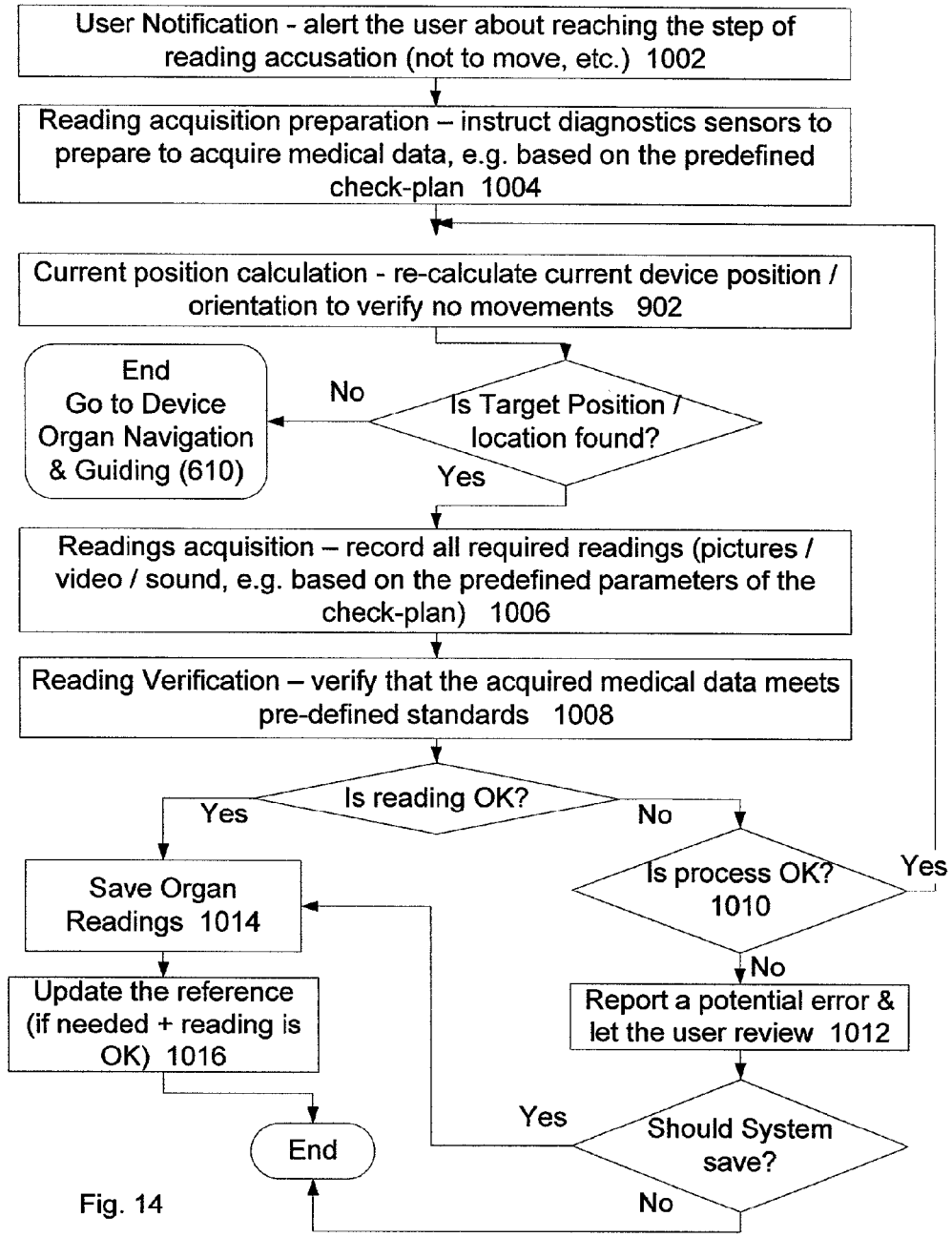
FIG. 14 is a flowchart illustrating one example of a sequence of operations carried out for acquisition and verification of a reading by a diagnostic device, in accordance with the presently disclosed subject matter.

If diagnostics device 104 current spatial disposition with respect to patient's 103 body (or a specific part thereof) is the desired diagnostics device 104 spatial disposition with respect to patient's 103 body (or a specific part thereof), diagnostics device can be configured to acquire patient 103 medical data, as further detailed, inter alia, with respect to FIG. 14. However, if diagnostics device 104 current spatial disposition with respect to patient's 103 body (or a specific part thereof) is not the desired diagnostics device 104 spatial disposition with respect to patient's 103 body (or a specific part thereof), diagnostics device 104 can be configured to perform a movement correction calculation (step 910). During movement correction calculation, diagnostics device 104 can be configured to calculate the delta between its current spatial disposition with respect to patient's 103 body (or a specific part thereof) and the desired spatial disposition with respect to patient's 103 body (or a specific part thereof), and/or the calculated route. Movement correction calculation can be based, for example, on data received from the one or more navigation sensors and the calculated route. In such cases, after a route is calculated, diagnostics device 104 can be configured to check if the actual movements made by it do not fit the expected movements calculated during route calculation. Alternatively movement correction calculation can be based on re-comparing the data received from the one or more navigation sensors and the respective reference data.

Diagnostics device 104 can be further configured to perform a navigation quality calculation (step 912). Diagnostics device 104 can be configured to check various parameters indicative of the navigation quality, such as convergence (check that the distance from the desired spatial disposition is getting smaller), etc. In case the navigation quality meets the requirements (e.g. the distance to the desired spatial disposition is getting smaller, etc.), diagnostics device returns to step 916 in order to continue the navigation and guiding process. If, however, the navigation quality does not meet the requirements, diagnostics device 104 can be configured to return to step 608 and perform device re-orientation.

Figure 12A:
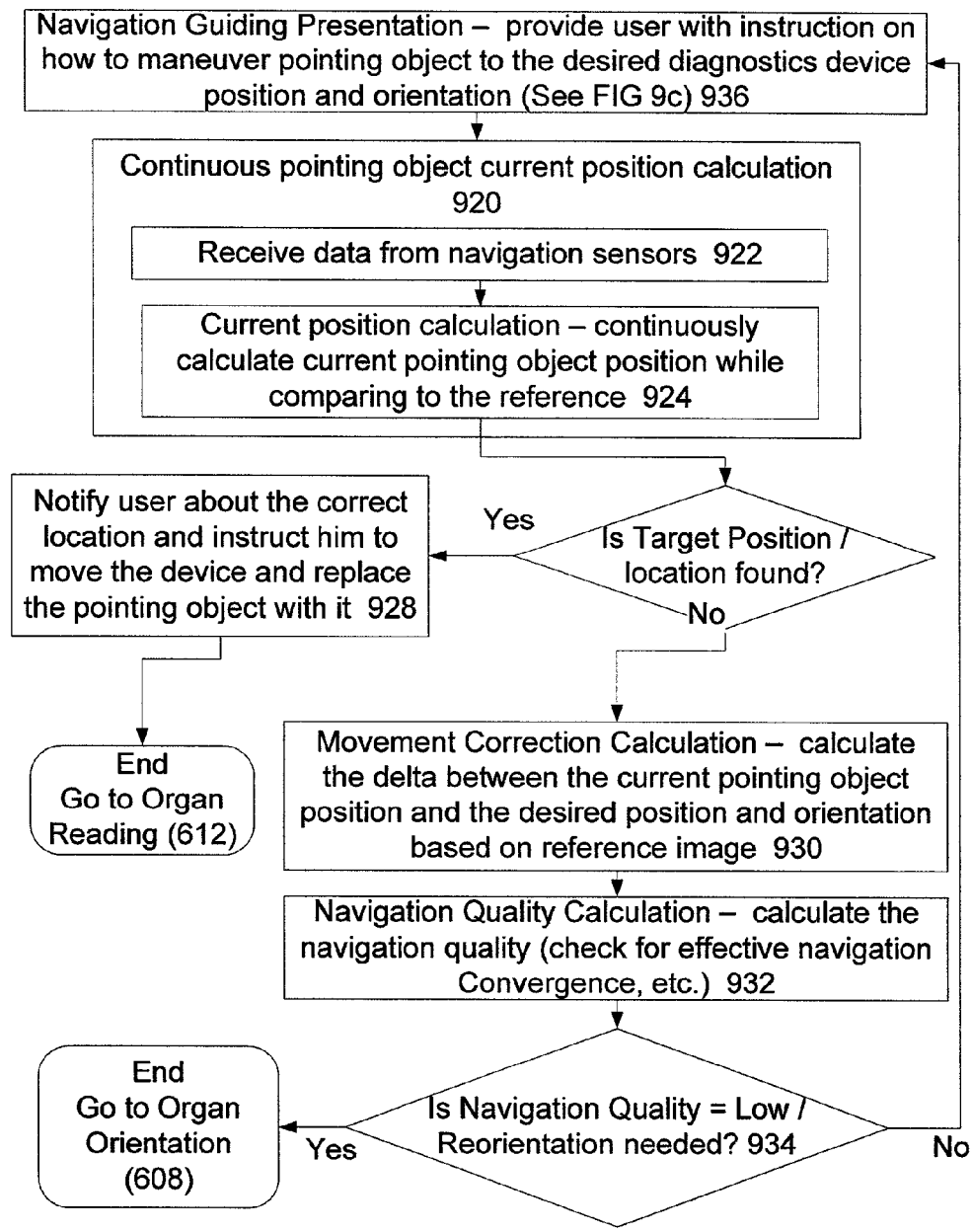
FIG. 12a is a flowchart illustrating another example of a sequence of operations carried out for navigating a diagnostic device and guiding a diagnostic device user accordingly, in accordance with the presently disclosed subject matter.
Figure 12B:
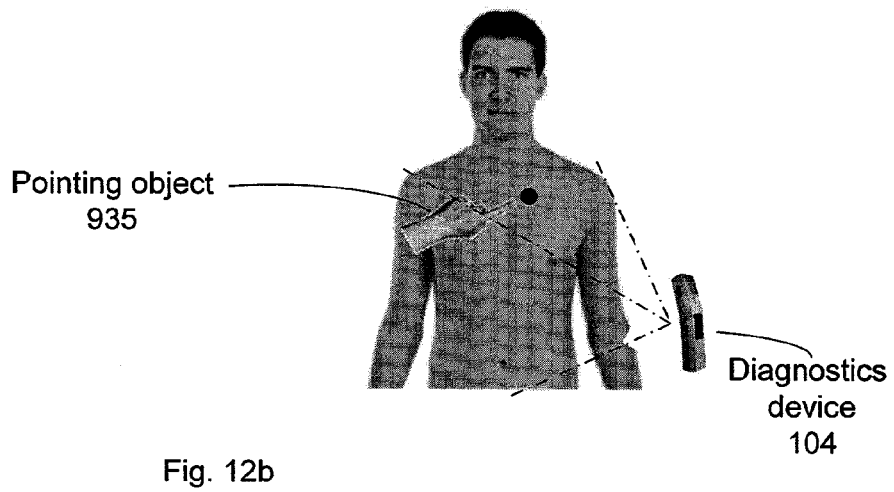
FIG. 12b is a schematic illustration of an exemplary pointing object used for navigating a diagnostic device and guiding a diagnostic device user accordingly, in accordance with the presently disclosed subject matter.

FIG. 12a is a flowchart illustrating another example of a sequence of operations carried out for navigating a diagnostic device and guiding a diagnostic device user accordingly, in accordance with the presently disclosed subject matter. Also in this example diagnostics device 104, for example by utilizing navigation module 204, can be configured to calculate a route from a known reference point that was found (see for example FIG. 11), to the desired diagnostics device 104 spatial disposition with respect to patient's 103 body (or a specific part thereof). However, in the current example user 102 initially points to a certain place on patient 103 body with pointing object 935 (for example user 102 finger, etc.) and the route is calculated while utilizing the initial location of pointing object 935 as the starting point. Looking at FIG. 12b there is shown a schematic illustration of an exemplary pointing object used for navigating a diagnostic device and guiding a diagnostic device user accordingly, in accordance with the presently disclosed subject matter. It can be appreciated that pointing object 935 points to a certain location on patient 103 body while diagnostics device 104 utilizes one or more navigation sensors as further detailed below for calculating pointing object location and a route from the pointing object location to the desired diagnostics device 104 spatial disposition with respect to patient's 103 body (or a specific part thereof).

Returning to FIG. 12a, following route calculation, diagnostics device 104, for example by utilizing guiding module 206, can be configured to provide user 102 with guidance data instructing user 102 how to maneuver pointing object 935 to the desired diagnostics device 104 spatial disposition with respect to patient's 103 body (or a specific part thereof) (step 936). For this purpose, diagnostics device can be configured to present user 102 with the current location of pointing object 935. Diagnostics device can also be configured to provide user with voice instructions instructing user 102 on how to maneuver pointing object 935. It is to be noted that, as indicated above, other instruction methods can be utilized as well (e.g. diagnostics device 104 vibrations, etc.).

Diagnostics device 104 can be further configured to continuously calculate pointing object 935 current location with respect to its desired location (step 920). During continuous pointing object 935 location calculation, diagnostics device 104 can be configured to continuously receive data from one or more navigation sensors such as navigation camera 420, distance sensors 430, etc. (step 922) and continuously calculate pointing object 935 current location by means of comparison of the data received from the one or more navigation sensors with the reference data (e.g. reference image, etc.), for example by using known methods and techniques as detailed above (step 924).

If pointing object 935 current location is the desired diagnostics device 104 spatial disposition with respect to patient's 103 body (or a specific part thereof), diagnostics device can be configured to instruct user 102 to move diagnostics device 104 to the location indicated by pointing object 935 (step 928) and acquire patient 103 medical data, as further detailed, inter alia, with respect to FIG. 14. However, if pointing object 935 current location is not the desired diagnostics device 104 spatial disposition with respect to patient's 103 body (or a specific part thereof), diagnostics device 104 can be configured to perform a movement correction calculation (step 930). During movement correction calculation, diagnostics device 104 can be configured to calculate the delta between pointing object 935 current location and its desired location, and/or the calculated route. Movement correction calculation can be based, for example, on data received from the one or more navigation sensors and the calculated route. In such cases, after a route is calculated, diagnostics device 104 can be configured to check if the actual movements made by pointing object 935 do not fit the expected movements calculated during route calculation. Alternatively movement correction calculation can be based on re-comparing the data received from the one or more navigation sensors and the respective reference data.

Diagnostics device 104 can be further configured to perform a navigation quality calculation (step 932). Diagnostics device 104 can be configured to check various parameters indicative of the navigation quality, such as convergence (check that the distance of pointing object 935 from its desired location is getting smaller), etc. In case the navigation quality meets the requirements (e.g. the distance of pointing object 935 from its desired location is getting smaller, etc.), diagnostics device returns to step 936 in order to continue the navigation and guiding process. If, however, the navigation quality does not meet the requirements, diagnostics device 104 can be configured to return to step 608 and perform device re-orientation.

It is to be noted that other navigation methods for navigating diagnostics device 104 can be utilized as well.

FIG. 14 is a flowchart illustrating one example of a sequence of operations carried out for acquisition and verification of a reading by a diagnostic device, in accordance with the presently disclosed subject matter. Diagnostics device 104, for example by utilizing reading and verification logic module 212, can be configured, for example upon arrival to desired diagnostics device 104 spatial disposition with respect to patient's 103 body (or a specific part thereof) (e.g. spatial disposition with respect to patient's 103 body (or a specific part thereof) that enable medical data acquisition, as detailed above), to notify user 102 that it is located in the desired spatial disposition with respect to patient's 103 body (or a specific part thereof) and about to start taking the reading (step 1002). Diagnostics device 104 can be further configured to instruct diagnostics sensor module 202 to prepare to acquire medical data of patient 103 (step 1004). Such preparations can include preparing diagnostics sensors 202 to acquire medical data according to the patient specific check plan. Exemplary preparations are setting image acquisition sensor 316 zoom, activating light sources 318 at correct power, activating sound acquisition sensor 324, etc. In addition diagnostic device 104 can be configured to retrieve the relevant reading parameters and thresholds for example from the patient specific check plan (e.g. the required length of reading, reference thresholds such as minimal sound volume, etc.).

Diagnostics device 104 can also be configured to recalculate its current spatial disposition with respect to patient's 103 body (or a specific part thereof) and verify that no movements have been made and that it is still located in the desired spatial disposition (step 902). In case there has been a change in diagnostics device 104 spatial disposition with respect to patient's 103 body (or a specific part thereof), diagnostics device 104 can be configured to return to the navigation and guiding process (610). Otherwise, diagnostics device 104 can be configured to perform medical data acquisition (step 1006). The medical data can be acquired according to the check plan, that, as indicted above, can include information, inter alia about the examination process, steps and logic, and predefined reading parameters such as type of sensor to be used (still image vs. video), required length of reading (sound or video recording) in terms of time (e.g. seconds), and reading data thresholds (for example definition of acceptable minimal and/or maximal reading limits to be used as a quality parameter of a reading. Thus, for example, if the heart is to be checked, the check plan can define that the sound based sensors 320 are to be used and that the reading length should be 3 seconds, or between 2.5 and 5 seconds, etc.).

Following medical data acquisition, diagnostics device 104 can be configured to verify that the acquired medical data meets pre-defined standards (e.g. a required length of reading, reading data thresholds, etc.) (step 1008). For example, if the heart is to be checked, and the check plan defines that the reading length should be between 2.5 and 5 seconds, diagnostics device 104 can be configured to check that the reading length meets the requirement. In case the acquired medical data did not meet the pre-defined standards, diagnostics device 104 can be configured to check if the reading acquisition process was ok (step 1010) (for example that the diagnostics sensors 202 are operative, that the check plan data and the reference data were successfully retrieved, that the navigation and guidance processes succeeded, etc.). If the process was ok, diagnostics device 104 can be configured to return to step 902 (in order to retry acquiring the medical data). If the process was not ok, diagnostics device 104 can be configured to issue a notification to user 102 (for example by presenting a message on diagnostic device 104 or patient workstation 114, etc.) and enable him to review the acquired medical data, if any (step 1012). Diagnostics device 104 can be further configured to enable user 102 to decide if the acquired medical data is to be saved or not.

If user 102 chooses to save the acquired medical data, or the reading acquisition process was ok, diagnostics device 104 can be configured to save the acquired medical data (for example, in one or more of: data repository 216, patient & check plan repository 136, trained personnel data repository 123 or any other location operatively connected to diagnostics device 104 on which patient data is stored) (step 1014).

Optionally, in case the reading acquisition process was ok, diagnostics device 104 can be configured to update the reference data with the acquired medical data (step 1016). This can be performed in order to keep the reference data up to date, as changes can occur to the human body (for example in light of growing up, aging, medical treatments, etc.).

We will now turn to describe another embodiment of the system, in which parts of the functionality described above as performed by diagnostics device 104 is performed by trained personnel 124. It is to be noted that relevant changes to diagnostics device 104 in comparison to the embodiment described above are mentioned below. As indicated above, it is to be noted that identical reference numerals indicate those components that are common to different embodiments or configurations.

Figure 15:
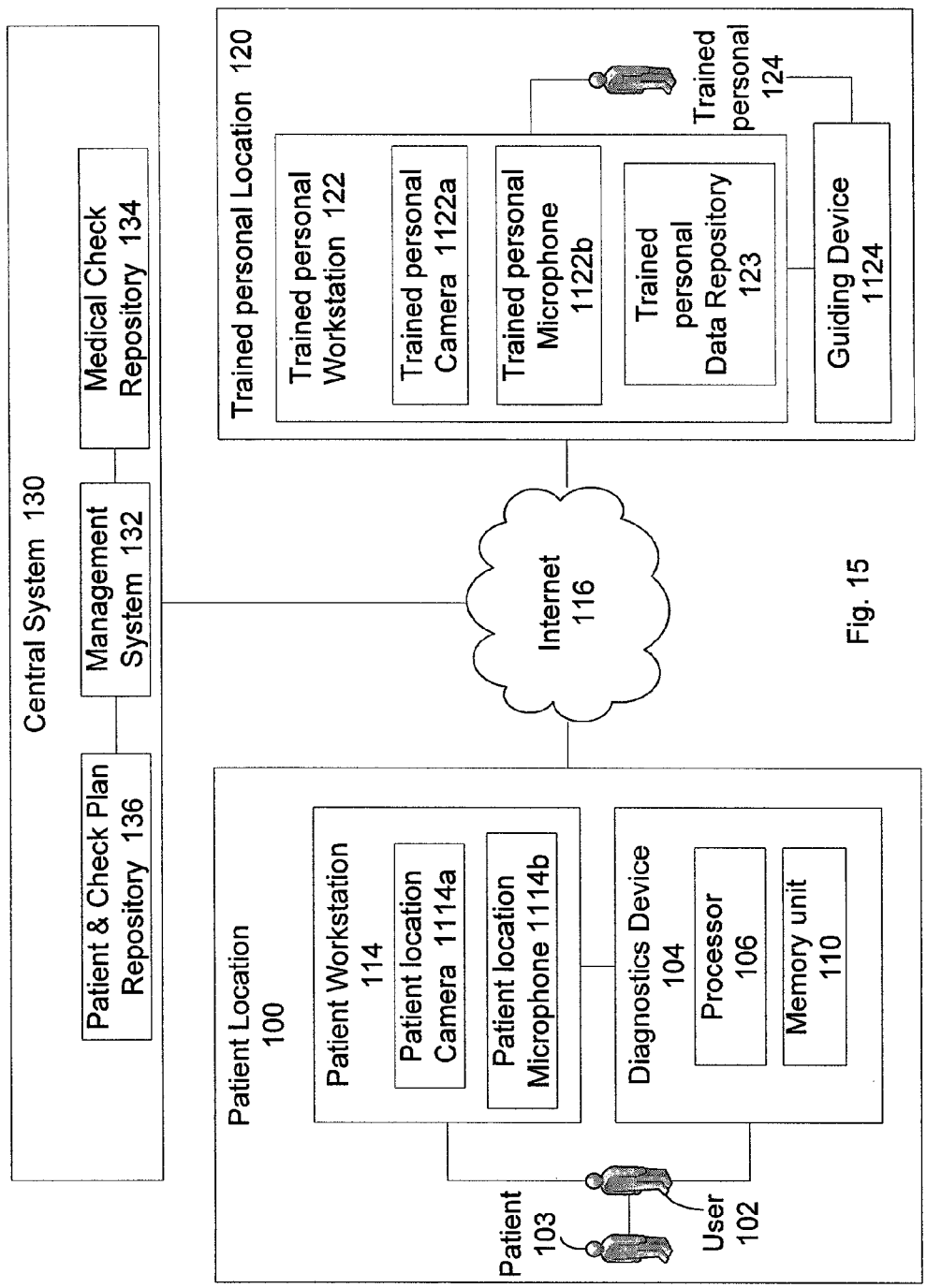
FIG. 15 is a block diagram schematically illustrating one example of a system for performing an automatic and remote trained personnel guided medical examination, in accordance with the presently disclosed subject matter.

FIG. 15 is a block diagram schematically illustrating one example of a system for performing an automatic and remote trained personnel guided medical examination, in accordance with the presently disclosed subject matter. As detailed above, it can be appreciated that user 102 and patient 103 are located at patient location 100. User 102 can in some cases be patient 103 whose medical examination is required (in such cases, even though user 102 and patient 103 are shown as separate entities in the drawings, they are in fact the same entity). In other cases, user 102 can be a person that will be performing the medical examination of patient 103.

As detailed above, for the purpose of performing a medical examination, user 102 operates a diagnostic device 104, as further detailed below. In some cases, user 102 also operates a patient workstation 114, as further detailed below. Patient workstation 114 can be any computer, including a personal computer, a portable computer, a cellular handset or an apparatus with appropriate processing capabilities, including a computer and/or an apparatus which can be, for example, specifically configured for that purpose. Patient workstation 114 can further comprise patient location camera 1114a and patient location microphone 1114b, that can be used, inter alia, for acquiring image (including video) and sound data of patient 103. Such data can be used by trained personnel 124 for example for viewing and hearing patient 103 and/or user 102 and/or diagnostic device 104 by trained personnel 124 as well as allowing video conferencing, as further detailed below. It is to be noted that in some cases, patient workstation 114 can be incorporated within diagnostics device 104. Diagnostics device 104 comprises (or is otherwise associated with) at least one processor 106 (e.g. digital signal processor (DSP), a microcontroller, a field programmable gate array (FPGA), an application specific integrated circuit (ASIC), etc.) and a memory unit 110 (e.g. ROM, hard disk, etc.). Processor 106 is configured to receive instructions and control the components and operations of diagnostics device 104.

As detailed above, in some cases diagnostics device 104 can be configured to communicate with patient workstation 114. The communication between diagnostics device 104 and patient workstation 114 can be realized by any communication means, e.g. via wired or wireless communication. It can be noted that user 102, patient 103, diagnostics device 104 and patient workstation 114 are located at patient location 100.

Diagnostics device 104 can be configured to enable acquisition of various data as further detailed below. The acquired data can be transmitted (directly from diagnostics device 104 or through patient workstation 114) to trained personnel workstation 122 located at trained personnel location 120 and/or to central system 130. Central system 130 and trained personnel workstation 120 can be any computer, including a personal computer, a portable computer, a cellular handset or an apparatus with appropriate processing capabilities, including a computer and/or an apparatus which can be, for example, specifically configured for that purpose. The acquired data can be transmitted for example via Internet 116. It is to be noted that the data can be transmitted while utilizing other known communication alternatives, such as a cellular network, VPN, LAN, etc.

As detailed above, central system 130 comprises patient & check plan repository 136 in which various data relating to the patient is maintained. Such data can include, for example, patient identification number, patient name, patient age, patient contact details, patient medical data (such as diseases, sensitivities to medicines, etc.), check plans data (as further detailed below), etc. Central system 130 can further comprise a medical examination repository 134 in which data acquired by diagnostics device 104, patient workstation 114 and trained personnel workstation 122 is maintained. Such data can include, for example, results of medical examinations performed using diagnostics device 104 (such as ear recorded images and video readings, lungs or heart recorded sound, blood pressure, body temperature, etc. as further detailed below). Central system 130 can further comprise management system 132, that can be configured to establish a connection between a selected trained personnel workstation 122 (for example an available trained personnel workstation 122 or trained personnel workstation 122 with the shortest queue) and diagnostics device 104 and/or patient workstation 114. It is to be noted that when providing a central system, there may be more than one trained personnel location 120 and trained personnel 124 as central system 130 allows for a distributed approach in which data can be received by central system 130 from multiple patient locations and transferred to multiple trained personnel locations, for example in order to establish connections between trained personnel workstations and patient workstations and/or diagnostics devices. The connection can be a direct connection or a connection via central system 130, and it can be established e.g. via Internet 116. It is to be noted that other known connection alternatives can be utilized, such as a cellular network, VPN, LAN, etc.). In some cases, management system 132 can also manage other processes such as, subscribing patients, planning scheduling of patients to available trained personnel, managing patient and check plan repository 136, viewing and analyzing medical examination repository 134, etc.

It is to be noted that central system 130 is optional to the solution and that central system 130 can be part of any trained personnel system 120, In addition the communication between trained personnel workstation 122 and diagnostics device 104 and/or patient workstation 114 (also referred to hereinafter as: "tp-patient connection") can be implemented directly without the use of, or need for, a central system 130. It is also to be noted that tp-patient connection can be implemented using a distributed approach i.e. multiple patients can be served by one trained person and/or one patient can be served by multiple trained persons. In such case, patient workstation 114 can include for example a local repository containing one or more connections information to a relevant trained personnel workstation 122, and vice-versa.

When the transmitted data (including image and voice data of patient 103) is received at trained personnel workstation 122, the data can be displayed on trained personnel workstation 122. For that purpose, trained personnel workstation 122 can include, inter alia, a display (e.g. LCD screen). It is to be noted that the image and voice data of patient 103 can be streamed to trained personnel workstation 122. Trained personnel 124 can view the received data on display and provide user 102 with navigational directions for navigating diagnostics device 104 to a desired spatial disposition with respect to patient's 103 body (or a specific part thereof) from which medical data is to be acquired. For this purpose, trained personnel workstation 122 can comprise trained personnel camera 1122a and trained personnel microphone 1122b that can be used for acquiring image (including video) and sound data of trained personnel 124. It is to be noted that during the tp-patient connection a video conference can take place while utilizing, for example, patient location camera 1114a, patient location microphone 1114b, trained personnel camera 1122a, and trained personnel microphone 1122b. In such cases the data received from trained personnel camera 1122a and trained personnel microphone 1122b, can be presented to user 102 utilizing for example a patient workstation 114 display and speaker using for example video-conference software.

For the purpose of providing navigation instructions to user 102, trained personnel workstation 122 can be further connected to guiding device 1124 (e.g. via a wired or wireless connection). Guiding device 1124 can be any input mean that will enable trained personnel 124 to provide user 102 with six axis movement instructions (up-down, left-right, back-forward, pitch, roll, yaw), as further detailed below, inter alia with respect to FIG. 16. As trained personnel 124 provides the navigation instructions to user 102 utilizing guiding device 1124, the instructions are transmitted to patient workstation 114 or to diagnostics device 104. Patient workstation 114 or diagnostics device 104 can be configured to present the instructions to user 102, for example visually on a display (e.g. LCD screen included in patient workstation 114 or diagnostics device 104). Another exemplary alternative is to present the instructions to user 102 vocally while translating the received data to voice commands (using known methods and techniques).

Upon arrival to a desired diagnostics device 104 spatial disposition with respect to patient's 103 body (or a specific part thereof), trained personnel 124 can instruct user 102 to acquire medical data using diagnostics device 104. In addition, trained personnel workstation 122 and/or guiding device 1124 can enable trained personnel 124 to acquire the required medical data by themselves. In such a case, trained personnel workstation 122 and/or guiding device 1124 will transfer trained personnel 124 instruction to diagnostic device 104, which will automatically acquire the required readings based on the received instructions. It is to be noted that trained personnel workstation 122 and/or guiding device 1124 and/or diagnostic device 104 can also be configured to use the predefined reading acquisition parameters, as defined in check plan repository 210 and/or patient and check plan repository 136 or any other location operatively connected to trained personnel workstation 122 and/or guiding device 1124 and/or diagnostic device 104 on which patient data is stored. After medical data is acquired, diagnostics device can be configured to transmit the acquired data to trained personnel workstation 122 and/or to central system 130. When the transmitted data is received at trained personnel workstation 122, the data can be saved in trained personnel data repository 123 that can be connected to trained personnel workstation 122. Trained personnel 124 (e.g. a doctor, a nurse, a medic, etc., including any other person skilled to analyze the transmitted data), located at trained personnel location 120, and/or at central system 130, can retrieve and review the acquired data, for example using trained personnel workstation 122. It is to be noted that patient workstation 114, trained personnel workstation 122 and central system 130 can include a display (e.g. LCD screen), and a keyboard or any other suitable input/output devices. In some cases, trained personnel 124 can provide feedback to user 102, for example by transmitting data back to patient workstation 114. Such feedback can include, for example, analysis of the received data, request to receive more data, medical treatment instructions, invitation to a further examination, etc. Alternatively or additionally, trained personnel 124 can transmit feedback data to central system 130, which, in turn, can transmit the feedback data to patient workstation 114 (e.g. via the Internet, cellular network, etc.).

Figure 16:
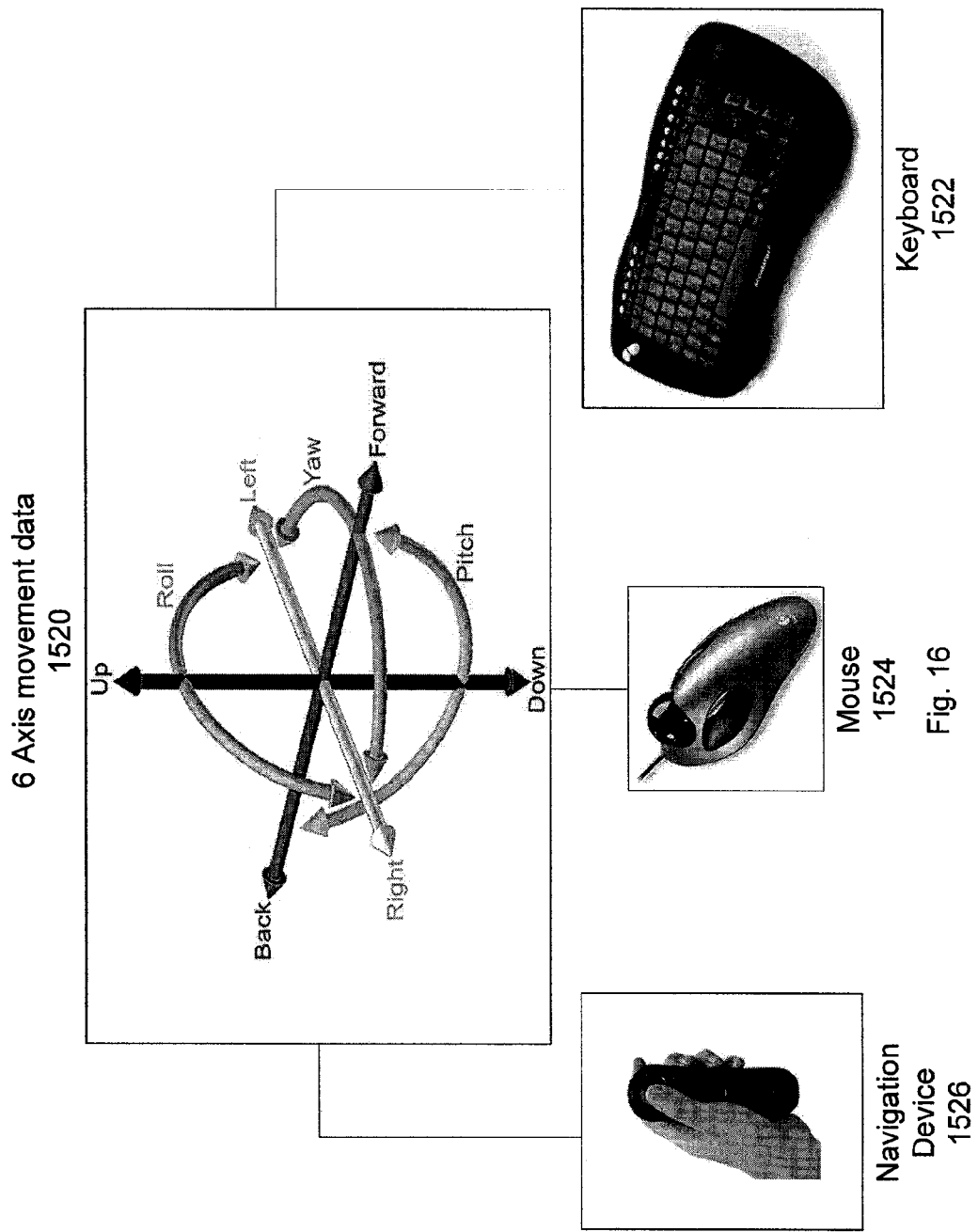
FIG. 16 is a schematic illustration of some exemplary guiding devices that can be used for providing navigation instructions to a user of a diagnostic device, in accordance with the presently disclosed subject matter.

FIG. 16 is a schematic illustration of some exemplary guiding devices that can be used for providing navigation instructions to a user of a diagnostic device, in accordance with the presently disclosed subject matter. Guiding device 1124 can be, for example, keyboard 1522, mouse 1524, navigation device 1526, etc. it can be appreciated that keyboard 1522 can enable trained personnel 124 to provide 6-axis movement data 1520 to user 102 as indicated above. For example, keyboard 1522 can have a trackball that enables providing, for example, pitch, yaw and roll movement, arrow keys that enable for example up-down and left-right movement and other key or keys that enable back-forward motion. It is to be noted that this is a mere example as other keys can be used and other functionality can be defined for the trackball and for the keys. In some cases, the trackball is optional and keyboard keys can perform its functionality. As another example, mouse 1524 can be utilized. In such cases, mouse movement can enable for example up-down and left-right movement while mouse 1524 can have an additional trackball for enabling, for example, pitch, yaw and roll movement. Back-forward motion can be represented for example by pressing a mouse key and moving the mouse backwards and forwards. It is to be noted that this is a mere example as other keys can be used and other functionality can be defined for the trackball, the mouse and the mouse keys. As a further example, navigation device 1526 can be used. Navigation device 1526 can comprise, for example, INS sensors or any other mean that enables identifying navigation device 1526 motion, e.g. in 6 degrees of freedom.

Figure 17:
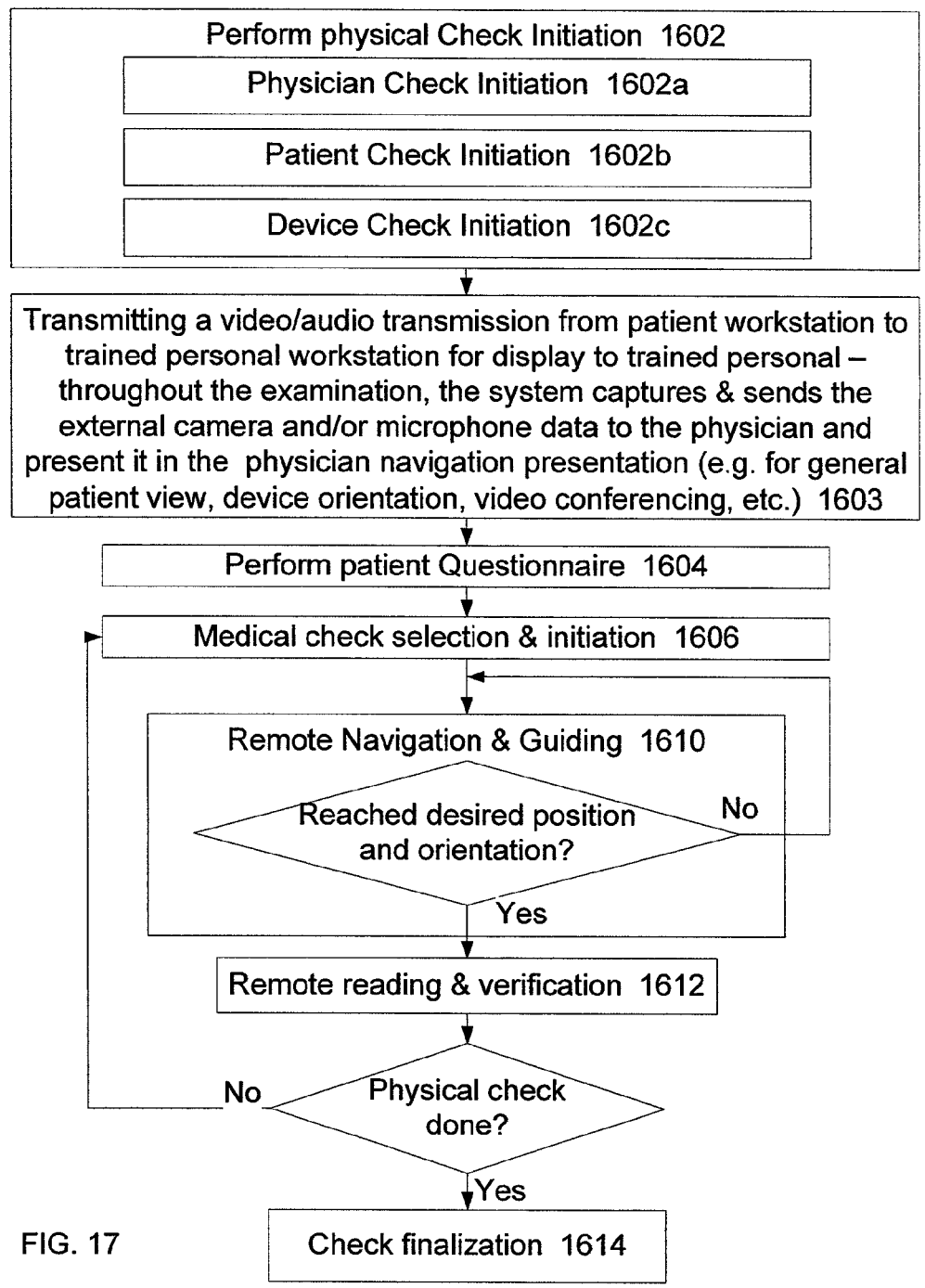
FIG. 17 is a flowchart illustrating one example of a sequence of operations carried out for performing an automatic and remote trained personnel guided medical examination, in accordance with the presently disclosed subject matter.

FIG. 17 is a flowchart illustrating one example of a sequence of operations carried out for performing an automatic and remote trained personnel guided medical examination, in accordance with the presently disclosed subject matter. The process begins with performance of a physical check initiation (step 1602). Physical check initiation can include establishing and verification of a tp-patient connection and can include one or more of the following initiations: trained personnel check initiation 1602a, patient check initiation 1602b and device check initiation 1602c. Trained personnel check initiation 1602a can include activating trained personnel workstation 122, including the display, the trained personnel camera 1122a, the trained personnel microphone 1122b and optionally guiding device 1124. Trained personnel check initiation 1602a can further include retrieving relevant details relating to patient 103 (e.g. from one or more of: data repository 216, check plan repository 210, trained personnel data repository 123, patient & check plan repository 136 or any other location operatively connected to trained personnel workstation 122 on which patient data is stored) and displaying all or part of the retrieved details on trained personnel workstation 122 (e.g. on a display). The retrieved data can include data relating to a patient specific check plan, reading references, communication parameters, etc. Trained personnel check initiation can further include displaying data received from patient workstation 114 or diagnostics device 104, including image and voice data received (e.g. streamed) from one or more of patient location camera 1114a, patient location microphone 1114b, diagnostics sensors 202 of diagnostics device 104, navigation camera 420 of diagnostics device 104, etc. Trained personnel check initiation 1602a can further include retrieving relevant details relating to patient 103 from external systems such as visit scheduling system, Electronic Medical Record (EMR) system or any other system or repository, which are relevant to the patient's examination.

Patient check initiation 1602b can include activating patient workstation 114, including the display, patient location camera 1114a, patient location microphone 1114b and establishment and verification of a tp-patient connection. Patient check initiation 1602b can further include beginning to transmit (e.g. stream) data acquired by patient location camera 1114a and patient location microphone 1114b to trained personnel workstation 122, for example for displaying the acquired data to trained personnel 124. Patient check initiation 1602b can further include retrieving relevant details relating to patient 103 (e.g. from one or more of: data repository 216, check plan repository 210, patient & check plan repository 136 or any other location operatively connected to patient workstation 114 on which patient data is stored) and displaying all or part of the retrieved details on patient workstation 114 (e.g. on a display). The retrieved data can include data relating to a patient specific check plan, reading references, communication parameters, etc. patient check initiation 1602b can further include retrieving relevant details relating to patient 103 from external systems such as visit scheduling system, Electronic Medical Record (EMR) system or any other system or repository, which are relevant to the patient examination.

Device check initiation 1602c can include activating and checking the status of diagnostics device 104, including communication with patient workstation 114 and activation of one or more of diagnostic device 104 modules or sensors (e.g. diagnostics sensors 202 and/or navigation module 204 and/or guiding module and or/examination module). Device check initiation 1602c can further include the beginning of transmission (e.g. stream) of data acquired by diagnostics sensors 202 and/or navigation camera 420 to trained personnel workstation 122, for example for displaying the acquired data to trained personnel 124. It is to be noted that device check initiation 1602c can be performed, for example, by examination logic module 208.

Figure 19:
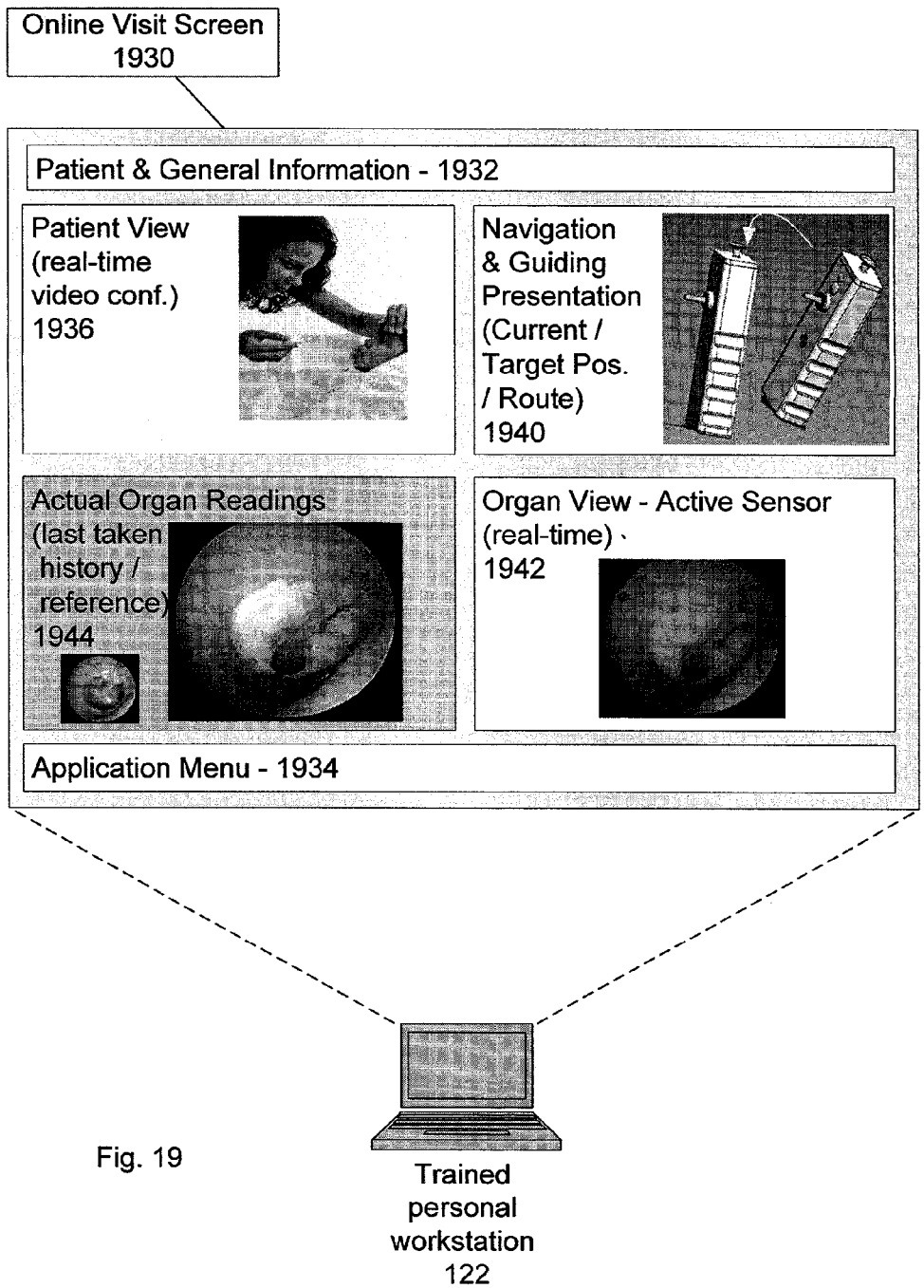
FIG. 19 is a schematic illustration of an exemplary navigation and guiding presentation to trained personnel, in accordance with the presently disclosed subject matter.

As indicated above, patient workstation 114 and diagnostics device 104 can be configured to periodically or continuously transmit (e.g. stream, for example using Internet 116, cellular network, etc.) data such as images, video and voice to trained personnel workstation 122 for purpose of displaying the data to trained personnel 124 (step 1603), an exemplary presentation on trained personnel workstation 122 display is provided with respect to FIG. 19. It is to be noted that trained personnel workstation 122 and patient workstation 114 can be configured to continuously or periodically transmit bi-directional video and audio both from patient workstation 114 to the trained personnel workstation 122 and vice versa (step 1603). This data transmission can be used for example for general patient view, device orientation & video conferencing, etc.

Trained personnel workstation 124 can be further configured to instruct trained personnel 124 to perform a questionnaire with respect to patient 103 (step 1604). The questionnaire can be a pre-defined questionnaire or a questionnaire defined by trained personnel on-the-go. The questionnaire can be presented to user 102 by trained personnel (for example utilizing trained personnel camera 1122a, trained personnel microphone 1122b), by patient workstation 114 (e.g. displaying the questions on patient workstation 114 display) or by any other means. User 102 can provide answers to the questionnaire utilizing patient location camera 1114a, patient location microphone 1114b, in which case trained personnel 124 will type the answers to the questionnaire in trained personnel workstation (e.g. using a keyboard). Alternatively user 102 can provide answers to the questionnaire by typing the answers in patient workstation 114 (e.g. using a keyboard). It is to be noted that other methods, such as voice recording, etc. can be utilized in order to provide answers to the questionnaire. The answers to the questionnaire can be stored for example in one or more of data repository 216, check plan repository 210, trained personnel data repository 123, patient & check plan repository 136 or any other location on which patient data is stored and that is operatively connected to trained personnel workstation 122.

A questionnaire can comprise generic and/or patient 103 specific questions designed to provide trained personnel 124 with a patient's medical data (e.g. data relating to patient 103 medical condition), including data required to enable analysis of the medical data acquired during the medical examinations (e.g. "does the patient have a fever and how long?", "how high is it?", "does the patient feel any pain?", "where is the pain located?", etc.).

Trained personnel workstation 122 can be further configured to perform a medical examination selection and initiation (step 1606). For that purpose, trained personnel workstation 122 can enable trained personnel 124 to select a medical examination to be performed, either manually or from a list of checks to be performed as defined in patient 103 check plan. Alternatively, trained personnel workstation 122 can select and initiate a check according to a pre-defined order set by patient 103 specific check plan, without input from trained personnel 124. The medical examination initiation can consist of, for example, retrieving reference medical examination data from the check plan or a relevant repository. The retrieved data can be displayed to trained personnel 124 on a display. An exemplary presentation on trained personnel workstation 122 display is provided with respect to FIG. 19. Medical examination initiation (step 1606) can also consist of sending relevant data to the patient workstation 114 and/or diagnostic device 104. Such data can include for example user instructions and general guiding information, patient instructions and general guiding information, diagnostic device parameters (e.g what check is currently being performed, required reading parameters, etc.), etc.

Following selection of a check, trained personnel workstation 122 can be configured to enable trained personnel 124 to provide user 102 with navigational instructions on how to navigate diagnostics device 104 to the desired spatial disposition with respect to patient's 103 body (or a specific part thereof) required for acquiring medical data (step 1610). Such desired spatial disposition with respect to patient's 103 body (or a specific part thereof) can be defined, for example, manually or by the patient specific check plan. Trained personnel 124 can view the data presented on trained personnel workstation 122 (including real-time or near real-time streaming data received from one or more of patient location camera 1114a, patient location microphone 1114b, diagnostics sensors 202, navigation module 204) and instruct trained personnel workstation 122 to provide user 102 with instructions for navigating diagnostics device 104 to the desired spatial disposition with respect to patient's 103 body (or a specific part thereof) for acquiring medical data of patient 103. For the purpose of providing the data to be presented on trained personnel workstation 122, diagnostics device 104 can be configured to utilize navigation module 204, including, inter alia, activating INS sensors 410, navigation light source 426, navigation camera 420, distance sensors 430, pressure sensors 440, etc., and transmit (e.g. stream) all or part of the data acquired by any of them.

As indicated above, the navigation instructions can be provided by voice commands (e.g. by transmitting data acquired by trained personnel microphone 1122b to patient workstation 114 or to diagnostic device 104). The navigation instructions can also be provided by utilizing guiding device 1124 that enables trained personnel 124 to perform the navigation and device spatial disposition correction virtually on trained personnel location 120. In such cases, the navigation performed by trained personnel 124 utilizing guiding device 1124 is analyzed and translated to voice commands that can be displayed to user 102. Alternatively or additionally the navigation performed by trained personnel 124 utilizing guiding device 1124 is presented to user 102 visually on patient workstation 114 (e.g. on patient workstation 114 display). In cases where the data is presented visually, the movements made by trained personnel 124 using guiding device 1124 can be presented to user 102 using a representation of diagnostics device 104, such as, for example, shown in FIG. 13. It is to be noted that the voice and/or visual navigation instructions can be managed by guiding module 206 (e.g. speaker 510, display 502, etc.) of diagnostics device 104 or by patient workstation 114.

It is to be noted that in some cases, diagnostics device 104 can be configured to utilize INS sensors 410 for verifying that diagnostics device 104 movements performed by user 102 are in-line with the navigational instructions provided by trained personnel 124. In such cases, if there is a mismatch between diagnostics device 104 movements made by user 102 and the navigational instructions provided by trained personnel 124, diagnostics device 104 can be configured to notify user 102 of the mismatch, and present him with the required movement correction. Such notification can be a voice notification (for example using speaker 510), a vibration notification (for example using vibration elements 508) or an image notification displayed (for example using navigation guiding presentation (as shown in FIG. 13) on patient location workstation 114 display or on display 502.

Upon arrival to diagnostics device 104 desired spatial disposition with respect to patient's 103 body (or a specific part thereof), trained personnel workstation 122 can be configured to enable trained personnel 124 to notify user 102 that diagnostics device 104 is in the required spatial disposition. Such notification can be a voice notification (e.g. utilizing trained personnel microphone 1122b). Alternatively or additionally a vibrating notification can be provided by diagnostics device 104 (for example using vibration elements 508) and/or a visual notification can be presented on patient workstation 114 or on display 502 (for example following receipt of an indication from trained personnel 124 that diagnostics device 104 is in the required spatial disposition that can be provided by trained personnel 124 to trained personnel workstation 122, e.g. utilizing keyboard, etc.). It is to be noted that other notification methods can be utilized as well.

Upon arrival to diagnostics device 104 desired spatial disposition with respect to patient's 103 body (or a specific part thereof), trained personnel workstation 122 can be configured to enable trained personnel 124 to perform a remote reading and verification of the reading 1612. For that purpose, trained personnel workstation 122 can be configured to enable trained personnel 124 to instruct diagnostics device 104 to acquire medical data of patient 103 (e.g. using manual instruction and/or utilizing reading and verification logic module 212 and using diagnostics sensors 202, inter alia as indicated above with respect to FIGS. 2 and 3). In response to receiving an instruction to acquire medical data, diagnostics device 104 can be configured to prepare for acquiring medical data of patient 103, to perform acquisition of such medical data and to transmit the acquired data to trained personnel workstation 122 for example for displaying the acquired data to trained personnel 124. Trained personnel workstation 122 can be configured to enable trained personnel 124 to verify that the acquired data is of sufficient quality (e.g. in terms of quality, thresholds, length, etc.). In case the acquired data is not of sufficient quality, trained personnel workstation 122 can be configured to enable trained personnel 124 to re-acquire the required data or if needed to instruct user 102 and provide navigational instructions to user 102 for repositioning and reorienting diagnostics device 104 in order to bring diagnostics device 104 to desired spatial disposition with respect to patient's 103 body (or a specific part thereof). Following repositioning and reorienting of diagnostics device 104, reading and verification can be re-performed.

Following reading acquisition and verification of patient 103 medical data, trained personnel workstation 122 can be configured to check if the medical examination is done (e.g. all medical examinations defined by patient 103 check plan have been performed). The check can be done either automatically by the trained personnel workstation 122 using the predefined check plan or manually by the trained personnel 124. In case the medical examination is not done, trained personnel workstation 122 can be configured to move to the next medical examination indicated by patient 103 check plan, or to allow the trained personnel 124 to do so manually. If all required medical examinations are performed, trained personnel workstation 122 can be configured to finalize the check, or to allow the trained personnel 124 to do so manually (step 1614).

Figure 18:
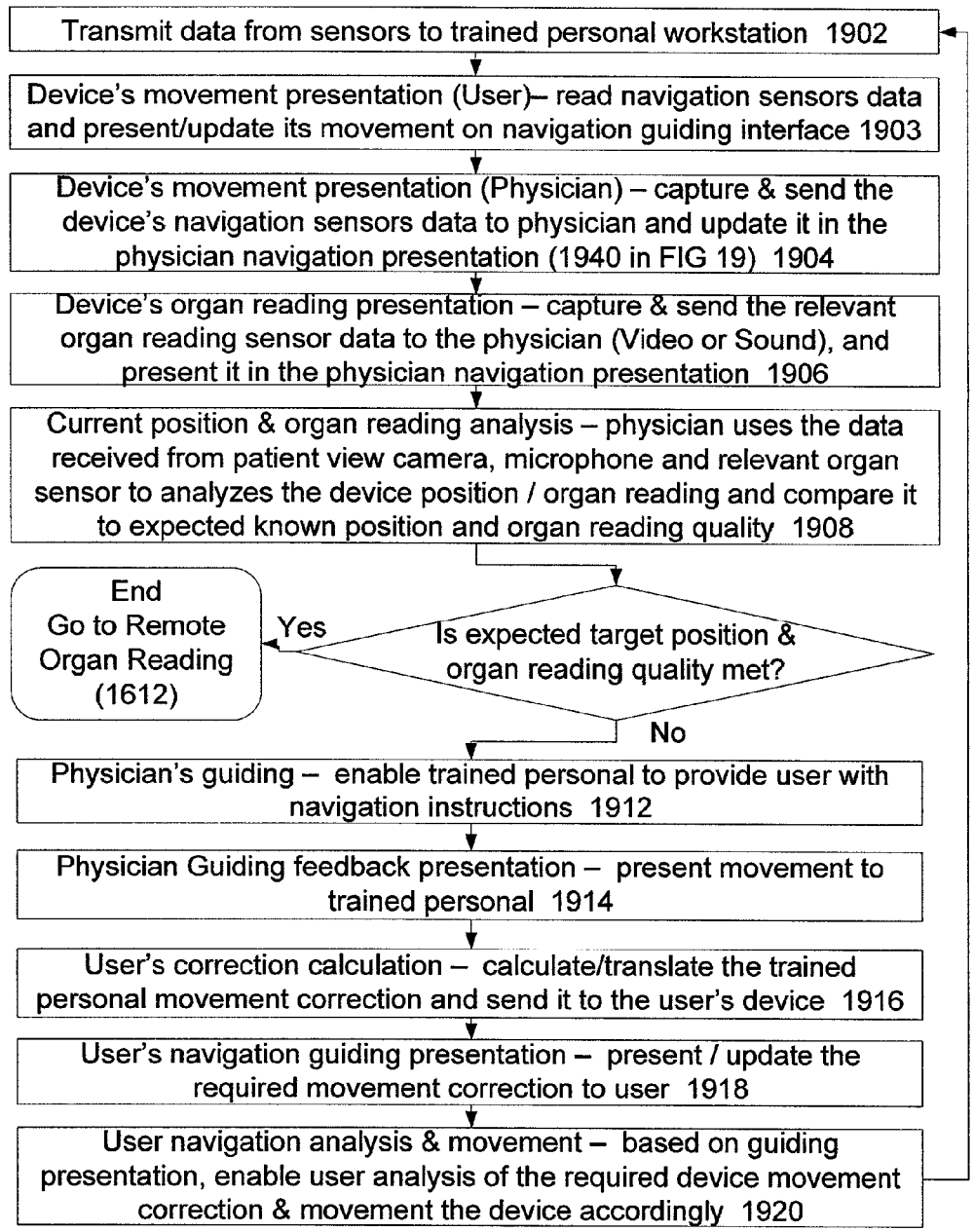
FIG. 18 is a flowchart illustrating one example of a sequence of operations carried out for navigating a diagnostic device and guiding a diagnostic device user accordingly in a remote trained personnel guided medical examination, in accordance with the presently disclosed subject matter.

FIG. 18 is a flowchart illustrating one example of a sequence of operations carried out for navigating a diagnostic device and guiding a diagnostic device user accordingly in a remote trained personnel guided medical examination, in accordance with the presently disclosed subject matter. Diagnostics device 104 can be configured to activate various diagnostics and navigation sensors (such as patient location camera 1114a, patient location microphone 1114b, diagnostics sensors 202, navigation module 204, etc.) while being moved by user 102 (step 1902). Diagnostics device 104 can be configured to continuously transmit (e.g. stream, for example in real time or near real-time) the data acquired by the various diagnostics and navigation sensors, inter alia to patient workstation 114 and/or to trained personnel workstation 122.

Patient workstation 114 can utilize the data acquired by the various navigation sensors for presenting (e.g. on a display) data on diagnostics device 104 movements to user 102 (step 1903) This can allow user 102 to receive an immediate feedback relating to diagnostics device 104 movement (prior to receiving a delayed movement correction feedback from trained personnel 124), thus making the navigation process easier. The data on diagnostics device 104 movements can be presented to user 102 for example using a representation of diagnostics device 104, such as, for example, shown in FIG. 13.

Trained personnel workstation 122 can utilize the data acquired by the various navigation sensors for presenting (e.g. on a display) data on diagnostics device 104 movements to trained personnel 124 (step 1904). The data on diagnostics device 104 movements can be presented to trained personnel 124 using a representation of diagnostics device 104, such as, for example, shown in FIG. 19 (see index 1940 in FIG. 19). Trained personnel workstation 122 can further utilize data acquired by the various diagnostics sensors for presenting (e.g. on a display) the data to trained personnel 124 (step 1906). The data acquired by the various diagnostics sensors can be presented to trained personnel 124 as, for example, shown in FIG. 19 (see index 1942 in FIG. 19).

Trained personnel 124 can then utilize the data presented to him (e.g. on a display) and determine if diagnostics device 104 is located in the desired spatial disposition with respect to patient's 103 body (or a specific part thereof) to acquire the required reading and if the current readings received from the diagnostics sensors are of sufficient quality (step 1908). If diagnostics device 104 is located in the desired spatial disposition with respect to patient's 103 body (or a specific part thereof) and the readings received from the diagnostics sensors are of sufficient quality trained personnel workstation 122 can be configured to enable trained personnel 124 to instruct it to continue to the step of acquiring the medical data (step 1612).

If diagnostics device 104 is not located in the desired spatial disposition with respect to patient's 103 body (or a specific part thereof) and/or the readings received from the diagnostics sensors are not of sufficient quality, trained personnel workstation 122 can be configured to enable trained personnel 124 to provide user 102 with instructions for navigating diagnostics device 104 to the desired spatial disposition with respect to patient's 103 body (or a specific part thereof) (step 1912). As detailed above, inter alia with reference to FIG. 17, the instructions can be voice instructions and/or visual instructions. In addition, if needed, trained personnel workstation 122 can be configured to enable trained personnel 124 to remotely change or adjust various parameters in diagnostic device 104 (e.g. manually control diagnostic device 104 sensors such as light intensity, camera focus, camera zoom, microphone sensitivity, etc.).

As indicated above, visual instructions can be based on utilization of guiding device 1124. In such cases, trained personnel workstation 122 can be configured to display the movements made by guiding device 1124 (e.g. on a display). The display can present the movements for example using a representation of diagnostics device 104, as shown for example in FIG. 19 (see index 1940 in FIG. 19) (step 1914). This presentation will allow trained personnel 124 to receive an immediate feedback relating to his guiding movement, before receiving the delayed feedback of user 102 corresponding movement using diagnostic device 104.

Trained personnel workstation 122 can be configured to transmit (e.g. stream in real time or near-real time) the instructions for correcting the navigation of diagnostics device 104 to the required spatial disposition with respect to patient's 103 body (or a specific part thereof) to patient workstation 114 or to diagnostic device 104 (step 1916). Patient workstation 114 can be configured to provide user 102 with the voice and/or visual instructions provided by trained personnel 124 (step 1918). The instructions can be provided for example by utilizing a display (e.g. display 502) and/or a speaker (e.g. speaker 510). Visual instructions can be presented, for example, as shown and described with reference to FIG. 13 above. Diagnostics device 104 can be further maneuvered by user 102 (step 1920) while repeating the process detailed above until diagnostics device 104 is positioned and oriented in the desired spatial disposition with respect to patient's 103 body (or a specific part thereof) for medical data acquisition.

FIG. 19 is a schematic illustration of an exemplary navigation and guiding presentation to trained personnel, in accordance with the presently disclosed subject matter. Trained personnel workstation 122 can be configured to display online visit screen 1930. Online visit screen can be divided to several areas that can contain various data relevant for performing a remote trained personnel guided medical examination. Such data can comprise for example patient & general information 1932, patient view 1936, organ readings—actual readings 1944, navigation and guiding presentation 1940, organ view—active sensor 1942 and application menu 1934.

Patient & general information 1932 can comprise, for example, various data and information about the patient and the online visit status, such as patient name, patient age, patient address, patient language, data relating to diseases and/or sensitivities to medicine, online visit date, time, duration etc.

Patient view 1936 can present, for example, data received (e.g. streamed in real time) from patient location camera 1114a or patient location microphone 1114b for enabling trained personnel 124 to see and hear patient 103 and/or user 102. This information can allow for example general patient 103 and diagnostics device 104 orientation as well as videoconferencing between trained personnel 124 and user 102 and/or patient 103.

Organ readings—actual readings 1944 can present for example data about reference readings, and/or past readings of the organ to be checked. Upon acquiring a patient 103 organ reading (e.g. organ image, video or sound), the result reading transferred from diagnostic device 104, can be presented in that area. In addition the organ readings—actual readings 1944 can allow video presentation, zooming, scaling etc. It is to be noted that the reading data presented in this area doesn't require real-time update.

Navigation and guiding presentation 1940 can present the current diagnostics device 104 spatial disposition with respect to patient's 103 body (or a specific part thereof), the desired diagnostics device 104 spatial disposition with respect to patient's 103 body (or a specific part thereof) and the required correction movement to be performed to diagnostics device 104 in order to move it to the desired spatial disposition with respect to patient's 103 body (or a specific part thereof). In addition the area can also present trained personnel guiding device 1124 position and orientation based on trained personnel 124 movement. Navigation and guiding presentation 1940, can also be configured to allow real-time presentation of the guiding/correction movement made by trained personnel 124 vs. the corresponding movement made by user 103 using diagnostic device 104, thus allowing visual presentation of the tracing of user 103 movements based on trained personnel 124 guiding & navigation correction.

Organ view—active sensor 1942 can present data received (e.g. streamed in real time or near real-time) from diagnostics sensors (e.g. image based sensors 310). Trained personnel 124 can use this data, inter alia in order to determine if medical data acquisition can be performed (e.g. diagnostics device 104 is positioned and oriented as desired, the image quality is good, etc.). It is to be noted that trained personnel workstation 122 can be configured to use lower quality real-time (or near real-time) data streaming in organ view—active sensor area 1942 (e.g. to increase performance and allow general device position), while using a higher quality reading in the organ reading—actual reading area 1944 (e.g. use higher quality sensor reading like high definition image and sound, to be transferred not in real time).

Application menu 1934 can present for example various operational options for operating the system, such as beginning a medical examination, saving a medical examination, acquiring medical data, inserting various written data to system (e.g. diagnostics data, comments, etc.), etc. In addition the application menu 1934 can be configured to allow a remote control of diagnostic device 104 sensors (e.g. light intense, zoom, focus, sound filters, etc.). It is to be noted that application menu 1934, can be also configured as context sensitive menu, e.g. the menu can add/remove functionality with relation to a specific window area currently in focus or being manipulated (e.g. add/remove specific functions related for example to a specific window area).

Figure 20:
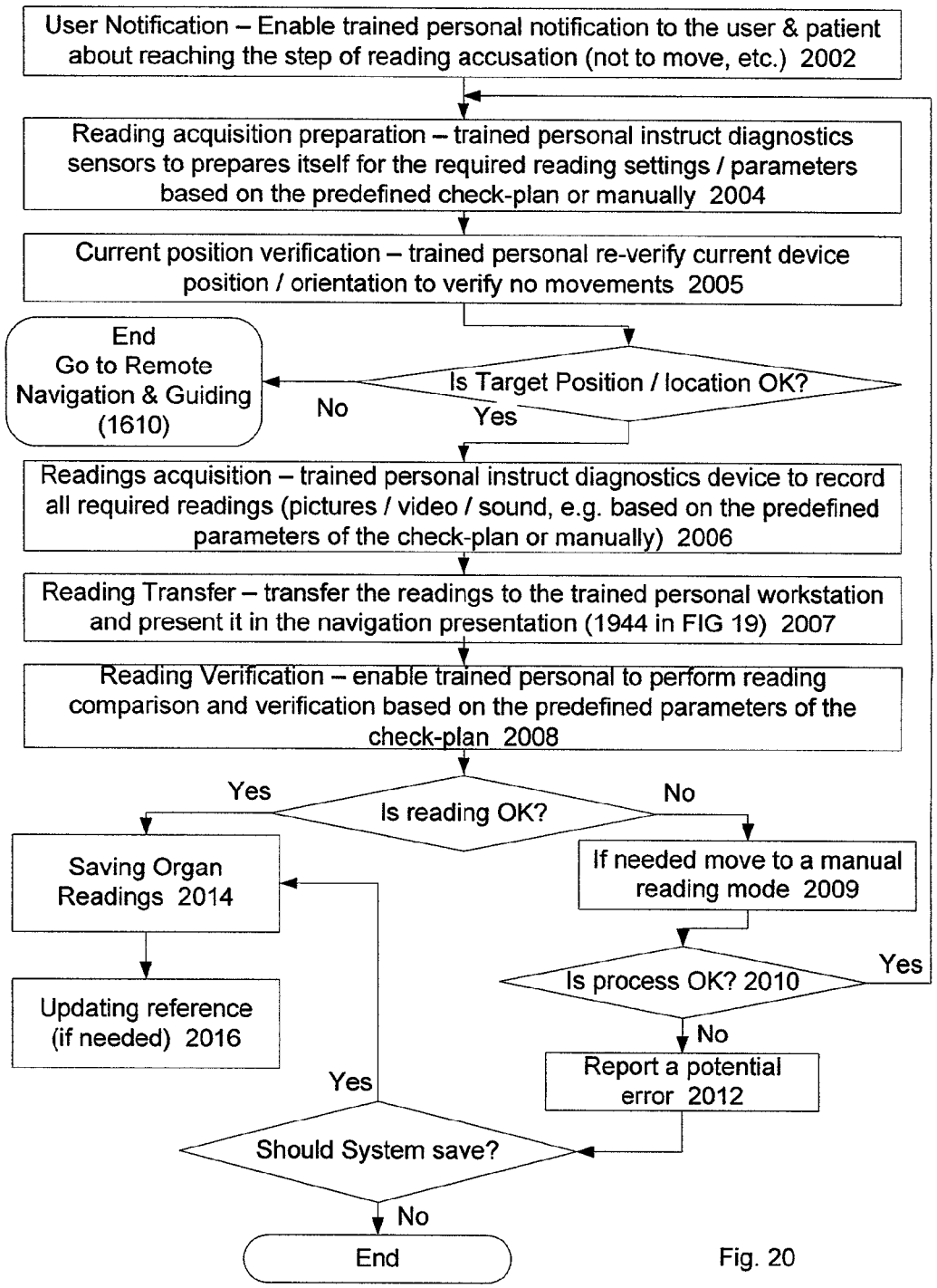
FIG. 20 is a flowchart illustrating one example of a sequence of operations carried out for acquisition and verification of a reading by a diagnostic device in a remote trained personnel guided medical examination, in accordance with the presently disclosed subject matter.

FIG. 20 is a flowchart illustrating one example of a sequence of operations carried out for acquisition and verification of a reading by a diagnostic device in a remote trained personnel guided medical examination, in accordance with the presently disclosed subject matter. Trained personnel workstation 122 can be configured to enable trained personnel 124 to provide user 102 with a notification that diagnostics device 104 is in the desired spatial disposition with respect to patient's 103 body (or a specific part thereof) (step 2002). The notification can be a voice notification, e.g. a voice recording acquired by trained personnel microphone 1122b, transmitted (e.g. streamed) to patient workstation 114 that can be configured to play it to user 102 (e.g. utilizing speaker 510). Alternatively or additionally, the notification can be a visual notification, as trained personnel 124 can instruct trained personnel workstation 122 to instruct patient workstation to display for example a notification on a display of patient workstation 114 or diagnostic device 104. The notification can, for example, instruct user 102 not to move diagnostics device.

Trained personnel workstation 122 can be configured to enable trained personnel 124 to instruct diagnostics device 104 and the diagnostics sensors to prepare to acquire medical data of patient 103 (step 2004). The preparation can be defined by the patient specific check plan or according to instructions provided by trained personnel 124. Such preparations can include preparing diagnostics sensors 202 to acquire medical data according to the patient specific check plan. Exemplary preparations are setting image acquisition sensor 316 zoom and/or focus, activating light sources 318 at correct power, activating sound acquisition sensor 324, etc. In addition diagnostic device 104 can be configured to retrieve the relevant reading parameters and thresholds for example from the patient specific check plan (e.g. the required length of reading, reference thresholds such as minimal sound volume, etc.). It is to be noted that trained personnel 124 can also manually adjust or change the relevant reading parameters and thresholds (e.g. override the patient specific check plan).

Trained personnel workstation 122 can be configured to enable trained personnel 124 to re-evaluate diagnostics device 104 current spatial disposition with respect to patient's 103 body (or a specific part thereof) and verify that no movements have been made and that it is still located in the desired spatial disposition with respect to patient's 103 body (or a specific part thereof) (step 2005). In case there has been a change in diagnostics device 104 position and/or orientation, trained personnel workstation 122 can be configured to enable trained personnel 124 to return to the navigation and guiding process (1610). Otherwise, trained personnel workstation 122 can be configured to enable trained personnel 124 to perform medical data acquisition utilizing diagnostics device 104 (step 2006). The medical data can be acquired according to the check plan, that, as indicted above, can include information, inter alia about the examination process, steps and logic, and predefined reading parameters such as type of sensor to be used (still image vs. video), required length of reading (sound or video recording) in terms of time (e.g. seconds), and reading data thresholds (for example definition of acceptable minimal and/or maximal reading limits to be used as a quality parameter of a reading. Thus, for example, if the heart is to be checked, the check plan can define that the sound based sensors 320 are to be used and that the reading length should be 3 seconds, or between 2.5 and 5 seconds, etc.). It is to be noted that trained personnel 124 can also manually adjust or change the relevant reading parameters and thresholds (e.g. override the patient specific check plan).

Following medical data acquisition, the data can be transmitted (e.g. streamed) to trained personnel workstation 122 which can then display the acquired data to trained personnel 124, as shown for example in FIG. 19 (see index 1944 in FIG. 19) (step 2007).

Trained personnel workstation 122 can be configured to enable trained personnel 124 to verify that the acquired medical data meets pre-defined standards (e.g. a required length of reading, reading data thresholds, etc.) (step 2008). For example, if the heart is to be checked, and the check plan defines that the reading length should be between 2.5 and 5 seconds, trained personnel workstation 122 can be configured to enable trained personnel 124 to check that the reading length meets the requirement. In case the acquired medical data did not meet the pre-defined standards, trained personnel workstation 122 can be configured to enable trained personnel 124 to check if the acquired medical data is ok (for example that the acquired medical data is of sufficient quality, etc.).

In case the acquired medical data is not ok (for example that the acquired medical data is not of sufficient quality, etc.), trained personnel workstation 122 can be configured to enable trained personnel 124 to perform a manual reading (step 2009). As noted above trained personnel workstation 122 can be configured to enable trained personnel 124 to manually adjust or control different diagnostic device 104 parameters such as light intensity, camera focus, camera zoom, reading duration, sound filtering, etc.

If the acquired medical data is still not ok after the manual reading 2009, but the process was ok (e.g. diagnostic device 104 did not report any error, and the guiding process was performed correctly), trained personnel workstation 122 can be configured to enable trained personnel 124 to return to step 2004 (in order to retry acquiring the medical data). If the process was not ok, trained personnel workstation 122 can be configured to issue a notification to trained personnel 124 of a potential error (for example by presenting a message on trained personnel workstation 122, etc.) and enable him to decide if the acquired medical data is to be saved or not. If user 102 chooses to save the acquired medical data, or the acquired medical data is ok, trained personnel workstation 122 can be configured to enable trained personnel 124 to save the acquired medical data (for example, in one or more of a data repository 216, patient & check plan repository 136, trained personnel data repository 123 or any other location operatively connected to diagnostics device 104 on which patient data is stored) (step 2014).

Optionally, in case the reading acquisition process was ok, trained personnel workstation 122 can be configured to update the reference data with the acquired medical data (step 2016). This can be performed in order to keep the reference data up to date, as changes can occur to the human body (for example in light of growing up, aging, medical treatments, etc.).

It is to be noticed that each of the components and modules described above can be combined with one or more of the other components and modules described above.

It is to be noted that when referring to part of the functionality described as performed by diagnostics device 104 can be performed, alternatively or additionally, by any one of patient workstation 114 or by any other suitable device, including, but not limited to, trained personnel workstation 122, central system 130, etc.

It is to be noted that, with reference to FIGS. 6, 7, 8*a*,8*b*,8*c*, 11, 12, 12*a*, 14, 17, 18, 20, some of the blocks/steps can be integrated into a consolidated block/step or can be broken down to a few blocks/steps and/or other blocks/steps may be added. Furthermore, in some cases, the blocks/steps can be performed in a different order than described herein. It should be also noted that whilst the flow diagrams are described also with reference to the system elements that realizes them, this is by no means binding, and the blocks/steps can be performed by elements other than those described herein.

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the present presently disclosed subject matter.

It will also be understood that the system according to the presently disclosed subject matter may be a suitably programmed computer. Likewise, the presently disclosed subject matter contemplates a computer program being readable by a computer for executing the method of the presently disclosed subject matter. The presently disclosed subject matter further contemplates a machine-readable memory tangibly embodying a program of instructions executable by the machine for executing the method of the presently disclosed subject matter.

The invention claimed is:

1. A handheld diagnostics device configured to perform one or more medical examinations of a patient, said diagnostics device comprising:
    at least one diagnostics sensor;
    at least one navigation sensor; and
    a processor;

wherein, for at least one medical examination of the medical examinations, said processor is configured to:

provide reference data indicative of a desired spatial disposition of the diagnostics device with respect to the patient's body for performing said medical examination;

acquire navigation enabling data utilizing the at least one navigation sensor;

determine, based on matching reference points within the acquired navigation enabling data and the reference data, a apatial disposition of the diagnostics device with respect to the desired spatial disposition;

calculate a required movement correction from the determined spatial disposition to the desired spatial disposition, for acquiring medical data of the patient in accordance with said at least one medical examination;

provide a user with maneuvering instructions to navigate said diagnostics device to the desired spatial disposition in accordance with the calculated route; and operate the at least one diagnostics sensor to acquire said medical data upon arrival to the desired spatial disposition.

2. The handheld diagnostics device according to claim 1 wherein the reference data and the navigation enabling data are body or body organ images.

3. The handheld diagnostics device according to claim 1 wherein the reference data and the navigation enabling data is Inertial Navigation System (INS) data received from the at least one navigation sensor.

4. The handheld diagnostics device according to claim 2 wherein said processor is configured to perform the following steps in order to determine the diagnostics device spatial disposition with respect to the desired spatial disposition:

compare said at least one image with said reference image in order to find matching reference points within the acquired navigation enabling data and the reference data; and determine, based on said comparison, the diagnostics device spatial disposition with respect to said desired spatial disposition.

5. The handheld diagnostics device according to claim 3 wherein said processor is configured to perform the following steps in order to determine the diagnostics device spatial disposition with respect to the desired spatial disposition:

receive INS data acquired in at least three pre-defined reference points on the patient's body;

determine, based on the received INS data, the diagnostics device spatial disposition with respect to said desired spatial disposition.

6. The handheld diagnostics device according to claim 5 wherein said determine is based on triangulation techniques while utilizing the received INS data acquired in at least three pre-defined reference points on the patient's body.

7. The handheld diagnostics device according to claim 1 wherein said processor is further configured to transmit the acquired medical data to a remote workstation.

8. The handheld diagnostics device according to claim 7 wherein said processor is configured to perform said transmit via a central system.

9. The handheld diagnostics device according to claim 8 wherein said central system automatically routes the acquired medical data to a remote workstation of an available trained personnel out of a plurality of trained personnel, whereby at least one of said plurality of trained personnel is not available.

10. The handheld diagnostics device according to claim 1 wherein said processor is further configured to:

provide said user with one or more questions relating to the patient; receive answers to the one or more questions; and transmit said answers to said remote workstation.

11. The handheld diagnostics device according to claim 1 wherein the reference data is acquired during a calibration process performed by a trained personnel.

12. The handheld diagnostics device according to claim 11 wherein said processor is further configured to perform the following steps during the calibration process:

receive an indication of a medical examination to be performed;

provide the trained personnel with guidance for performing the calibration; and upon arrival to the desired diagnostics device spatial disposition, record said reference data indicative of the desired spatial disposition of the diagnostics device with respect to the patient's body.

13. The handheld diagnostics device according to claim 1 wherein said reference data includes reference medical data and wherein said processor is further configured to:

replace existing reference medical data with the respective acquired medical data thereby maintaining updated reference medical data.

14. The handheld diagnostics device according to claim 1 wherein a pre-defined check plan associated with the patient defines a list of the one or more medical examinations to be performed on the patient.

15. The handheld diagnostics device according to claim 1 wherein the diagnostics sensor is an image based diagnostics sensor.

16. The handheld diagnostics device according to claim 1 wherein the diagnostics sensor is a sound based diagnostics sensor.

17. The handheld diagnostics device according to claim 2 wherein the navigation sensor is a camera.

18. The handheld diagnostics device according to claim 3 wherein the navigation sensor is an INS.

19. The handheld diagnostics device according to claim 1 wherein the maneuvering instructions are voice instructions provided via a speaker.

20. The handheld diagnostics device according to claim 1 wherein the maneuvering instructions are visual instructions provided via a display.

21. The handheld diagnostics device according to claim 1 wherein the maneuvering instructions are vibration instructions provided via vibration elements.

22. The handheld diagnostics device according to claim 1 wherein the processor is further configured to verify that the acquired data meets pre-defined standards.

23. The handheld diagnostics device according to claim 22 wherein the pre-defined standards are at least one of:

(a) a required length of reading;
(b) a minimal recorded sound volume;
(c) a minimal recorded sound quality;
(d) a minimal pressure against the patient's body;
(e) a maximal pressure against the patient's body;
(f) a maximal allowed movement of the diagnostics device during acquisition of readings;
(g) a type of image reading;
(h) a required image reading zoom;
(i) a required image reading light;
(j) a required image reading matching to predefined reference; and
(k) a minimal image quality.

24. The handheld diagnostics device according to claim 1 wherein the reference data is generic reference data not related to a specific patient.

25. The handheld diagnostics device according to claim 1 wherein the processor is further configured to automatically identify the patient.

26. A method for performing one or more medical examinations of a patient using a diagnostics device, wherein for at least one medical examination of the medical examinations, said method comprising:
providing reference data indicative of a desired spatial disposition of the diagnostics device with respect to the patient's body for performing said medical examination;
operating said diagnostics device for acquiring navigation enabling data;
determining, using a processor, based on matching reference points within the acquired navigation enabling data and the reference data, a spatial disposition of the diagnostics device with respect to the desired spatial disposition;
calculating a required movement correction from the determined spatial disposition to the desired spatial disposition, for acquiring medical data of the patient in accordance with said at least one medical examination;
providing a user with maneuvering instructions to navigate the diagnostics device to said desired spatial disposition in accordance with the calculated route; and
acquiring said medical data upon arrival to the desired spatial disposition.

27. The method according to claim 26 wherein the reference data and the navigation enabling data are body or body organ images.

28. The method according to claim 26 wherein the reference data and the navigation enabling data is Inertial Navigation System (INS) data received from the at least one navigation sensor.

29. The method according to claim 27 wherein said determining comprises:
comparing said navigation enabling data with said reference data in order to find matching reference points within the acquired navigation enabling data and the reference data; and
determining, based on said comparing, the diagnostics device spatial disposition with respect to said desired spatial disposition.

30. The method according to claim 28 wherein said determining comprises:
receiving INS data acquired in at least three pre-defined reference points on the patient's body;
determining, based on the received INS data and the reference data, the diagnostics device spatial disposition with respect to said desired spatial disposition.

31. The method according to claim 30 wherein said determining is based on triangulation techniques while utilizing the received INS data acquired in at least three pre-defined reference points on the patient's body.

32. The method according to claim 26 further comprising transmitting the acquired medical data to a trained personnel workstation.

33. The method according to claim 32 wherein said transmitting is performed via a central system.

34. The method according to claim 33 wherein said central system automatically routes the acquired medical data to an available trained personnel out of a plurality of trained personnel, whereby at least one of said plurality of trained personnel is not available.

35. The method according to claim 26 further comprising:
providing said user with one or more questions relating to the patient; receiving answers to the one or more questions; and
transmitting said answers to said trained personnel.

36. The method according to claim 26 wherein the reference data is acquired during a calibration process performed by a trained personnel.

37. The method according to claim 36 wherein said calibration process comprises:
receiving an indication of a medical examination to be performed;
providing the trained personnel with guidance for performing the calibration; and
upon arrival to the desired diagnostics device spatial disposition, recording said reference data indicative of the desired spatial disposition of the diagnostics device with respect to the patient's body.

38. The method according to claim 26 wherein said reference data includes reference medical data and wherein the method further comprises replacing existing reference medical data with the respective acquired medical data thereby maintaining updated reference medical data.

39. The method according to claim 26 wherein a pre-defined check plan associated with the patient defines a list of the one or more medical examinations to be performed on the patient.

40. The method according to claim 26 wherein the maneuvering instructions are voice instructions provided via a speaker.

41. The method according to claim 26 wherein the maneuvering instructions are visual instructions provided via a display.

42. The method according to claim 26 wherein the maneuvering instructions are vibration instructions provided via vibration elements.

43. The method according to claim 26 further comprising verifying that the acquired data meets pre-defined standards.

44. The method according to claim 43 wherein the pre-defined standards are at least one of:
(a) a required length of reading;
(b) a minimal recorded sound volume;
(c) a minimal recorded sound quality;
(d) a minimal pressure against the patient's body;
(e) a maximal pressure against the patient's body;
(f) a maximal allowed movement of the diagnostics device during acquisition of readings;
(g) a type of image reading;
(h) a required image reading zoom;
(i) a required image reading light;
(j) a required image reading matching to predefined reference.

45. The method according to claim 26 wherein the reference data is generic reference data not related to a specific patient.

46. The method according to claim 26 further comprising automatically identifying the patient.

47. A computer program comprising computer program stored on a non-transitory medium, comprising computer program code means for performing all the steps of claim 26 when said program is run on a computer.

48. A handheld diagnostics device configured to perform one or more medical examinations of a patient, said diagnostics device comprising:
at least one diagnostics sensor;
at least one navigation sensor; and
a processor;

wherein, for at least one medical examination of the medical examinations, said processor is configured to:
provide reference data indicative of a desired spatial disposition of a pointing object, pointing at the physical patient's body, with respect to the patient's body for performing said medical examination;
receive navigation enabling data from the at least one navigation sensor;
determine, based on matching reference points within the acquired navigation enabling data and the reference data, a spatial disposition of the pointing object with respect to the desired spatial disposition;
calculate a required movement correction from the determined spatial disposition to the desired spatial disposition, for acquiring medical data of the patient in accordance with said at least one medical examination;
provide a user with maneuvering instructions to navigate said pointing object, pointing at the physical patient's body, to the desired spatial disposition in accordance with the calculated required movement correction;
instruct the user to move the diagnostics device to the location indicated by the pointing object upon arrival of the pointing object to the desired spatial disposition; and
operate the at least one diagnostics sensor to acquire said medical data.

49. A method for performing one or more medical examinations of a patient using a diagnostics device, wherein for at least one medical examination of the medical examinations, said method comprising:
providing reference data indicative of a desired spatial disposition of a pointing object with respect to the patient's body for performing said medical examination;
operating said diagnostics device for acquiring navigation enabling data;
determining, using a processor, based on matching reference points within the acquired navigation enabling data and the reference data, a spatial disposition of the pointing object pointing at the physical patient's body, with respect to the desired spatial disposition;
calculating a required movement correction from the determined spatial disposition to the desired spatial disposition, for acquiring medical data of the patient in accordance with said at least one medical examination;
providing a user with maneuvering instructions to navigate said pointing object, pointing at the physical patient's body to said desired spatial disposition in accordance with the calculated required movement correction;
instructing the user to move the diagnostics device to the location indicated by the pointing object upon arrival of the pointing object to the desired spatial disposition; and
operating the at least one diagnostics sensor to acquire said medical data.

50. The handheld diagnostics device of claim 17 wherein the camera is also the diagnostics sensor.

51. The handheld diagnostics device according to claim 4 wherein said navigation enabling data further comprises Inertial Navigation System (INS) data and wherein said processor is further configured to perform the following additional steps in order to determine the diagnostics device spatial disposition with respect to the desired spatial disposition:
receive INS data acquired in at least three pre-defined reference points on the patient's body;
determine, based on the received INS data, the diagnostics device spatial disposition with respect to said desired spatial disposition.

52. The handheld diagnostics device according to claim 20 wherein the display is comprised within the handheld diagnostics device.

53. The method of claim 22 wherein said operate and said verify are performed automatically upon arrival to said desired spatial disposition.

54. The method of claim 29 wherein said navigation enabling data further comprises Inertial Navigation System (INS) data, and wherein said determining further comprises:
receiving INS data acquired in at least three pre-defined reference points on the patient's body;
determining, based on the received INS data and the reference data, the diagnostics device spatial disposition with respect to said desired spatial disposition.

55. The method of claim 41 wherein the display is comprised within the handheld diagnostics device.

56. The method of claim 43 wherein said acquiring and said verifying are performed automatically upon arrival to said desired spatial disposition.

* * * * *